US011642476B2

(12) United States Patent
Besseler et al.

(10) Patent No.: US 11,642,476 B2
(45) Date of Patent: *May 9, 2023

(54) NEBULIZER

(71) Applicant: Boehringer Ingelheim International GmbH, Ingelheim am Rhein (DE)

(72) Inventors: Jens Besseler, Bingen (DE); Frank Herrmann, Duisburg (DE); Holger Holakovsky, Witten (DE); Herbert Argauer, Pirk (DE); Josef Gatz, Moosbach (DE); Andreas Gorshoefer, Nittenau (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 303 days.

This patent is subject to a terminal disclaimer.

(21) Appl. No.: 17/122,043

(22) Filed: Dec. 15, 2020

(65) Prior Publication Data
US 2021/0093807 A1    Apr. 1, 2021

Related U.S. Application Data

(63) Continuation of application No. 15/942,737, filed on Apr. 2, 2018, now Pat. No. 10,894,134, which is a
(Continued)

(30) Foreign Application Priority Data

Aug. 9, 2013 (EP) .................................. 13003987

(51) Int. Cl.
*A61M 15/00* (2006.01)
*A61M 11/00* (2006.01)
*A61M 11/02* (2006.01)

(52) U.S. Cl.
CPC ........ *A61M 15/0081* (2014.02); *A61M 11/00* (2013.01); *A61M 11/007* (2014.02);
(Continued)

(58) Field of Classification Search
CPC .... A61M 11/00; A61M 11/007; A61M 15/00; A61M 15/0001; A61M 15/0065;
(Continued)

(56) References Cited

U.S. PATENT DOCUMENTS 1,828,864 A    10/1931    Hopkins
2,015,970 A    10/1935    Schoene
(Continued)

FOREIGN PATENT DOCUMENTS

AU    2005201364 A1    7/2006
CA       1094549 A     1/1981
(Continued)

OTHER PUBLICATIONS

International Search Report and Written Opinion for PCT/EP04006768, 10 pages, dated Sep. 24, 2004.
(Continued)

*Primary Examiner* — Joseph D. Boecker
(74) *Attorney, Agent, or Firm* — Matthew B. Dernier, Esq.

(57) ABSTRACT

A nebulizer for a fluid, includes a container containing the fluid; a housing part which can be detached from the nebulizer for replacing the container; an inner part; a retaining element connected with and not detachable from the inner part, where the housing part is releasable fixed to the inner part by the retaining element; a delivery mechanism for dispensing the fluid; a manually depressible actuator member, which is a separate part from the retaining element and acts on the retaining element, and wherein the actuator
(Continued)

member is depressed to elastically deform or flex the retaining element to allow detachment of the housing part.

18 Claims, 21 Drawing Sheets

Related U.S. Application Data continuation of application No. 14/453,805, filed on Aug. 7, 2014, now Pat. No. 10,004,857.

(52) U.S. Cl.
CPC ............ *A61M 11/02* (2013.01); *A61M 15/00* (2013.01); *A61M 15/0001* (2014.02); *A61M 15/004* (2014.02); *A61M 15/009* (2013.01); *A61M 15/0036* (2014.02); *A61M 15/0065* (2013.01); *A61M 15/0066* (2014.02); *A61M 15/0071* (2014.02); *A61M 15/0073* (2014.02); *A61M 15/0025* (2014.02); *A61M 2202/04* (2013.01); *A61M 2202/064* (2013.01); *A61M 2205/27* (2013.01); *A61M 2205/273* (2013.01); *A61M 2205/276* (2013.01); *A61M 2205/583* (2013.01); *A61M 2205/584* (2013.01); *A61M 2205/6045* (2013.01)

(58) Field of Classification Search
CPC .......... A61M 15/0066; A61M 15/0068; A61M 15/0071; A61M 15/0073; A61M 15/0081; A61M 15/009; A61M 2205/276
See application file for complete search history.

(56) References Cited

U.S. PATENT DOCUMENTS

| | | |
|---|---|---|
| 2,127,401 A | 8/1938 | Gillican |
| 2,161,071 A | 6/1939 | McGrath et al. |
| 2,321,428 A | 6/1943 | Schloz |
| 2,329,311 A | 9/1943 | Waters |
| 2,362,103 A | 11/1944 | Smith |
| 2,651,303 A | 9/1953 | Johnson et al. |
| 2,720,969 A | 10/1955 | Kendall |
| 2,793,776 A | 5/1957 | Lipari |
| 2,974,880 A | 3/1961 | Stewart et al. |
| 3,032,823 A | 5/1962 | Sherman et al. |
| 3,157,179 A | 11/1964 | Allen et al. |
| 3,172,568 A | 3/1965 | Modderno |
| 3,196,587 A | 7/1965 | Hayward et al. |
| 3,223,289 A | 12/1965 | Bouet |
| 3,299,603 A | 1/1967 | Shaw |
| 3,348,726 A | 10/1967 | La Cross |
| 3,354,883 A | 11/1967 | Southerland |
| 3,425,591 A | 2/1969 | Pugh, Sr. |
| 3,440,144 A | 4/1969 | Anderson et al. |
| 3,457,694 A | 7/1969 | Tatibana |
| 3,491,803 A | 1/1970 | Galik |
| 3,502,035 A | 3/1970 | Fedit |
| 3,580,249 A | 5/1971 | Takaoka |
| 3,590,557 A | 7/1971 | Vogel |
| 3,606,106 A | 9/1971 | Yuhas |
| 3,632,743 A | 1/1972 | Geller et al. |
| 3,655,096 A | 4/1972 | Easter |
| 3,674,060 A | 7/1972 | Ruekberg |
| 3,675,825 A | 7/1972 | Morane |
| 3,684,124 A | 8/1972 | Song |
| 3,802,604 A | 4/1974 | Morane et al. |
| 3,817,416 A | 6/1974 | Costa |
| 3,820,698 A | 6/1974 | Franz |
| 3,842,836 A | 10/1974 | Ogle |
| 3,858,580 A | 1/1975 | Ogle |
| 3,861,851 A | 1/1975 | Schiemann |
| 3,870,147 A | 3/1975 | Orth |
| 3,924,741 A | 12/1975 | Kachur et al. |
| 3,933,279 A | 1/1976 | Maier |
| 3,946,732 A | 3/1976 | Hurscham |
| 3,949,751 A | 4/1976 | Birch et al. |
| 3,951,310 A | 4/1976 | Steiman |
| 3,953,995 A | 5/1976 | Haswell et al. |
| 3,973,603 A | 8/1976 | Franz |
| 4,012,472 A | 3/1977 | Lindsey |
| 4,031,892 A | 6/1977 | Hurschman |
| 4,036,439 A | 7/1977 | Green |
| 4,048,997 A | 9/1977 | Raghavachari et al. |
| 4,067,499 A | 1/1978 | Cohen |
| 4,094,317 A | 6/1978 | Wasnich |
| 4,120,995 A | 11/1978 | Phipps |
| 4,126,559 A | 11/1978 | Cooper |
| 4,153,689 A | 5/1979 | Hirai et al. |
| 4,174,035 A | 11/1979 | Wiegner |
| 4,177,938 A | 12/1979 | Brina |
| 4,178,928 A | 12/1979 | Tischlinger |
| 4,195,730 A | 4/1980 | Hunt |
| 4,245,788 A | 1/1981 | Wright |
| 4,275,840 A | 6/1981 | Staar |
| 4,315,570 A | 2/1982 | Silver et al. |
| 4,338,765 A | 7/1982 | Ohmori et al. |
| 4,377,106 A | 3/1983 | Workman et al. |
| 4,434,908 A | 3/1984 | French |
| 4,456,016 A | 6/1984 | Nowacki et al. |
| 4,463,867 A | 8/1984 | Nagel |
| 4,467,965 A | 8/1984 | Skinner |
| 4,474,302 A | 10/1984 | Golderberg |
| 4,476,116 A | 10/1984 | Anik |
| 4,515,586 A | 5/1985 | Mendenhall et al. |
| 4,516,967 A | 5/1985 | Kopfer |
| 4,524,888 A | 6/1985 | Tada |
| 4,603,794 A | 8/1986 | DeFord et al. |
| 4,677,975 A | 7/1987 | Edgar et al. |
| 4,727,985 A | 3/1988 | McNeirney et al. |
| 4,749,082 A | 6/1988 | Gardiner et al. |
| 4,796,614 A | 1/1989 | Nowacki et al. |
| 4,805,377 A | 2/1989 | Carter |
| 4,813,210 A | 3/1989 | Masuda et al. |
| 4,821,923 A | 4/1989 | Skorka |
| 4,840,017 A | 6/1989 | Miller et al. |
| 4,863,720 A | 9/1989 | Burghart et al. |
| 4,868,582 A | 9/1989 | Dreinhoff |
| 4,885,164 A | 12/1989 | Thurow |
| 4,905,450 A | 3/1990 | Hansen et al. |
| 4,926,613 A | 5/1990 | Hansen |
| 4,951,661 A | 8/1990 | Sladek |
| 4,952,310 A | 8/1990 | McMahan et al. |
| 4,964,540 A | 10/1990 | Katz |
| RE33,444 E | 11/1990 | Lerner |
| 4,973,318 A | 11/1990 | Holm et al. |
| 4,979,941 A | 12/1990 | Ogle, II |
| 4,982,875 A | 1/1991 | Pozzi et al. |
| 5,014,492 A | 5/1991 | Fiorini et al. |
| 5,025,957 A | 6/1991 | Ranalletta et al. |
| 5,059,187 A | 10/1991 | Sperry et al. |
| 5,060,791 A | 10/1991 | Zulauf |
| 5,067,655 A | 11/1991 | Farago et al. |
| 5,156,918 A | 10/1992 | Marks et al. |
| 5,174,366 A | 12/1992 | Nagakura et al. |
| 5,207,217 A | 5/1993 | Cocozza et al. |
| 5,230,884 A | 7/1993 | Evans et al. |
| 5,237,797 A | 8/1993 | Varlet |
| 5,246,142 A | 9/1993 | DiPalma et al. |
| 5,261,565 A | 11/1993 | Drobish et al. |
| 5,263,842 A | 11/1993 | Fealey |
| 5,271,153 A | 12/1993 | Reiboldt et al. |
| 5,282,304 A | 2/1994 | Reiboldt et al. |
| 5,282,549 A | 2/1994 | Scholz et al. |
| 5,284,133 A | 2/1994 | Burns et al. |
| 5,289,948 A | 3/1994 | Moss et al. |
| 5,339,990 A | 8/1994 | Wilder |
| 5,352,196 A | 10/1994 | Haber et al. |
| 5,380,281 A | 1/1995 | Tomellini et al. |
| 5,385,140 A | 1/1995 | Smith |
| 5,388,572 A | 2/1995 | Mulhauser |
| 5,394,866 A | 3/1995 | Ritson et al. |
| 5,408,994 A | 4/1995 | Wass et al. |

(56) References Cited

U.S. PATENT DOCUMENTS

| | | | |
|---|---|---|---|
| 5,433,343 A | 7/1995 | Meshberg |
| 5,435,282 A | 7/1995 | Haber et al. |
| 5,435,884 A | 7/1995 | Simmons et al. |
| 5,451,569 A | 9/1995 | Wong et al. |
| 5,456,522 A | 10/1995 | Beach |
| 5,456,533 A | 10/1995 | Streiff et al. |
| 5,472,143 A | 12/1995 | Bartels et al. |
| 5,482,030 A | 1/1996 | Klein |
| 5,487,378 A | 1/1996 | Robertson et al. |
| 5,497,944 A | 3/1996 | Weston et al. |
| 5,499,750 A | 3/1996 | Manifold |
| 5,499,751 A | 3/1996 | Meyer |
| 5,503,869 A | 4/1996 | Van Oort |
| 5,509,404 A | 4/1996 | Lloyd et al. |
| 5,518,147 A | 5/1996 | Peterson et al. |
| 5,533,994 A | 7/1996 | Meyer |
| 5,541,569 A | 7/1996 | Jang |
| 5,544,646 A | 8/1996 | Lloyd et al. |
| 5,547,094 A | 8/1996 | Bartels et al. |
| 5,569,191 A | 10/1996 | Meyer |
| 5,574,006 A | 11/1996 | Yanagawa |
| 5,579,760 A | 12/1996 | Kohler |
| 5,584,285 A | 12/1996 | Salter et al. |
| 5,593,069 A | 1/1997 | Jinks |
| 5,599,297 A | 2/1997 | Chin et al. |
| 5,603,943 A | 2/1997 | Yanagawa |
| 5,614,172 A | 3/1997 | Geimer |
| 5,622,162 A | 4/1997 | Johansson et al. |
| 5,622,163 A | 4/1997 | Jewett et al. |
| 5,643,868 A | 7/1997 | Weiner et al. |
| 5,662,098 A | 9/1997 | Yoshida |
| 5,662,271 A | 9/1997 | Weston |
| 5,676,930 A | 10/1997 | Jager et al. |
| 5,685,846 A | 11/1997 | Michaels, Jr. |
| 5,697,242 A | 12/1997 | Halasz et al. |
| 5,709,202 A | 1/1998 | Lloyd et al. |
| 5,722,598 A | 3/1998 | Werding |
| 5,738,087 A | 4/1998 | King |
| 5,740,967 A | 4/1998 | Simmons et al. |
| 5,763,396 A | 6/1998 | Weiner et al. |
| 5,775,321 A | 7/1998 | Alband |
| 5,782,345 A | 7/1998 | Guasch et al. |
| 5,827,262 A | 10/1998 | Neftel et al. |
| 5,829,435 A | 11/1998 | Rubsamen et al. |
| 5,833,088 A | 11/1998 | Kladders et al. |
| 5,848,588 A | 12/1998 | Foley et al. |
| 5,868,287 A | 2/1999 | Kurokawa et al. |
| 5,881,718 A | 3/1999 | Mortensen et al. |
| 5,884,620 A | 3/1999 | Gonda et al. |
| 5,902,298 A | 5/1999 | Niedospial, Jr. et al. |
| 5,934,272 A | 8/1999 | Lloyd et al. |
| 5,935,101 A | 8/1999 | Kato et al. |
| 5,941,244 A | 8/1999 | Yamazaki et al. |
| 5,950,016 A | 9/1999 | Tanaka |
| 5,950,403 A | 9/1999 | Yamaguchi et al. |
| 5,951,882 A | 9/1999 | Simmons et al. |
| 5,964,416 A | 10/1999 | Jaeger et al. |
| 5,975,370 A | 11/1999 | Durliat |
| 5,997,263 A | 12/1999 | Van Lintel et al. |
| 6,041,777 A | 3/2000 | Faithfull et al. |
| 6,041,969 A | 3/2000 | Parise |
| 6,053,368 A | 4/2000 | Geimer |
| 6,062,430 A | 5/2000 | Fuchs |
| 6,098,618 A | 8/2000 | Jennings et al. |
| 6,109,479 A | 8/2000 | Ruckdeschel |
| 6,110,247 A | 8/2000 | Birmingham et al. |
| 6,116,233 A | 9/2000 | Denyer et al. |
| 6,119,853 A | 9/2000 | Garrill et al. |
| 6,120,492 A | 9/2000 | Finch et al. |
| 6,123,068 A | 9/2000 | Lloyd et al. |
| 6,131,566 A | 10/2000 | Ashurst et al. |
| 6,145,703 A | 11/2000 | Opperman |
| 6,149,054 A | 11/2000 | Cimillo et al. |
| 6,152,296 A | 11/2000 | Shih |
| 6,171,972 B1 | 1/2001 | Mehregany et al. |
| 6,176,442 B1 | 1/2001 | Eicher et al. |
| 6,179,118 B1 | 1/2001 | Garrill et al. |
| 6,186,409 B1 | 2/2001 | Srinath et al. |
| 6,199,766 B1 | 3/2001 | Fox et al. |
| 6,223,933 B1 | 5/2001 | Hochrainer et al. |
| 6,224,568 B1 | 5/2001 | Morimoto et al. |
| 6,237,589 B1 | 5/2001 | Denyer et al. |
| 6,259,654 B1 | 7/2001 | de la Huerga |
| 6,267,154 B1 | 7/2001 | Felicelli et al. |
| 6,279,786 B1 | 8/2001 | de Pous et al. |
| 6,302,101 B1 | 10/2001 | Py |
| 6,315,173 B1 | 11/2001 | Di Giovanni et al. |
| 6,319,943 B1 | 11/2001 | Joshi et al. |
| 6,336,453 B1 | 1/2002 | Scarrott et al. |
| 6,341,718 B1 | 1/2002 | Schilthuizen et al. |
| 6,349,856 B1 | 2/2002 | Chastel |
| 6,352,152 B1 | 3/2002 | Anderson et al. |
| 6,352,181 B1 | 3/2002 | Eberhard et al. |
| 6,363,932 B1 | 4/2002 | Forchione et al. |
| 6,375,048 B1 | 4/2002 | van der Meer et al. |
| 6,392,962 B1 | 5/2002 | Wyatt |
| 6,395,331 B1 | 5/2002 | Yan et al. |
| 6,401,710 B1 | 6/2002 | Scheuch et al. |
| 6,401,987 B1 | 6/2002 | Oechsel et al. |
| 6,402,055 B1 | 6/2002 | Jaeger et al. |
| 6,405,872 B1 | 6/2002 | Ruther et al. |
| 6,412,659 B1 | 7/2002 | Kneer |
| 6,419,167 B1 | 7/2002 | Fuchs |
| 6,423,298 B2 | 7/2002 | McNamara et al. |
| 6,427,682 B1 | 8/2002 | Klimowicz et al. |
| 6,446,054 B1 | 9/2002 | Mayorga Lopez |
| 6,457,658 B2 | 10/2002 | Srinath et al. |
| 6,464,108 B2 | 10/2002 | Corba |
| 6,481,435 B2 | 11/2002 | Hochrainer et al. |
| 6,491,897 B1 | 12/2002 | Freund et al. |
| 6,503,362 B1 | 1/2003 | Bartels et al. |
| 6,513,519 B2 | 2/2003 | Gallem |
| 6,543,448 B1 | 4/2003 | Smith et al. |
| 6,548,647 B2 | 4/2003 | Dietz et al. |
| 6,550,477 B1 | 4/2003 | Casper et al. |
| 6,565,743 B1 | 5/2003 | Poirier et al. |
| 6,578,741 B2 | 6/2003 | Ritsche et al. |
| 6,581,596 B1 | 6/2003 | Truitt et al. |
| 6,584,976 B2 | 7/2003 | Japuntich et al. |
| 6,606,990 B2 | 8/2003 | Stapleton et al. |
| 6,620,438 B2 | 9/2003 | Pairet et al. |
| 6,626,309 B1 | 9/2003 | Jansen et al. |
| 6,640,805 B2 | 11/2003 | Castro et al. |
| 6,641,782 B1 | 11/2003 | Mauchan et al. |
| 6,669,176 B2 | 12/2003 | Rock |
| 6,679,254 B1 | 1/2004 | Rand et al. |
| 6,685,691 B1 | 2/2004 | Freund et al. |
| 6,698,421 B2 | 3/2004 | Attolini |
| 6,706,726 B2 | 3/2004 | Meissner et al. |
| 6,708,846 B1 | 3/2004 | Fuchs et al. |
| 6,725,858 B2 | 4/2004 | Loescher |
| 6,729,328 B2 | 5/2004 | Goldemann |
| 6,732,731 B1 | 5/2004 | Tseng |
| 6,745,763 B2 | 6/2004 | Webb |
| 6,779,520 B2 | 8/2004 | Genova et al. |
| 6,789,702 B2 | 9/2004 | O'Connor et al. |
| 6,792,945 B2 | 9/2004 | Davies et al. |
| 6,823,862 B2 | 11/2004 | McNaughton |
| 6,825,441 B2 | 11/2004 | Katooka et al. |
| 6,846,413 B1 | 1/2005 | Kadel et al. |
| 6,866,039 B1 | 3/2005 | Wright et al. |
| 6,889,690 B2 | 5/2005 | Crowder et al. |
| 6,890,517 B2 | 5/2005 | Drechsel et al. |
| 6,915,901 B2 | 7/2005 | Feinberg et al. |
| 6,929,004 B1 | 8/2005 | Bonney et al. |
| 6,932,962 B1 | 8/2005 | Backstrom et al. |
| 6,942,127 B2 | 9/2005 | Raats |
| 6,964,759 B2 | 11/2005 | Lewis et al. |
| 6,977,042 B2 | 12/2005 | Kadel et al. |
| 6,978,916 B2 | 12/2005 | Smith |
| 6,986,346 B2 | 1/2006 | Hochrainer et al. |
| 6,988,496 B1 | 1/2006 | Eicher et al. |
| 6,994,083 B2 | 2/2006 | Foley et al. |
| 7,040,311 B2 | 5/2006 | Hochrainer et al. |

(56) References Cited

U.S. PATENT DOCUMENTS

| | | |
|---|---|---|
| 7,066,408 B2 | 6/2006 | Sugimoto et al. |
| 7,090,093 B2 | 8/2006 | Hochrainer et al. |
| 7,131,441 B1 | 11/2006 | Keller et al. |
| 7,152,760 B1 | 12/2006 | Peabody |
| 7,258,716 B2 | 8/2007 | Shekarriz et al. |
| 7,314,187 B2 | 1/2008 | Hochrainer et al. |
| 7,331,340 B2 | 2/2008 | Barney |
| 7,341,208 B2 | 3/2008 | Peters et al. |
| 7,380,575 B2 | 6/2008 | Stricklin |
| 7,417,051 B2 | 8/2008 | Banholzer et al. |
| 7,451,876 B2 | 11/2008 | Bossi et al. |
| 7,470,422 B2 | 12/2008 | Freund et al. |
| 7,556,037 B2 | 7/2009 | Klein |
| 7,559,597 B2 | 7/2009 | Mori |
| 7,571,722 B2 | 8/2009 | Wuttke et al. |
| 7,575,003 B2 | 8/2009 | Rasmussen |
| 7,579,358 B2 | 8/2009 | Boeck et al. |
| 7,611,694 B2 | 11/2009 | Schmidt |
| 7,611,709 B2 | 11/2009 | Bassarab et al. |
| 7,621,266 B2 | 11/2009 | Kladders et al. |
| 7,645,383 B2 | 1/2010 | Kadel et al. |
| 7,652,030 B2 | 1/2010 | Moesgaard et al. |
| 7,665,461 B2 | 2/2010 | Zierenberg et al. |
| 7,681,811 B2 | 3/2010 | Geser et al. |
| 7,686,014 B2 | 3/2010 | Boehm et al. |
| 7,717,299 B2 | 5/2010 | Greiner-Perth |
| 7,723,306 B2 | 5/2010 | Bassarab et al. |
| 7,743,945 B2 | 6/2010 | Lu et al. |
| 7,779,838 B2 | 8/2010 | Hetzer et al. |
| 7,802,568 B2 | 9/2010 | Eicher et al. |
| 7,819,342 B2 | 10/2010 | Spallek et al. |
| 7,823,584 B2 | 11/2010 | Geser et al. |
| 7,837,235 B2 | 11/2010 | Geser et al. |
| 7,849,851 B2 | 12/2010 | Zierenberg et al. |
| 7,896,264 B2 | 3/2011 | Eicher et al. |
| 7,980,243 B2 | 7/2011 | Hochrainer |
| 7,994,188 B2 | 8/2011 | Disse |
| 8,062,626 B2 | 11/2011 | Freund et al. |
| 8,104,643 B2 | 1/2012 | Pruvot |
| 8,167,171 B2 | 5/2012 | Moretti |
| 8,298,622 B2 | 10/2012 | Nakayama |
| 8,479,725 B2 | 7/2013 | Hausmann et al. |
| 8,495,901 B2 | 7/2013 | Hahn et al. |
| 8,650,840 B2 | 2/2014 | Holakovsky et al. |
| 8,651,338 B2 | 2/2014 | Leak et al. |
| 8,656,910 B2 | 2/2014 | Boeck et al. |
| 8,733,341 B2 | 5/2014 | Boeck et al. |
| 8,734,392 B2 | 5/2014 | Stadelhofer |
| 8,944,292 B2 | 2/2015 | Moreau |
| 8,950,393 B2 | 2/2015 | Holakovsky et al. |
| 8,960,188 B2 | 2/2015 | Bach et al. |
| 8,997,735 B2 | 4/2015 | Zierenberg et al. |
| 9,027,854 B2 | 5/2015 | Moser et al. |
| 9,192,734 B2 | 11/2015 | Hausmann et al. |
| 9,238,031 B2 | 1/2016 | Schmelzer et al. |
| 9,744,313 B2 | 8/2017 | Besseler |
| 9,827,384 B2 | 11/2017 | Holakovsky |
| 10,004,857 B2 * | 6/2018 | Besseler .......... A61M 15/0071 |
| 2001/0008632 A1 | 7/2001 | Freund et al. |
| 2001/0028308 A1 | 10/2001 | De La Huerga |
| 2001/0032643 A1 | 10/2001 | Hochrainer et al. |
| 2001/0035182 A1 | 11/2001 | Rubin et al. |
| 2002/0000225 A1 | 1/2002 | Schuler et al. |
| 2002/0005195 A1 | 1/2002 | Shick et al. |
| 2002/0007155 A1 | 1/2002 | Freund et al. |
| 2002/0046751 A1 | 4/2002 | MacRae et al. |
| 2002/0053344 A1 | 5/2002 | Davies |
| 2002/0060255 A1 | 5/2002 | Benoist |
| 2002/0074429 A1 | 6/2002 | Hettrich et al. |
| 2002/0079285 A1 | 6/2002 | Jansen et al. |
| 2002/0092523 A1 | 7/2002 | Connelly et al. |
| 2002/0111363 A1 | 8/2002 | Drechsel et al. |
| 2002/0129812 A1 | 9/2002 | Litherland et al. |
| 2002/0130195 A1 | 9/2002 | Jaeger |
| 2002/0137764 A1 | 9/2002 | Drechsel et al. |
| 2002/0176788 A1 | 11/2002 | Moutafis et al. |
| 2003/0039915 A1 | 2/2003 | Holt et al. |
| 2003/0064032 A1 | 4/2003 | Lamche et al. |
| 2003/0066524 A1 | 4/2003 | Hochrainer et al. |
| 2003/0066815 A1 | 4/2003 | Lucas |
| 2003/0080210 A1 | 5/2003 | Jaeger |
| 2003/0085254 A1 | 5/2003 | Katooka et al. |
| 2003/0098023 A1 | 5/2003 | Drachmann et al. |
| 2003/0106827 A1 | 6/2003 | Cheu et al. |
| 2003/0145849 A1 | 8/2003 | Drinan et al. |
| 2003/0178020 A1 | 9/2003 | Scarrott |
| 2003/0181478 A1 | 9/2003 | Drechsel et al. |
| 2003/0183225 A1 | 10/2003 | Knudsen |
| 2003/0187387 A1 | 10/2003 | Wirt et al. |
| 2003/0191151 A1 | 10/2003 | Chaudry et al. |
| 2003/0194379 A1 | 10/2003 | Brugger et al. |
| 2003/0196660 A1 | 10/2003 | Haveri |
| 2003/0209238 A1 | 11/2003 | Peters et al. |
| 2003/0226907 A1 | 12/2003 | Geser et al. |
| 2004/0004138 A1 | 1/2004 | Hettrich et al. |
| 2004/0010239 A1 | 1/2004 | Hochrainer et al. |
| 2004/0015126 A1 | 1/2004 | Zierenberg et al. |
| 2004/0019073 A1 | 1/2004 | Drechsel et al. |
| 2004/0055907 A1 | 3/2004 | Marco |
| 2004/0060476 A1 | 4/2004 | Sirejacob |
| 2004/0069799 A1 | 4/2004 | Gee et al. |
| 2004/0092428 A1 | 5/2004 | Chen et al. |
| 2004/0094147 A1 | 5/2004 | Schyra |
| 2004/0134494 A1 | 7/2004 | Papania et al. |
| 2004/0134824 A1 | 7/2004 | Chan et al. |
| 2004/0139700 A1 | 7/2004 | Powell et al. |
| 2004/0143235 A1 | 7/2004 | Freund et al. |
| 2004/0164186 A1 | 8/2004 | Kladders |
| 2004/0166065 A1 | 8/2004 | Schmidt |
| 2004/0182867 A1 | 9/2004 | Hochrainer et al. |
| 2004/0184994 A1 | 9/2004 | DeStefano et al. |
| 2004/0194524 A1 | 10/2004 | Jentzsch |
| 2004/0210199 A1 | 10/2004 | Atterbury et al. |
| 2004/0231667 A1 | 11/2004 | Horton et al. |
| 2005/0028812 A1 | 2/2005 | Djupesland |
| 2005/0028815 A1 | 2/2005 | Deaton et al. |
| 2005/0028816 A1 | 2/2005 | Fishman et al. |
| 2005/0061314 A1 | 3/2005 | Davies et al. |
| 2005/0089478 A1 | 4/2005 | Govind et al. |
| 2005/0098172 A1 | 5/2005 | Anderson |
| 2005/0126469 A1 | 6/2005 | Lu |
| 2005/0131357 A1 | 6/2005 | Denton et al. |
| 2005/0158394 A1 | 7/2005 | Staniforth et al. |
| 2005/0159441 A1 | 7/2005 | Hochrainer et al. |
| 2005/0183718 A1 | 8/2005 | Wuttke et al. |
| 2005/0191246 A1 | 9/2005 | Bechtold-Peters et al. |
| 2005/0194472 A1 | 9/2005 | Geser et al. |
| 2005/0239778 A1 | 10/2005 | Konetzki et al. |
| 2005/0247305 A1 | 11/2005 | Zierenberg et al. |
| 2005/0250704 A1 | 11/2005 | Bassarab et al. |
| 2005/0250705 A1 | 11/2005 | Bassarab et al. |
| 2005/0255119 A1 | 11/2005 | Bassarab et al. |
| 2005/0263618 A1 | 12/2005 | Spallek et al. |
| 2005/0268905 A1 | 12/2005 | Rasmussen |
| 2005/0268909 A1 | 12/2005 | Bonney et al. |
| 2005/0268915 A1 | 12/2005 | Wassenaar et al. |
| 2005/0269359 A1 | 12/2005 | Raats |
| 2006/0002863 A1 | 1/2006 | Schmelzer et al. |
| 2006/0016449 A1 | 1/2006 | Eicher et al. |
| 2006/0035874 A1 | 2/2006 | Lulla et al. |
| 2006/0037612 A1 | 2/2006 | Herder et al. |
| 2006/0067952 A1 | 3/2006 | Chen |
| 2006/0086828 A1 | 4/2006 | Bougamont et al. |
| 2006/0150971 A1 | 7/2006 | Lee et al. |
| 2006/0196500 A1 | 9/2006 | Hochrainer et al. |
| 2006/0225734 A1 | 10/2006 | Sagaser et al. |
| 2006/0239886 A1 | 10/2006 | Nakayama |
| 2006/0239930 A1 | 10/2006 | Lamche et al. |
| 2006/0254579 A1 | 11/2006 | Grychowski et al. |
| 2006/0279588 A1 | 12/2006 | Yearworth et al. |
| 2006/0282045 A1 | 12/2006 | Wilkinson et al. |
| 2006/0285987 A1 | 12/2006 | Jaeger et al. |
| 2006/0289002 A1 | 12/2006 | Hetzer et al. |
| 2006/0293293 A1 | 12/2006 | Muller et al. |

(56) References Cited

U.S. PATENT DOCUMENTS

| | | | |
|---|---|---|---|
| 2007/0062518 A1* | 3/2007 | Geser | A61M 15/004 128/200.14 |
| 2007/0062519 A1 | 3/2007 | Wuttke et al. | |
| 2007/0062979 A1 | 3/2007 | Dunne | |
| 2007/0090205 A1 | 4/2007 | Kunze et al. | |
| 2007/0090576 A1 | 4/2007 | Geser et al. | |
| 2007/0107720 A1 | 5/2007 | Boeck | |
| 2007/0119449 A1 | 5/2007 | Boehm et al. | |
| 2007/0137643 A1 | 6/2007 | Bonney et al. | |
| 2007/0163574 A1 | 7/2007 | Rohrschneider et al. | |
| 2007/0181526 A1 | 8/2007 | Frishman | |
| 2007/0183982 A1 | 8/2007 | Berkel et al. | |
| 2007/0210121 A1 | 9/2007 | Stadelhofer et al. | |
| 2007/0221211 A1 | 9/2007 | Sagalovich | |
| 2007/0264437 A1 | 11/2007 | Zimmermann | |
| 2007/0272763 A1 | 11/2007 | Dunne et al. | |
| 2007/0298116 A1 | 12/2007 | Bechtold-Peters et al. | |
| 2008/0017192 A1 | 1/2008 | Southby et al. | |
| 2008/0029085 A1 | 2/2008 | Lawrence et al. | |
| 2008/0060640 A1 | 3/2008 | Waldner et al. | |
| 2008/0083408 A1 | 4/2008 | Hodson et al. | |
| 2008/0092885 A1 | 4/2008 | von Schuckmann | |
| 2008/0156321 A1 | 7/2008 | Bowman | |
| 2008/0163869 A1 | 7/2008 | Nobutani | |
| 2008/0164275 A1 | 7/2008 | Poutiatine | |
| 2008/0197045 A1 | 8/2008 | Metzger et al. | |
| 2008/0249459 A1 | 10/2008 | Godfrey et al. | |
| 2008/0264412 A1 | 10/2008 | Meyer et al. | |
| 2008/0265198 A1 | 10/2008 | Warby | |
| 2008/0283553 A1 | 11/2008 | Cox et al. | |
| 2008/0299049 A1 | 12/2008 | Stangl | |
| 2008/0308580 A1 | 12/2008 | Gaydos et al. | |
| 2009/0032427 A1 | 2/2009 | Cheu et al. | |
| 2009/0060764 A1 | 3/2009 | Mitzlaff et al. | |
| 2009/0075990 A1 | 3/2009 | Schmidt | |
| 2009/0114215 A1 | 5/2009 | Boeck et al. | |
| 2009/0166379 A1 | 7/2009 | Wright et al. | |
| 2009/0170839 A1 | 7/2009 | Schmidt | |
| 2009/0185983 A1 | 7/2009 | Freund et al. | |
| 2009/0197841 A1 | 8/2009 | Kreher et al. | |
| 2009/0202447 A1 | 8/2009 | Kreher et al. | |
| 2009/0211576 A1 | 8/2009 | Lehtonen et al. | |
| 2009/0221626 A1 | 9/2009 | Schmidt | |
| 2009/0235924 A1 | 9/2009 | Holakovsky et al. | |
| 2009/0272664 A1 | 11/2009 | Marshall et al. | |
| 2009/0293870 A1 | 12/2009 | Brunnberg | |
| 2009/0306065 A1 | 12/2009 | Schmidt | |
| 2009/0308772 A1 | 12/2009 | Abrams | |
| 2009/0314287 A1 | 12/2009 | Spallek et al. | |
| 2009/0317337 A1 | 12/2009 | Schmidt | |
| 2010/0012120 A1 | 1/2010 | Herder | |
| 2010/0018524 A1 | 1/2010 | Jinks et al. | |
| 2010/0018997 A1 | 1/2010 | Faneca Llesera | |
| 2010/0044393 A1 | 2/2010 | Moretti | |
| 2010/0056559 A1 | 3/2010 | Schmelzer et al. | |
| 2010/0084531 A1 | 4/2010 | Schuchman | |
| 2010/0095957 A1 | 4/2010 | Corbacho | |
| 2010/0144784 A1 | 6/2010 | Schmelzer et al. | |
| 2010/0168710 A1 | 7/2010 | Braithwaite | |
| 2010/0237102 A1 | 9/2010 | Margheritis | |
| 2010/0242557 A1 | 9/2010 | Spreitzer et al. | |
| 2010/0242954 A1 | 9/2010 | Hahn et al. | |
| 2010/0313884 A1 | 12/2010 | Elliman | |
| 2010/0331765 A1 | 12/2010 | Sullivan | |
| 2011/0005517 A1 | 1/2011 | Boeck et al. | |
| 2011/0011393 A1 | 1/2011 | Geser | |
| 2011/0041842 A1 | 2/2011 | Bradshaw | |
| 2011/0168175 A1 | 7/2011 | Dunne et al. | |
| 2011/0239594 A1 | 10/2011 | Nottingham et al. | |
| 2011/0245780 A1 | 10/2011 | Helmer et al. | |
| 2011/0268668 A1 | 11/2011 | Lamche et al. | |
| 2011/0277753 A1 | 11/2011 | Dunne et al. | |
| 2011/0290239 A1 | 12/2011 | Bach | |
| 2011/0290242 A1 | 12/2011 | Bach et al. | |
| 2011/0290243 A1 | 12/2011 | Bach et al. | |
| 2012/0090603 A1 | 4/2012 | Dunne et al. | |
| 2012/0132199 A1 | 5/2012 | Kiesewetter | |
| 2012/0138049 A1 | 6/2012 | Wachtel | |
| 2012/0138713 A1 | 6/2012 | Schuy et al. | |
| 2012/0260913 A1 | 10/2012 | Bach et al. | |
| 2012/0325204 A1 | 12/2012 | Holakovsky et al. | |
| 2013/0012908 A1 | 1/2013 | Yeung | |
| 2013/0056888 A1* | 3/2013 | Holakovsky | A61M 11/08 261/78.2 |
| 2013/0125880 A1* | 5/2013 | Holakovsky | A61M 15/008 128/200.21 |
| 2013/0125881 A1 | 5/2013 | Holakovsky | |
| 2013/0126389 A1 | 5/2013 | Holakovsky et al. | |
| 2013/0206136 A1 | 8/2013 | Herrmann et al. | |
| 2013/0269687 A1 | 10/2013 | Bessler et al. | |
| 2014/0121234 A1 | 5/2014 | Kreher et al. | |
| 2014/0190472 A1 | 7/2014 | Holakovsky et al. | |
| 2014/0228397 A1 | 8/2014 | Schmelzer et al. | |
| 2014/0331994 A1 | 11/2014 | Holakovsky et al. | |
| 2015/0040890 A1 | 2/2015 | Bessler et al. | |
| 2015/0040893 A1 | 2/2015 | Besseler | |
| 2015/0041558 A1 | 2/2015 | Bessler et al. | |
| 2015/0114387 A1 | 4/2015 | Bach et al. | |
| 2015/0122247 A1 | 5/2015 | Besseler et al. | |
| 2015/0258021 A1 | 9/2015 | Kreher et al. | |
| 2015/0300687 A1 | 10/2015 | Schmelzer et al. | |
| 2015/0320947 A1 | 11/2015 | Eicher et al. | |
| 2015/0320948 A1 | 11/2015 | Eicher et al. | |
| 2015/0352298 A1 | 12/2015 | Egerstrom | |
| 2016/0095992 A1 | 4/2016 | Wachtel | |

FOREIGN PATENT DOCUMENTS

| | | |
|---|---|---|
| CA | 2233981 A1 | 4/1997 |
| CA | 2237853 A1 | 6/1997 |
| CA | 2225826 A1 | 10/1997 |
| CA | 2275392 A1 | 7/1998 |
| CA | 2297174 A1 | 2/1999 |
| CA | 2343123 A1 | 4/2000 |
| CA | 2434872 A1 | 8/2002 |
| CA | 2497059 A1 | 3/2004 |
| CA | 2497680 A1 | 3/2004 |
| CA | 2513167 A1 | 10/2004 |
| CA | 2557020 A1 | 9/2005 |
| CA | 2653183 A1 | 12/2007 |
| CA | 2653422 A1 | 12/2007 |
| CN | 1125426 A | 6/1996 |
| CN | 1849174 A | 10/2006 |
| CN | 101247897 A | 8/2008 |
| DE | 1653651 A1 | 7/1971 |
| DE | 2754100 A1 | 6/1978 |
| DE | 4117078 A1 | 11/1992 |
| DE | 19625027 A1 | 1/1997 |
| DE | 19615422 A1 | 11/1997 |
| DE | 19653969 A1 | 6/1998 |
| DE | 1992844 C1 | 11/1999 |
| DE | 10007591 A1 | 11/2000 |
| DE | 10104367 A1 | 8/2002 |
| DE | 10300983 A1 | 7/2004 |
| DE | 102004031673 A1 | 1/2006 |
| DE | 202006017793 U1 | 1/2007 |
| DE | 01102006025871 A1 | 12/2007 |
| DK | 83175 C | 7/1957 |
| DK | 140801 B | 11/1979 |
| EP | 0018609 A1 | 11/1980 |
| EP | 0289332 A1 | 11/1988 |
| EP | 0289336 A1 | 11/1988 |
| EP | 0354507 A2 | 2/1990 |
| EP | 0364235 A1 | 4/1990 |
| EP | 0372777 A2 | 6/1990 |
| EP | 0386800 A1 | 9/1990 |
| EP | 0412524 A1 | 2/1991 |
| EP | 0505123 A1 | 9/1992 |
| EP | 0520571 A1 | 12/1992 |
| EP | 0622311 A2 | 11/1994 |
| EP | 0642992 A2 | 3/1995 |
| EP | 0679443 A1 | 11/1995 |
| EP | 0845265 A1 | 6/1996 |
| EP | 0735048 A1 | 10/1996 |

(56) References Cited

FOREIGN PATENT DOCUMENTS

| | | |
|---|---|---|
| EP | 0811430 A1 | 3/1997 |
| EP | 0778221 A1 | 6/1997 |
| EP | 0845253 A2 | 6/1998 |
| EP | 0860210 A2 | 8/1998 |
| EP | 0916428 A2 | 5/1999 |
| EP | 0965355 A2 | 12/1999 |
| EP | 0970751 A2 | 1/2000 |
| EP | 1003478 A1 | 5/2000 |
| EP | 1017469 A1 | 7/2000 |
| EP | 1025923 A1 | 8/2000 |
| EP | 1068906 A2 | 1/2001 |
| EP | 1075875 A2 | 2/2001 |
| EP | 1092447 A2 | 4/2001 |
| EP | 1157689 A1 | 11/2001 |
| EP | 1211628 A2 | 6/2002 |
| EP | 1245244 A2 | 10/2002 |
| EP | 1312418 A2 | 5/2003 |
| EP | 1375385 A2 | 1/2004 |
| EP | 1521609 A2 | 4/2005 |
| EP | 1535643 Z1 | 6/2005 |
| EP | 1595564 A1 | 11/2005 |
| EP | 1595822 A1 | 11/2005 |
| EP | 1726324 A1 | 11/2006 |
| EP | 1736193 A1 | 12/2006 |
| EP | 1795221 A1 | 6/2007 |
| EP | 1813548 A1 | 8/2007 |
| EP | 2135632 A1 | 8/2007 |
| EP | 2614848 A1 | 7/2013 |
| ES | 2262348 T3 | 11/2006 |
| FR | 2505688 A1 | 11/1982 |
| FR | 2604363 A1 | 4/1988 |
| FR | 2673608 A1 | 9/1992 |
| FR | 2756502 A1 | 6/1998 |
| GB | 1524431 A | 9/1976 |
| GB | 2081396 A | 2/1982 |
| GB | 2101020 A | 1/1983 |
| GB | 2279273 A | 1/1995 |
| GB | 2291135 A | 1/1996 |
| GB | 2332372 A | 6/1999 |
| GB | 2333129 A | 7/1999 |
| GB | 2347870 A | 9/2000 |
| GB | 2355252 A | 4/2001 |
| GB | 2398253 A | 8/2004 |
| GB | 0700839.4 | 7/2008 |
| JP | S5684246 A | 7/1981 |
| JP | H01288265 A | 11/1989 |
| JP | H0228121 A | 1/1990 |
| JP | H057246 | 2/1993 |
| JP | H0553470 A | 3/1993 |
| JP | H06312019 A | 11/1994 |
| JP | H07118164 A | 5/1995 |
| JP | H07118166 A | 5/1995 |
| JP | 07323086 A | 12/1995 |
| JP | H08277226 A | 10/1996 |
| JP | H092442 A | 1/1997 |
| JP | H0977073 A | 3/1997 |
| JP | H09315953 A | 12/1997 |
| JP | 2001518428 A | 10/2001 |
| JP | 2001346878 A | 12/2001 |
| JP | 2002504411 A | 2/2002 |
| JP | 2002235940 A | 8/2002 |
| JP | 2003511212 A | 3/2003 |
| JP | 2003299717 A | 10/2003 |
| JP | 2004502502 A | 1/2004 |
| JP | 2004097617 A | 4/2004 |
| JP | 2005511210 A | 4/2005 |
| JP | 2005144459 A | 6/2005 |
| JP | 2006505374 A | 2/2006 |
| JP | 2007517529 A | 7/2007 |
| JP | 2007245144 A | 9/2007 |
| JP | 2007534379 A | 11/2007 |
| JP | 2008119489 A | 5/2008 |
| JP | 2008541806 A | 11/2008 |
| JP | 2010526620 A | 8/2010 |
| JP | 2010540371 A | 12/2010 |
| WO | 198100674 A1 | 3/1981 |
| WO | 198200785 A1 | 3/1982 |
| WO | 198300288 A1 | 2/1983 |
| WO | 198303054 A1 | 9/1983 |
| WO | 198605419 A1 | 9/1986 |
| WO | 198706137 A1 | 10/1987 |
| WO | 198803419 A1 | 5/1988 |
| WO | 198900889 A1 | 2/1989 |
| WO | 198900947 A1 | 2/1989 |
| WO | 198902279 A1 | 3/1989 |
| WO | 198903672 A1 | 5/1989 |
| WO | 198903673 A1 | 5/1989 |
| WO | 198905139 A1 | 6/1989 |
| WO | 199009780 A1 | 9/1990 |
| WO | 199009781 A1 | 9/1990 |
| WO | 1991014468 A1 | 10/1991 |
| WO | 199206704 A1 | 4/1992 |
| WO | 199217231 A1 | 10/1992 |
| WO | 199221332 A1 | 12/1992 |
| WO | 199222286 | 12/1992 |
| WO | 1993013737 A1 | 7/1993 |
| WO | 199325321 A1 | 12/1993 |
| WO | 1993024164 A1 | 12/1993 |
| WO | 1994007607 A1 | 4/1994 |
| WO | 199417822 A1 | 8/1994 |
| WO | 199425371 A1 | 11/1994 |
| WO | 199427653 A2 | 12/1994 |
| WO | 199503034 A1 | 2/1995 |
| WO | 1995032015 A1 | 11/1995 |
| WO | 199600050 A1 | 1/1996 |
| WO | 1996006011 A2 | 2/1996 |
| WO | 199606581 A1 | 3/1996 |
| WO | 199623522 A1 | 8/1996 |
| WO | 199701329 A1 | 1/1997 |
| WO | 199706813 A1 | 2/1997 |
| WO | 199706842 A1 | 2/1997 |
| WO | 199712683 A1 | 4/1997 |
| WO | 1997012687 A1 | 4/1997 |
| WO | 199720590 A1 | 6/1997 |
| WO | 199723208 A1 | 7/1997 |
| WO | 199727804 A1 | 8/1997 |
| WO | 199735562 A1 | 10/1997 |
| WO | 199741833 A1 | 11/1997 |
| WO | 1998012511 A2 | 3/1998 |
| WO | 199827959 A2 | 7/1998 |
| WO | 199831346 A1 | 7/1998 |
| WO | 199839043 A1 | 9/1998 |
| WO | 1999001227 A1 | 1/1999 |
| WO | 1999007340 A1 | 2/1999 |
| WO | 1999011563 A1 | 3/1999 |
| WO | 1999016530 A1 | 4/1999 |
| WO | 1999043571 A1 | 9/1999 |
| WO | 19965464 | 12/1999 |
| WO | 199962495 A2 | 12/1999 |
| WO | 200001612 A2 | 1/2000 |
| WO | 200023037 A1 | 4/2000 |
| WO | 2000023065 A2 | 4/2000 |
| WO | 200027543 A1 | 5/2000 |
| WO | 200037336 A1 | 6/2000 |
| WO | 2000033965 A1 | 6/2000 |
| WO | 200049988 A2 | 8/2000 |
| WO | 200064779 A1 | 11/2000 |
| WO | 200113885 A1 | 3/2001 |
| WO | 200128489 A1 | 4/2001 |
| WO | 2001064182 A2 | 9/2001 |
| WO | 200187392 A1 | 11/2001 |
| WO | 2001085097 A1 | 11/2001 |
| WO | 200197888 A2 | 12/2001 |
| WO | 200198175 A1 | 12/2001 |
| WO | 200198176 A2 | 12/2001 |
| WO | 200204054 A1 | 1/2002 |
| WO | 200205879 A1 | 1/2002 |
| WO | 200217988 A2 | 3/2002 |
| WO | 200232899 A1 | 4/2002 |
| WO | 2002034411 A1 | 5/2002 |
| WO | 2002070141 A1 | 9/2002 |
| WO | 2002089887 A1 | 11/2002 |
| WO | 2003002045 A1 | 1/2003 |
| WO | 2003014832 A1 | 2/2003 |

(56) References Cited

FOREIGN PATENT DOCUMENTS

| | | |
|---|---|---|
| WO | 2003020253 A2 | 3/2003 |
| WO | 2003022332 A2 | 3/2003 |
| WO | 200307159 A2 | 5/2003 |
| WO | 2003035030 A1 | 5/2003 |
| WO | 2003037259 A2 | 5/2003 |
| WO | 2003049786 A2 | 6/2003 |
| WO | 2003050031 A1 | 6/2003 |
| WO | 2003053350 A2 | 7/2003 |
| WO | 2003057593 A1 | 7/2003 |
| WO | 2003059547 A1 | 7/2003 |
| WO | 2003068299 A1 | 8/2003 |
| WO | 2003087097 A1 | 10/2003 |
| WO | 2003097139 A1 | 11/2003 |
| WO | 2004019985 A1 | 3/2004 |
| WO | 2004022052 A1 | 3/2004 |
| WO | 2004022132 A2 | 3/2004 |
| WO | 2004022244 A1 | 3/2004 |
| WO | 2004024157 A1 | 3/2004 |
| WO | 200433954 A2 | 4/2004 |
| WO | 2004041334 A2 | 5/2004 |
| WO | 2004062813 A1 | 7/2004 |
| WO | 2004078236 A2 | 9/2004 |
| WO | 2004089551 A2 | 10/2004 |
| WO | 2004091704 A1 | 10/2004 |
| WO | 2004098689 A1 | 11/2004 |
| WO | 2004098795 A1 | 11/2004 |
| WO | 2005000476 A1 | 1/2005 |
| WO | 2005004844 A1 | 1/2005 |
| WO | 2005014175 A1 | 2/2005 |
| WO | 2005020953 A1 | 3/2005 |
| WO | 2005030211 A1 | 4/2005 |
| WO | 2005055976 A2 | 6/2005 |
| WO | 2005077445 A1 | 8/2005 |
| WO | 2005079997 A1 | 9/2005 |
| WO | 2005080001 A1 | 9/2005 |
| WO | 2005080002 A1 | 9/2005 |
| WO | 2005087299 A1 | 9/2005 |
| WO | 2005107837 A1 | 11/2005 |
| WO | 2005109948 A2 | 11/2005 |
| WO | 2005112892 A1 | 12/2005 |
| WO | 2005112996 A1 | 12/2005 |
| WO | 2005113007 A2 | 12/2005 |
| WO | 2006011638 A1 | 2/2006 |
| WO | 2006018392 A1 | 2/2006 |
| WO | 2006027595 A1 | 3/2006 |
| WO | 2006037636 A2 | 4/2006 |
| WO | 2006037948 A2 | 4/2006 |
| WO | 2006042297 A2 | 4/2006 |
| WO | 2006045813 A1 | 5/2006 |
| WO | 2006110080 A1 | 10/2006 |
| WO | 2006125577 A2 | 11/2006 |
| WO | 2006126014 A2 | 11/2006 |
| WO | 2007011475 A1 | 1/2007 |
| WO | 2007022898 A2 | 3/2007 |
| WO | 2007030162 A2 | 3/2007 |
| WO | 2007049239 A2 | 5/2007 |
| WO | 2007060104 A2 | 5/2007 |
| WO | 2007060105 A1 | 5/2007 |
| WO | 2007060106 A1 | 5/2007 |
| WO | 2007060107 A1 | 5/2007 |
| WO | 2007060108 A2 | 5/2007 |
| WO | 2007062721 A1 | 6/2007 |
| WO | 2007090822 A2 | 8/2007 |
| WO | 2007101557 A2 | 9/2007 |
| WO | 2007128381 A1 | 11/2007 |
| WO | 2007134965 A1 | 11/2007 |
| WO | 2007134966 A1 | 11/2007 |
| WO | 2007134967 A1 | 11/2007 |
| WO | 2007134968 A1 | 11/2007 |
| WO | 2007141201 A1 | 12/2007 |
| WO | 2007141203 A1 | 12/2007 |
| WO | 2008023017 A2 | 2/2008 |
| WO | 2008047035 A2 | 4/2008 |
| WO | 2008077623 A1 | 7/2008 |
| WO | 2008124666 A2 | 10/2008 |
| WO | 2008138936 A2 | 11/2008 |
| WO | 2008146025 A2 | 12/2008 |
| WO | 2009006137 A1 | 1/2009 |
| WO | 2009047021 A1 | 4/2009 |
| WO | 2009047173 A2 | 4/2009 |
| WO | 2009050978 A1 | 4/2009 |
| WO | 2009090245 A1 | 7/2009 |
| WO | 2009103510 A1 | 8/2009 |
| WO | 2009115200 A1 | 9/2009 |
| WO | 2010005946 A2 | 1/2010 |
| WO | 2010006870 A1 | 1/2010 |
| WO | 2010094305 A1 | 8/2010 |
| WO | 2010094413 A2 | 8/2010 |
| WO | 2010112358 A2 | 10/2010 |
| WO | 2010133294 A2 | 11/2010 |
| WO | 2010149280 A1 | 12/2010 |
| WO | 2011006711 A1 | 1/2011 |
| WO | 2011064160 A1 | 6/2011 |
| WO | 2011064163 A1 | 6/2011 |
| WO | 2011064164 A1 | 6/2011 |
| WO | 2011131779 A1 | 10/2011 |
| WO | 2011154295 A2 | 12/2011 |
| WO | 2011160932 A1 | 12/2011 |
| WO | 2012130757 A1 | 10/2012 |
| WO | 2012159914 A1 | 11/2012 |
| WO | 2012160047 A2 | 11/2012 |
| WO | 2012160052 A1 | 11/2012 |
| WO | 2012161685 A1 | 11/2012 |
| WO | 2012162305 A1 | 11/2012 |
| WO | 2013107640 A1 | 7/2013 |
| WO | 2013110601 A1 | 8/2013 |
| WO | 2013152861 A1 | 10/2013 |
| WO | 2013152894 A1 | 10/2013 |
| WO | 2014111370 A1 | 7/2014 |
| WO | 2015018901 A1 | 2/2015 |
| WO | 2015018903 A1 | 2/2015 |
| WO | 2015018904 A1 | 2/2015 |
| WO | 2015169431 A2 | 11/2015 |
| WO | 2015169732 A1 | 11/2015 |
| ZA | 199901520 A | 12/1999 |

OTHER PUBLICATIONS

International Search Report and Written Opinion for PCT/EP2005/001947, 11 pages, dated May 19, 2005.
International Search Report and Written Opinion for PCT/EP2005/004792, 19 pages, dated Aug. 4, 201.
International Search Report and Written Opinion for PCT/EP2005/055560, 13 pages, dated Mar. 2, 2006.
International Search Report and Written Opinion for PCT/EP2006/068399, 8 pages, dated on Jun. 25, 2007.
International Search Report and Written Opinion for PCT/EP2006/068395, 8 pages, dated Jun. 25, 2007.
International Search Report and Written Opinion for PCT/EP2006/068396, 11 pages, dated Apr. 23, 2007.
International Search Report and Written Opinion for PCT/EP2006/068397, 13 pages, dated Feb. 21, 2007.
International Search Report and Written Opinion for PCT/EP2006/068398, 10 pages, dated May 10, 2007.
International Search Report and Written Opinion for PCT/EP2007/001558, 13 pages, dated Sep. 28, 2007.
International Search Report and Written Opinion for PCT/EP2007/054488, 11 pages, dated Jul. 18, 2007.
International Search Report and Written Opinion for PCT/EP2007/054490, 11 pages, dated Jul. 17, 2007.
International Search Report and Written Opinion for PCT/EP2007/054492, 13 pages, dated Aug. 16, 2007.
International Search Report and Written Opinion for PCT/EP2007/055381, 14 pages, dated Sep. 3, 2007.
International Search Report and Written Opinion for PCT/EP2007/055383, 18 pages, dated Sep. 27, 2007.
International Search Report and Written Opinion for PCT/EP2009/001619, 6 pages, dated Jun. 10, 2009.
International Search Report and Written Opinion for PCT/EP2009/005949, 8 pages, dated Jan. 20, 2010.

(56) References Cited

OTHER PUBLICATIONS

International Search Report and Written Opinion for PCT/EP2010/057937, 1 pages, dated Jul. 20, 2010.
International Search Report and Written Opinion for PCT/EP2010/067896, 14 pages, dated Apr. 13, 2011.
International Search Report and Written Opinion for PCT/EP2010/067901, 12 pages, dated Apr. 14, 2011.
International Search Report and Written Opinion for PCT/EP2010/067902, 10 pages, dated May 2, 2011.
International Search Report and Written Opinion for PCT/EP2012/058905, 12 pages, dated Oct. 19, 2012.
International Search Report and Written Opinion for PCT/EP2012/059454, 16 pages, dated Jan. 14, 2013.
International Search Report and Written Opinion for PCT/EP2012/059463, 10 pages, dated Oct. 25, 2012.
International Search Report and Written Opinion for PCT/EP2013/001068, 9 pages, dated Jun. 5, 2013.
International Search Report and Written Opinion for PCT/EP2013/054324, 11 pages, dated Jun. 5, 2013.
International Search Report and Written Opinion for PCT/EP2014/067006, 15 pages, dated Nov. 24, 2014.
International Search Report and Written Opinion for PCT/EP2015/000903, 31 pages, dated Nov. 5, 2015.
International Search Report and Written Opinion for PCT/EP2015/059691, 22 pages, dated Oct. 8, 2015.
International Search Report and Written Opinion for corresponding PCT/EP2010/007961, 18 pages, dated Oct. 28, 2010.
International Search Report for PCT/EP199904803, 6 pages, dated Dec. 15, 1998.
International Search Report for PCT/EP1999/07589, 6 pages, dated Mar. 1, 2000.
International Search Report and Written Opinion for PCT/EP2007/003322, 13 pages, dated Aug. 17, 200.
International Search Report and Written Opinion for PCT/EP2007/054489, 12 pages, dated Feb. 10, 2007.
International Search Report and Written Opinion for PCT/EP2008/011112, 14 pages, dated Sep. 3, 2009.
International Search Report and Written Opinion for PCT/EP2008/055863, 25 pages, dated Dec. 19, 2008.
International Search Report and Written Opinion for PCT/EP2009/001153, 8 pages, dated May 20, 2009.
International Search Report and Written Opinion for PCT/EP2010/002740, 18 pages, dated Nov. 12, 2010.
International Search Report and Written Opinion for PCT/EP2010/053668, 11 pages, dated Nov. 8, 2010.
International Search Report and Written Opinion for PCT/EP2011/059088, 14 pages, dated Sep. 26, 2011.
International Search Report and Written Opinion for PCT/EP2012/055209, 10 pages, dated Jan. 6, 2012.
International Search Report and Written Opinion for PCT/EP2007/051095, 10 pages, dated Sep. 21, 2007.
Wall et al., "High levels of exopeptidase activity are present in rat and anine bronchoalveolar lavage fluid," International Journal of Pharmaceutics, vol. 97, Issue 1-3, pp. 171-181, (Jan. 1993).
International Search Report and Written Opinion for PCT/EP2014/067001 dated Sep. 9, 2014.
International Search Report and Written Opinion for PCT/EP2014/067004 dated Jan. 10, 2014.
"Activate". Collins English Dictionary, London; Collins, 2000, 2 pages. [Retrieved at http://search.credoreference.com/content/entry/hcengdict/activate/0 on Jun. 12, 2014].
"Lung Cancer". Merck Manual Home Edition, pp. 1-7. [Accessed at www.merck.com/mmhe/print/sec04/ch057/ch057a.html, on Jul. 28, 2010].
Abstract in English for DE19902844, 1999.
Abstract in English for DE4117078, 1992.
Abstract in English for EP0354507, 1990.
Abstract in English for FR2756502, 1998.
Abstract in English for JPS5684246, 1979.
Abstract in English of DE10007591, 2000.
Abstract in English of DE202006017793, 2007.
Abstract in English of FR2604363, Sep. 30, 1986.
Abstract in English of JPH0553470, 1993.
Abstract in English of JPH057246, 1993.
Abstract in English of JPH07118164, 1995.
Abstract in English of JPH07118166, 1995.
Abstract in English of JPH08277226, 1996.
Abstract in English of JPH092442, 1997.
Abstract in English of JPH09315953, 1997.
Abstract in English of JPH0977073, 1997.
Abstract in English of WO199706813, 1997.
Abstract in English of WO199839043, 1998.
Abstract in English of WO2002070141, 2002.
Ackermann et al.; Quantitative Online Detection of Low-Concentrted Drugs via a SERS Microfluidic System; ChemPhysChem; 2007; vol. 8; pp. 2665-2670.
Beasley R et al: "Preservatives in Nebulizer solutions; Risks without Benefit" Pharmacotherapy, Boston, US, Bd. 18, Nr 1, Jan. 1998.
Beasley R et al: "Preservatives in Nebulizer solutions: Risks without Benefit" Pharmacotherapy, Boston, US, Bd. 18, Nr. 1, Jan. 1998, pp. 130-139.
Bocci et al., "Pulmonary catabolism of interferons: alveolar absorption of 125l-labeled human interferon alpha is accompanied by partial loss of biologicall activity" Antiviral Research, vol. 4, 1984, pp. 211-220.
Chen, F-K et al., "A study of forming pressure in the tube-hydroforming process", Journal of Materials Processing Technology, 192-193, 2007, p. 404-409.
China Suppliers, Shanghai Life Chemical Technology Co., Ltd. Product details on polyvinylpyrrolidones. Obtained online by the USPTO examiner on Apr. 24, 2011.
Cras et al., "Comparison of chemical cleaning methods of glass in preparation for silanization". Biosensors & Bioelectronics, vol. 14, 1999, pp. 683-688.
Diamond et al., "Substance P Fails to Mimic Vagally Mediated Nonadrenergic Bronchodilation". Peptides, vol. 3, 1982, pp. 27-29.
Elwenspoek et al., "Silicon Micromachining", Chapter 3, Mechanical Microsensors, Springer-Verlang Berlin Heidelberg, 2001, 4 pages.
English Language Abstract of EP1068906, 2001.
Fuchs et al., "Meopterin, biochemistry and clinical use as a marker for cellular immune reactions". International Archives of Allergy and Immunology, vol. 101, No. 1, 1993, pp. 1-6, Abstract 1p.
Han et al.; Surface activation of thin silicon oxides by wet cleaninig and silanization; This Solid Films; 2006; vol. 510; No. 1-2; pp. 175-180.
Henkel et al.; Chip modules for generation and manipulation of fluid segments for micro serial flow processes; Chemical Engineering Journal; 2004; vol. 101; pp. 439-445.
Hoffmann et al., "Mixed self-assembled monolayers (SAMs) consisting of methoxy-tri(ethylene glycol)-terminated and alkyl-terminated dimethylchlorosilanes control the non-specific adsorption of proteins at oxidic sufaces". Journal of Colloid and Interface Science, vol. 295, 2006, pp. 427-435.
Husseini et al., "Alkyl Monolayers on Silica Surfaces Prepaid Using Neat, Heated Dimethylmonochlorosilanes with Low Vapor Pressures". Langmuir, vol. 19, 2003, pp. 5169-5171.
Ip et al., "Stability of Recombinant Consensus Interferon to Air-Jest and Ultrasonic Nebulization". Journal of Pharmaceutical Sciences, vol. 84, No. 10, Oct. 1995, pp. 1210-1214.
Jendle et al., "Intrapulmonary administration of insulin to healthy volunteers". Journal of Internal Medicine, vol. 240, 1996, pp. 93-98.
JP2005144459—English language abstract only.
Kutchoukov et al., "Fabrication of nanofluidic devices using glass-to-glass anodic bonding" Sensors and Actuators A, vol. 114, 2004, pp. 521-527.
Lougheed et al., "Insulin Aggregation in Artificial Delivery Systems". Diabetologia, vol. 19, 1980, pp. 1-9.
Mandal et al., "Cytophobic surface modification of microfluidic arrays for in situ parallel peptide synthesis and cell adhesion assays". Biotechnology Progress, vol. 23, No. 4, 2007, pp. 972-978 (Author Manuscript Available in PMC, Sep. 21, 2009, 19 pages).

(56) References Cited

OTHER PUBLICATIONS

Niven et al., "Some Factors Associated with the Ultrasonic Nebulization of Proteins". Pharmaceutical Research, vol. 12, No. 1, 1995, pp. 53-59.
Remington Pharmacy, Editor Alfonso R. Gennaro. 19th ed., Spanish Secondary Edition: Panamericana, Spain, 1995, Sciarra, J.J., "Aerosols", pp. 2560-2582. The English translation is from the 1995 English Primary Edition, Sciarra, J.J. , Chapter 95, R97-1185.
Trasch et al., "Performance data of refloquart Glucose in the Evaluation of Reflotron". Clinical Chemistry, vol. 30, 1984, p. 969 (abstract only).
Wall et al., "High levels of exopeptidase activity are present in rat canine bronchoalyeolar lavage fluid", International Journall of Pharmaceutics, vol. 97, Issue 1-3, pp. 171-181. 1993, Abstract pp. 1-2.
Wang et al.; Self-Assembled Silane Monolayers; Fabrication with Nanoscale Uniformity; Langmuir, 2005; vol. 21, No. 5; pp. 1846-1857.

\* cited by examiner

NEBULIZER

CROSS REFERENCE TO RELATED APPLICATIONS

This application is a continuation of U.S. patent application Ser. No. 15/942,737, accorded a filing date of Apr. 2, 2018, which is a continuation of U.S. patent application Ser. No. 14/453,805, accorded a filing date of Aug. 7, 2014 (issued U.S. Pat. No. 10,004,857 on Jun. 26, 2018), which claims priority to EP Application No. 13003987.8, filed Aug. 9, 2013, the entire disclosures of which are hereby incorporated by reference.

BACKGROUND

The present invention relates to a nebulizer for nebulizing a fluid.

WO 2006/125577 A2 discloses a nebulizer which comprises, as a reservoir for fluid which is to be atomized or nebulized, an insertable rigid container having an inner bag containing the fluid and a pressure generator with a drive spring for delivering and atomizing the fluid. The container is pre-installed in nebulizer in a delivery state. The pre-installed container is held by a transportation lock unmovable within the housing in the delivery state in order to avoid any undesired opening of the container. Before being used for the first time a lower housing part of the nebulizer is completely closed. Thus, the pre-installed container is opened by a delivery tube piercing a sealing and a septum to fluidically connect to the inner bag of the container. Further, the transportation lock is opened so that the container can move inside the nebulizer back and forth.

By rotating the lower housing part the drive spring can be put under tension and fluid can be sucked into a compression chamber of the pressure generator. Simultaneously, the container is moved into the lower housing part in a stroke movement within the nebulizer and when tensioned for the first time the container may be pierced through its base by a piercing element in the lower housing part to allow venting of the container. After manual operation of a stop element the drive spring is released and moves the delivery tube into the pressure chamber so that the fluid is put under pressure by the drive spring and is delivered or atomized through a nozzle into a mouthpiece as an aerosol, without the use of propellant gas.

WO 2007/022898 A2, US 2011/0011393 A1, and WO 2012/162305 A1 disclose a similar nebulizer. A container can be inserted into a housing of the nebulizer. The housing is closed by a lower housing part. The container is moving axially forth and back during conveying of the fluid to be nebulized, and during pressure generation and nebulization. A counter device can be arranged in the lower housing part. The counter device locks the nebulizer against further use if a predetermined number of operations has been reached or exceeded. Then, the housing part may be replaced together with the counter device and the container. The container may be connected inseparably with the housing part. Further, the nebulizer comprises a device for permanently locking the nebulizer when a certain number of containers have been used or when a certain number of operations have been reached.

SUMMARY

Object of the present invention is to provide a nebulizer allowing easy and/or improved handling and/or secure or defined indication of handling and state.

According to one aspect of the present invention, the nebulizer comprises preferably a blocking device which is adapted to block opening of the housing, when the nebulizer or, in particular, its energy store is in a tensioned state (In this tensioned state, the nebulizer is in a loaded state, i.e. in a ready-to-discharge state, in particular in a state in which a dose of fluid is dispensed or discharged upon the actuation of a stop element). Preferably, the housing can only be opened if the nebulizer is in an untensioned state or discharged state. This allows or ensures secure handling and/or a defined position of the preferably moveable container when opening the nebulizer and/or replacing the container.

According to another aspect of the present invention, the nebulizer comprises preferably a blocking device, preferably the blocking device mentioned above, adapted to block indexing (i.e. the step-wise movement) of an indicator member, when the nebulizer or its energy store is in a tensioned state. This allows or ensures easy and/or improved handling and/or secure or defined indication of handling and state, in particular when the indicator member shows a required container replacement only when the nebulizer or its energy store is not in a tensioned state, i.e. preferably after relaxing the energy store or a drive spring of the nebulizer.

Preferably, the indicator member shows numbers and/or symbols, in particular indicating any required steps such as container replacement, closing of the housing, or the like.

Preferably, the blocking device controls blocking of opening of the housing by means of the indicator member, in particular by blocking required indexing of the indicator member.

Preferably, the blocking device blocks indexing of the indicator member in the tensioned state. The indicator member, in turn, blocks preferably opening of the housing in the tensioned state. Thus, the blocking device preferably indirectly (in particular by means of the indicator member and/or control member) controls or blocks opening of the housing and/or locks the nebulizer or housing part selectively against opening.

Preferably, the nebulizer comprises a counter device for counting pressurizing and/or dispensing operations of the nebulizer and a guidance device which comprises the indicator member and/or control member. In particular, an actuation part of the counter device cooperates with the guidance device when a predetermined number of pressurizing and/or dispensing operations have been reached or exceeded with the current container. Thus, the guidance device can indicate a required container replacement and/or enable the opening of the housing when a container has to be replaced.

The control of opening of the nebulizer via the indicator member allows a simple integration of the blocking device and/or results in a well defined indication of the necessary steps to a user and/or allows a secure handling for the user.

According to a further aspect of the present invention, the nebulizer comprises preferably an indicator device for indicating a tensioned state of the nebulizer or its energy store. This allows visualization of the status (tensioned or not tensioned) and facilitates handling of the nebulizer.

According to another aspect of the present invention, the nebulizer comprises preferably a manually depressable actuator member at a housing part, wherein the housing part is detachable together with the actuator member from the housing of the nebulizer for replacing the container when the actuator member is depressed. This facilitates the handling in particular because the user can detach the housing part together with the still depressed actuator member from the nebulizer and does not have to leave the actuator member at the nebulizer.

Preferably, the actuator member is or forms a push button. This allows very easy and intuitive manual actuation.

The actuator member or push button acts preferably on a retaining element arranged on or at the nebulizer non-detachable. Thus, the housing part is detached from the retaining elements as well when the housing part is detached from the nebulizer.

The retaining element forms preferably a catch or snap for preferably automatically holding or securing the housing part when it is shifted onto or into the nebulizer, most preferably with two catch positions, i.e. a first catch position with partly closed housing part or housing of the nebulizer and a second catch position with completely closed housing part or housing.

Preferably, the retaining element is blocked against release when the blocking device or indicator member blocks release of the retaining element. In particular, the blocking device or indicator member may block the retaining element against depression and, thus, against release (in this case, the retaining element cannot be depressed and, thus, the actuator member or push button can neither be depressed), in particular when a predetermined number of doses of fluid have not yet been dispensed from the current container, the nebulizer is still tensioned and/or a further container replacement is not allowed.

The above aspects of the present invention and the further aspect described below can be realized independently from each other, and in any combination.

DESCRIPTION OF THE DRAWINGS

Further advantages, features, characteristics and aspects of the present invention will become apparent from the claims and the following description of a preferred embodiment with reference to the drawings. It shows:

DETAILED DESCRIPTION

Figure 1:
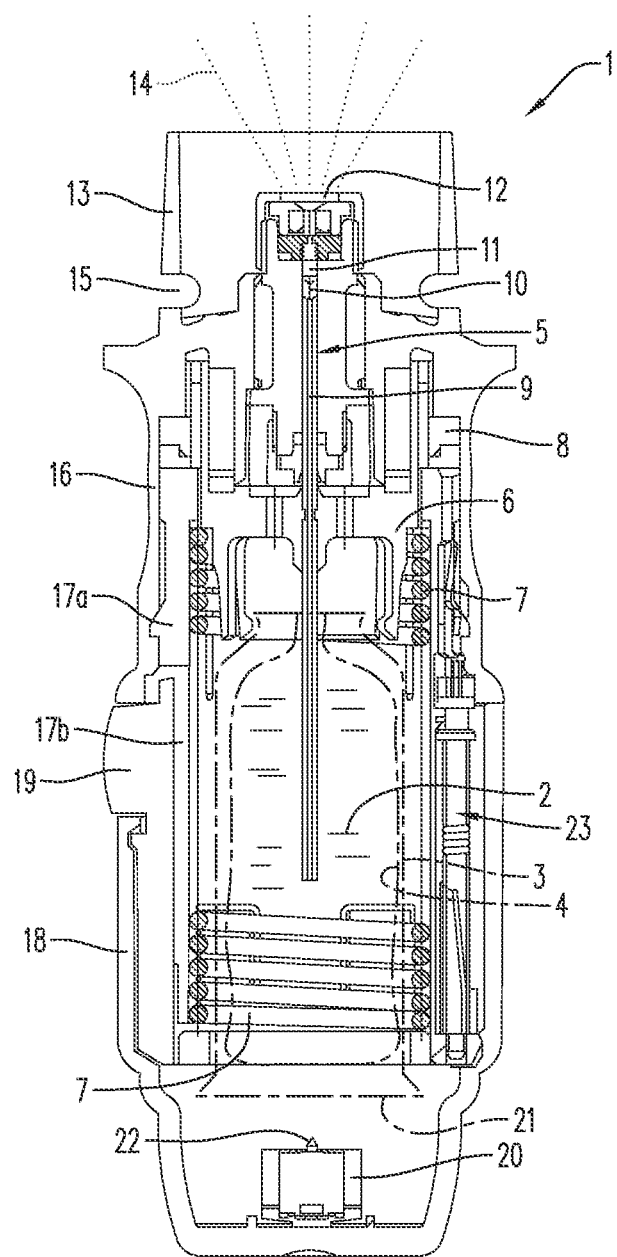
FIG. 1 a schematic section of a known nebulizer in a non-tensioned state.

In the Figures, the same reference numerals are used for identical or similar parts, resulting preferably in corresponding or comparable properties and advantages, even if the associated description is not repeated.

Figure 2:
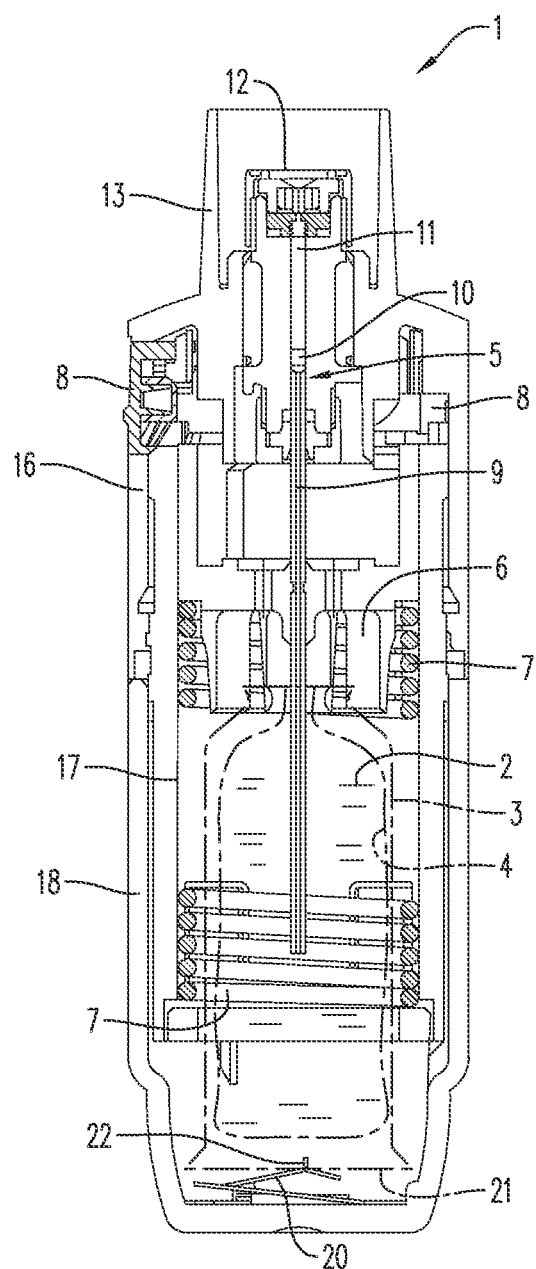
FIG. 2 a schematic section, rotated 90° compared with FIG. 1, of the known nebulizer in a tensioned state.

FIGS. 1 and 2 show a known nebulizer 1 for atomizing a fluid 2, particularly a highly effective pharmaceutical composition, medicament or the like, diagrammatically shown in a non-tensioned state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed, which can be breathed in or inhaled by a user. Usually the inhaling is done at least once a day, more particularly several times a day, preferably at set intervals, depending on the complaint or illness from which a patient is suffering.

The nebulizer 1 is provided with or comprises an insertable or replaceable container 3 containing the fluid 2. The container 3 thus forms a reservoir for the fluid 2, which is to be nebulized. Preferably, the container 3 contains multiple doses of fluid 2 or active substance in particular sufficient to provide up to 200 dosage units or doses, for example, i.e. to allow up to 200 sprays or applications. A typical container 3, as disclosed in WO 96/06011 A1, holds e.g. a volume of about 2 to 20 ml.

It has to be noted that the dose can vary, in particular depending on the fluid 2 or medicament. The nebulizer 1 can be adapted respectively.

Further, the number of doses contained in the container 3 and/or the total volume of the fluid 2 contained in the container 3 can vary depending on the fluid 2 or respective medicament and/or depending on the container 3 and/or depending on the necessary medication or the like.

Preferably, the container 3 can be replaced or exchanged, wherein the number of containers 3, which can be used with the same nebulizer 1, is preferably restricted, e.g. to a total number of four or five containers 3.

The container 3 is preferably substantially cylindrical or cartridge-shaped and once the nebulizer 1 has been opened the container 3 can be inserted therein preferably from below and changed if desired. It is preferably of rigid construction, the fluid 2 in particular being held in a collapsible bag 4 in the container 3. In particular, the container 3 comprises a venting hole 31 which is opened before or during first use.

The nebulizer 1 comprises a delivery mechanism, preferably a pressure generator 5, for conveying and nebulizing the fluid 2, particularly in a preset and optionally in an adjustable dosage amount. The nebulizer or pressure generator 5 comprises preferably a holder 6 for releasably holding the container 3, a drive spring 7 associated to the holder 6, only partly shown, and/or a stop element 8 preferably in form of or with a button for preferably manual actuation or depressing, which stop element 8 can catch and block the holder 6 and can be manually operated to release the holder 6 allowing drive spring 7 to expand. The nebulizer 1 or pressure generator 5 comprises preferably further a conveying element, such as a conveying tube 9, a non-return valve 10, a pressure chamber 11 and/or a nozzle 12 for nebulizing the fluid 2 into a mouthpiece 13. The completely inserted container 3 is fixed or held in the nebulizer 1 via the holder 6 such that the conveying tube 9 penetrates into the container 3. The holder 6 is preferably constructed so that the container 3 can be exchanged.

When the drive spring 7 is axially tensioned in the tensioning process the holder 6 with the container 3 and the conveying tube 9 are moved downwards in the drawings and fluid 2 is sucked out of the container 3 into the pressure chamber 11 of the pressure generator 5 through the non-return valve 10. In this state, the holder 6 is caught by the stop element 8 so that the drive spring 7 is kept compressed. Then, the nebulizer 1 is in the so-called loaded or tensioned state.

During the subsequent relaxation in the nebulization process after actuation or pressing of the stop element 8 the fluid 2 in the pressure chamber 11 is put under pressure as the conveying tube 9 with its now closed non-return valve 10 is moved back in the pressure chamber 11, here in the drawings upwards, by the relaxation or force of the drive spring 7 and now acts as a pressing ram or piston. This pressure forces the fluid 2 through the nozzle 12, whereupon it is nebulized into the aerosol 14, as shown in FIG. 1.

Generally, the nebulizer 1 operates with a spring pressure of 5 to 200 MPa, preferably 10 to 100 MPa on the fluid 2, and/or with a volume of fluid 2 delivered per stroke of 10 to 50 μl, preferably 10 to 20 μl, most preferably about 15 μl. The fluid 2 is converted into or nebulized as aerosol 14, the droplets of which have an aerodynamic diameter of up to 20 μm, preferably 3 to 10 μm. Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while an air supply can be sucked into the mouthpiece 13 through at least one optional air supply opening 15.

Preferably, the drive spring 7 can be manually activated or tensioned (or the nebulizer 1 can be loaded), in particular by actuation of an actuation member.

The nebulizer 1 comprises preferably a housing or (upper) housing part 16 and optionally a biasing or inner part 17 preferably which is rotatable relative thereto (FIG. 2) and/or having an upper part 17a and a lower part 17b (FIG. 1).

The nebulizer 1 comprises preferably an in particular manually operable (lower) housing part or cap 18 releasable fixed, particularly fitted or held onto the inner part 17, preferably by means of a retaining element 19.

Preferably, the housing parts 16 and 18 and/or other parts form a housing of the nebulizer 1. In order to insert and/or replace the container 3, preferably the housing can be opened and/or the housing part 18 can be detached from the nebulizer 1 or its housing. Generally and preferably, the container 3 can be inserted before the housing is closed and/or before the housing part 18 is connected to the housing. Preferably, the container 3 is inserted, opened and/or fluidically connected to the delivery mechanism automatically or simultaneously when (completely) connecting the housing part 18 to the housing/nebulizer 1 and/or when (completely) closing the housing/nebulizer 1.

The actuation member, preferably the housing part 18, can be actuated, here rotated relative to the upper housing part 16, carrying with it or driving the inner part 17. As a result the drive spring 7 is tensioned in the axial direction by means of a gear or transmission (not shown) formed between the inner part 17, in particular its upper part 17a, and the holder 6 and acting on the holder 6. During tensioning the container 3 is moved axially downwards until the container 3 assumes an end position as shown in FIG. 2. In this activated or tensioned state the drive spring 7 is under tension and can be caught or held by the stop element 8. During the nebulizing process the container 3 is moved back into its original position (non-tensioned position or state shown in FIG. 1) by the drive spring 7. Thus the container 3 executes a lifting or stroke movement during the tensioning process and during the nebulizing process.

The housing part 18 preferably forms a cap-like lower housing part and fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal thereon with a piercing element 22 when the container 3 makes contact with it for the first time, to allow air in or aeration.

The nebulizer 1 comprises preferably a counter device 23, which counts in particular actuations of the nebulizer 1, preferably by detecting its tensioning or the rotation of the inner part 17 relative to the upper part 16 or housing. Preferably, the counter device 23 or an associated lock locks the (further) actuation or use of the nebulizer 1, e.g. blocks further rotation of the housing part 18/inner part 17 and, thus, tensioning of the nebulizer 1 or its drive spring 7 and/or blocks actuation of the stop element 8, when a certain number of actuations or operations or discharged doses has been reached or exceeded.

A preferred construction and mode of operation of the inhaler or nebulizer 1 will now be described in more detail with reference to FIGS. 3 to 5, but emphasizing only essential differences from the nebulizer 1 according to FIGS. 1 and 2. The remarks relating to FIGS. 1 and 2 thus apply preferably accordingly or in a similar manner, while any desired combinations of features of the nebulizer 1 according to FIGS. 1 and 2 and the nebulizer 1 described below are possible.

Preferably, the container 3 is pre-installed. This can be realized in particular as shown in WO 2006/125577 A2 or as described in the following.

Figure 3:
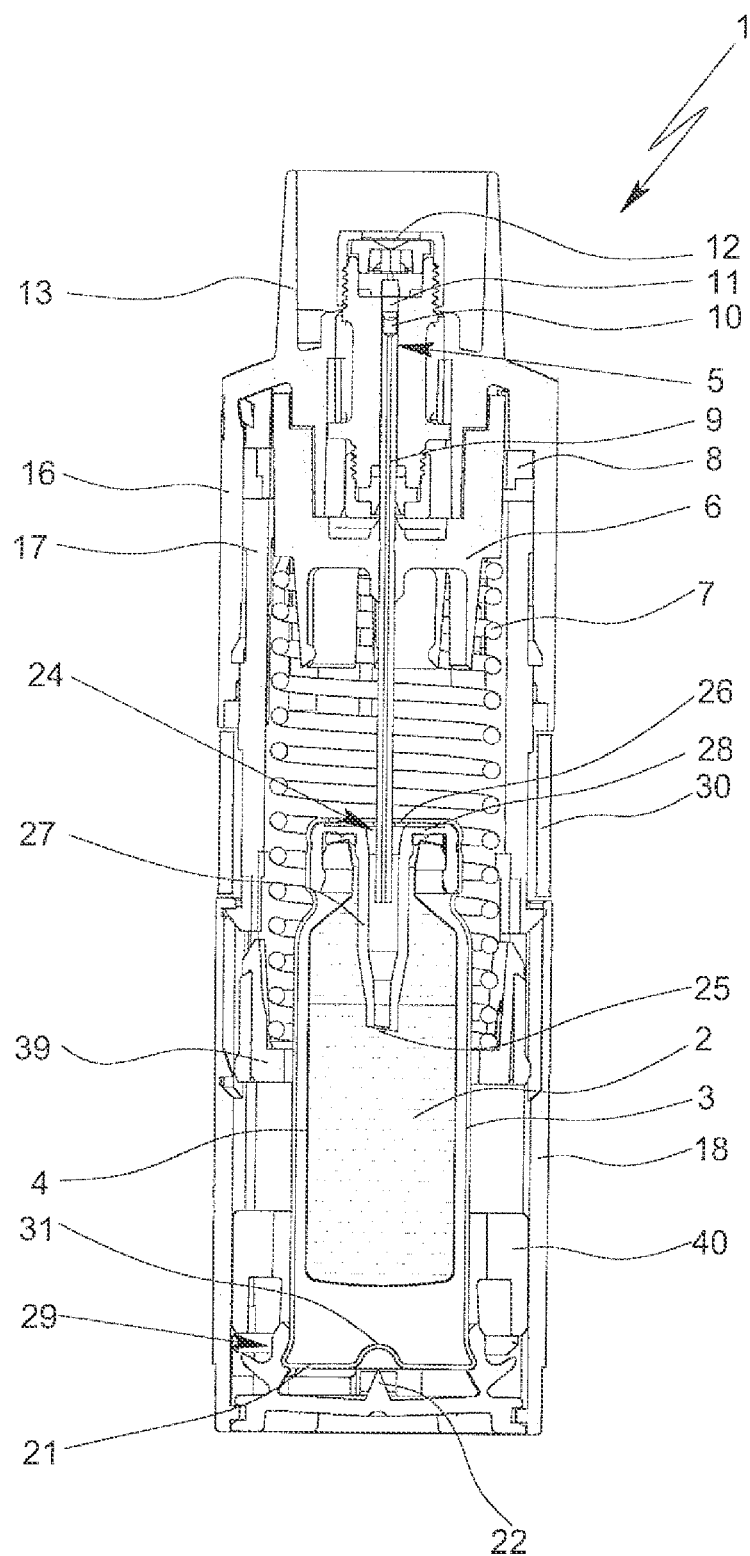
FIG. 3 a schematic section of a nebulizer in a delivery state with a partly closed housing and with a pre-installed, closed container.

FIG. 3 shows the nebulizer 1 in a delivery state with preferably pre-installed container 3, which is still closed. In this state, the housing of the nebulizer 1 is not completely closed, in particular the housing part 18 is not completely pushed on the inner part 17. FIGS. 4 and 5 show the nebulizer 1 in an activated state with the housing completely closed and with the container 3 opened. In FIG. 4, the nebulizer 1 or drive spring 7 is tensioned, i.e. the container 3 is in its lower position. FIG. 5 shows the nebulizer 1 in a non-tensioned state, e.g. after dispensing or nebulizing of one dose of the fluid 2; the container 3 is in its upper position.

The container 3 comprises a fluid outlet 24 for outputting the fluid 2 to be dispensed. In particular, the fluid outlet 24 allows a fluidic connection between the container 3 or its bag 4 on one hand and the nebulizer 1, its pressure generator 5 or the conveying element on the other hand.

The fluid outlet 24 has an inner closure 25 that is preferably formed by a septum, a membrane, a plastic seal or the like and/or is provided inside the container 3. Optionally, a second or outer closure 26 can be provided such that successive opening is possible by means of one common element, in particular the conveying element or conveying tube 9 or the like, and/or by piercing.

Preferably, the first or inner closure 25 is formed or supported by a closure part 27 extending from the outlet or head end of the container 3 into the container 3 or bag 4. The second or outer closure 26 is preferably located adjacent to the head or axial end of the container 3 and/or held or connected to a flange 28, which can be formed by the closure part 27 or any other suitable part. However, other constructional solutions are possible.

In the delivery state according to FIG. 3, the container 3 has been pre-installed, i.e. inserted into the nebulizer 1. However, the container 3 or its fluid outlet 24 is not yet opened. In particular, the second closure 26 is already opened, but not the first closure 25. This is achieved in particular in that the housing of the nebulizer 1 is closed only partly, i.e. not completely, in the delivery state.

In particular, the container 3 is attached to or held by or secured in the housing part 18, in particular by a transportation lock 29, which is preferably arranged within or at the housing part 18. The transportation lock 29 holds the container 3 preferably temporarily, in particular before attaching the housing part 18 to the nebulizer 1 and/or in the delivery state. In particular, the transportation lock 29 holds the container 3 fixed during the fluidic connection of container 3 and/or during the mechanic connection of container 3, here with holder 6. Preferably, the transportation lock 29 holds the container 3 fixed during opening, in particular piercing, the container 3.

In the delivery state, in which the nebulizer 1 can be shipped or delivered to the user or is still packed, the nebulizer 1 or the housing part 18 is preferably secured, in particular by means of a securing member 30, e.g. a banderole, such that the container 3 and/or housing part 18 are held sufficiently spaced from the nebulizer 1 or upper housing part 16 and/or prevented from being completely closed or completely inserted or pushed on the conveying element or tube 9, the housing or inner housing part 17 or the like and/or such that (complete) opening of the container 3, namely of the first closure 25, is prevented.

Once the security member 30 has been removed a user (not shown) can push the housing part 18 fully on in the axial direction and thereby open the container 3, i.e. first closure 25, by inserting the conveying element or conveying tube 9. FIGS. 4 and 5 show this activated state with the housing part 18 pushed fully on and/or the container 3 open (fluidically connected to the nebulizer 1 or its pressure generator 5 or the conveying element or tube 9).

FIG. 4 shows the nebulizer 1 or container 3 in the activated state, the container 3, i.e. first closure 25, is open, i.e. the container 3 or its fluid 2 is fluidically connected to the nebulizer 1 or its pressure generator 5, and the housing part 18 has been pushed fully on in the axial direction. In order to bring the holder 6 into (complete) engagement with the container 3 at the head end and then be able to move the container 3 back and/or forth for the suction/tensioning and pressing strokes, it may be necessary to tension the nebulizer 1 or it drive spring 7 for the first time. During this tensioning process the holder 6 is moved together with the conveying tube 9 axially towards or into the housing part 18, thus bringing the holder 6 into (complete) engagement with the container 3 and preferably also moving or pressing the container 3 against the piercing element 22 in the region of the base of the housing part 18 and thereby piercing or opening a venting hole 31 in the container base 21. FIG. 4 shows the nebulizer 1 in this tensioned and activated state. The holder 6 is engaged with the container 3 and the conveying tube 9 has been fully inserted into the container 3.

FIG. 5 shows the nebulizer 1 in the relaxed, non-tensioned state, i.e. after atomization or discharge of a dose of the fluid 2. The holder 6 and the container 3 are in the upper position. The holder 6 is still engaged with the container 3 and remains engaged during the further uses of the nebulizer 1. Further, the container 3 is still open and fluidically connected, i.e. the nebulizer 1 remains activated.

To prevent unwanted opening of the container 3, particularly of the first closure 25, in the delivery state of the nebulizer 1, and/or to prevent (axial) movement of the container 3 relative to the associated housing part 18 before complete closing of the nebulizer 1, preferably the transportation lock 29 is provided. By frictional, forcible or interlocking engagement, for example, the transportation lock 29 prevents the container 3 from undesirably moving axially.

Preferably, the opening of the transportation lock 29 occurs automatically when closing the nebulizer 1 or its housing completely, i.e. when snapping or pushing on the housing part 18 completely towards the upper housing part 16. During this (preferably linear, axial or telescopic) closing movement, the transportation lock 29 is opened and the container 3 released in axial direction preferably during or after piercing or opening the container 3 and/or preferably during only a last part of the movement and/or just little before the final completely closed position is reached or just when the final completely closed position is reached.

During the closing movement in which preferably parts 17 and 18 are joined, the transportation lock 29 is preferably opened by the direct or indirect interaction with or actuation by the housing of the nebulizer 1, the inner part 17 or its lower part 17*b* or the like. Preferably, the container 3 and/or first closure 25 are opened as well as the transportation lock 29 by means of a common actuation and/or component, here the closing movement of the nebulizer 1 or its housing or bottom part 18.

Figure 4:
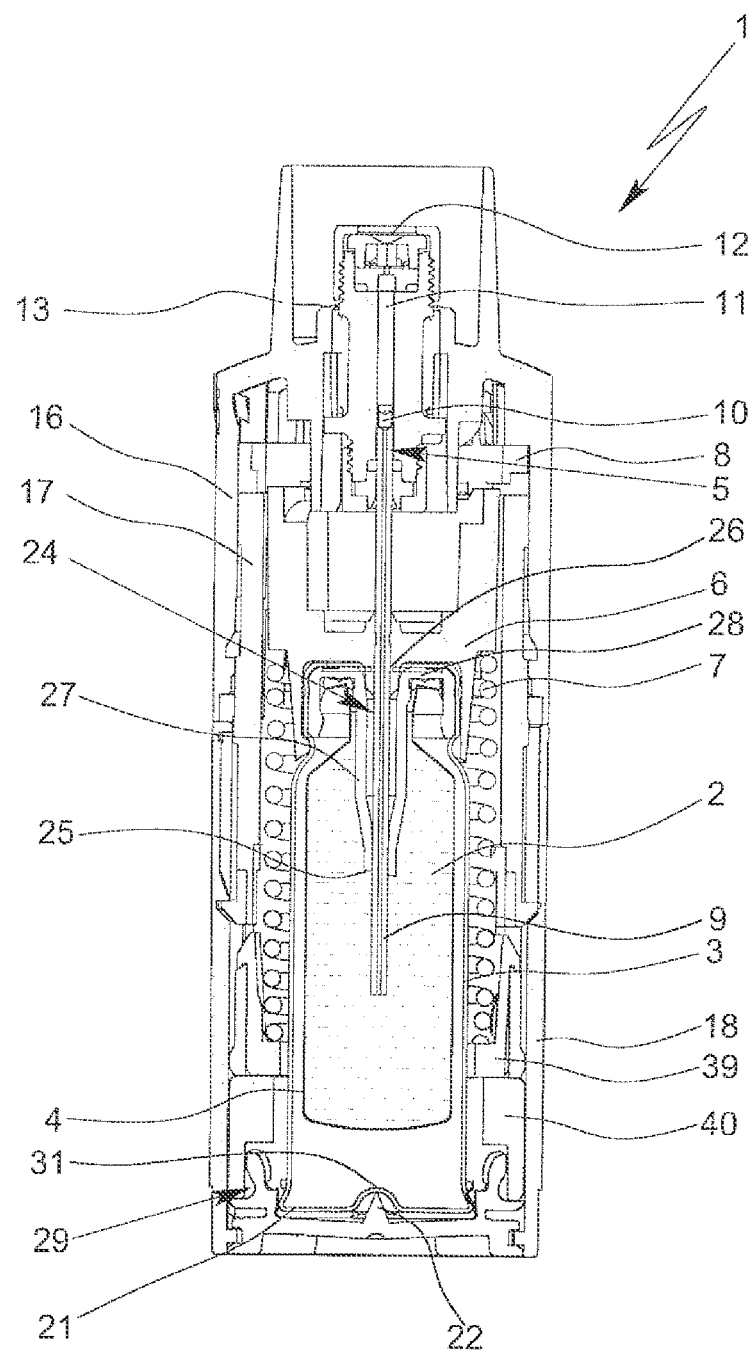
FIG. 4 a schematic section of the nebulizer according to FIG. 3 in an activated, tensioned state with completely closed housing and with opened container.
Figure 5:
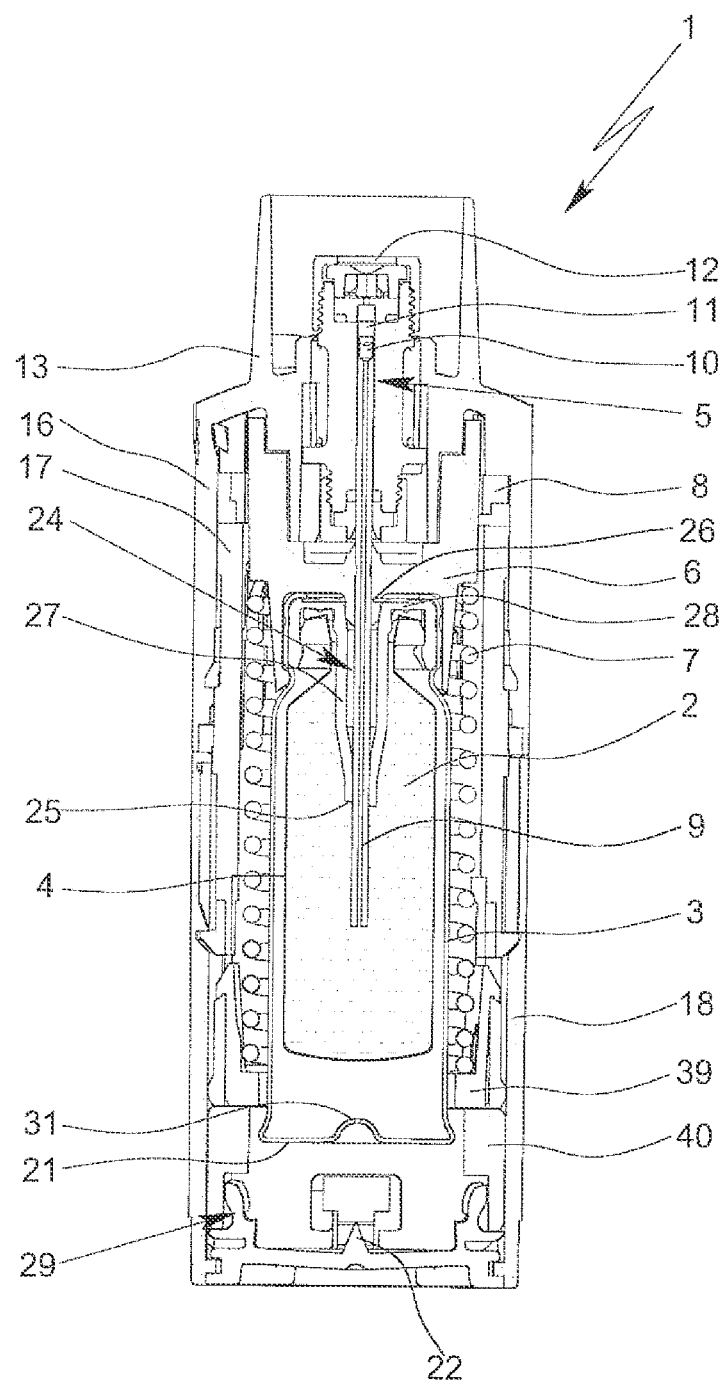
FIG. 5 a schematic section of the nebulizer according to FIG. 4 in a non-tensioned state.

FIGS. 4 and 5 show the transportation lock 29 in the open position, i.e. wherein the container 3 is free to move axially.

In the following, a preferred embodiment of the nebulizer 1 according to the present invention will be described in more detail with reference to the further Figures, wherein only essential differences from the nebulizer 1 described above or shown in FIGS. 1 to 5 will be emphasized or described. Thus, the remarks relating to FIGS. 1 to 5 apply preferably accordingly or in a similar manner, while any desired combinations of features are possible.

Figure 6:
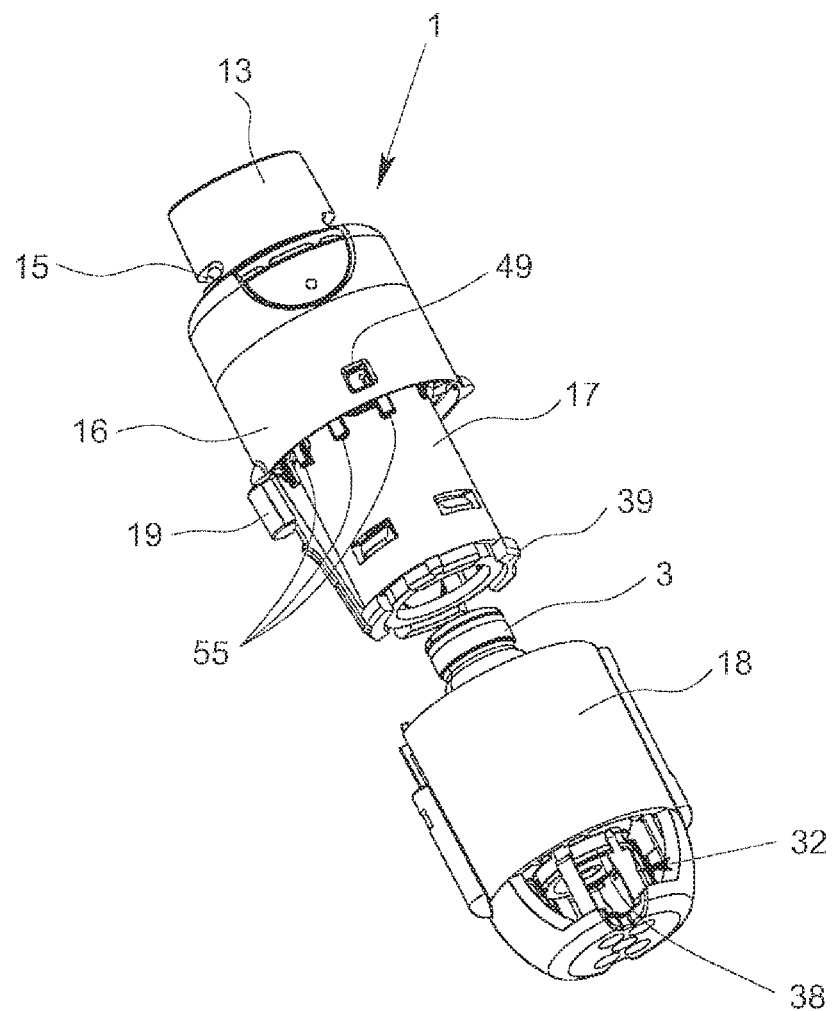
FIG. 6 a schematic perspective view of a nebulizer according to the present invention with a separate housing part shown with a partly cut-away portion, the housing part having a securing device holding unmoveably a container of the nebulizer.

FIG. 6 shows the nebulizer 1 in a perspective side view with not yet mounted, i.e. separated (lower) housing part 18 (partly cut open for illustration purposes) with associated container 3. The container 3 has not been inserted or pre-installed in the nebulizer 1 yet. With other words, the nebulizer 1 has not been assembled yet or is not in the preferred delivery state yet.

Figure 7:
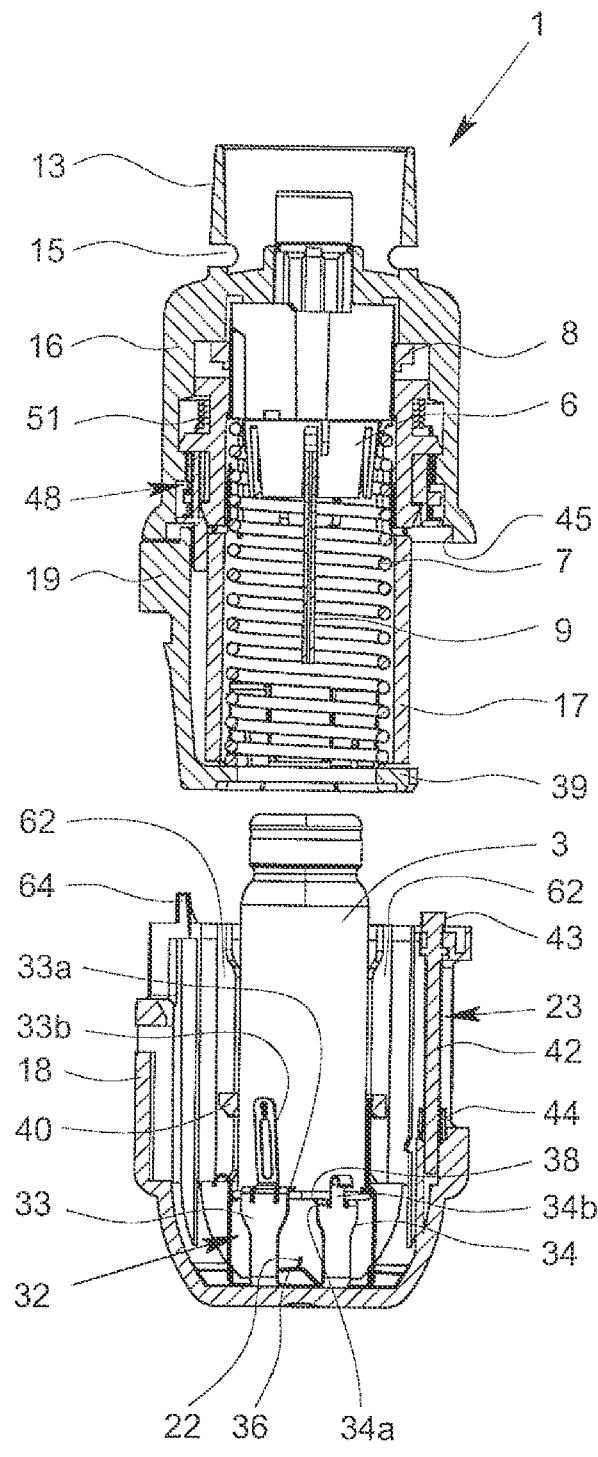
FIG. 7 a schematic section of the nebulizer according to FIG. 6.

FIG. 7 shows the nebulizer 1 in a schematic section as well as the container 3 and housing part 18 which are still separated from the (upper part of the) nebulizer 1.

The nebulizer 1 or its housing or housing part 18 comprises preferably a securing device 32 which may have different functions. The securing device 32 may hold the container 3 such that the container 3 is moveable back and forth within the completely closed housing for conveying the fluid 2, pressure generation and/or nebulization, wherein the securing device 32 may ensure that the container 3 is inseparable from the housing or housing part 18. Thus, only complete replacement of the housing part 18 together with the respective container 3 is possible. Alternatively or additionally, the securing device 32 may form the transportation lock 29. Alternatively or additionally, the securing device 32 may prevent that the used container 3 and/or used housing part 18 can be (re)connected to or used with the nebulizer 1 once more.

When the securing device 32 or transportation lock 29 is closed, the container 3 is held or counter-beared for opening by inserting the conveying element or tube 9, preferably wherein a press-fit is formed between the conveying element or tube 9 and the container 3 or closure part 27, and/or for (completely) connecting the container (head) to the holder 6. With other words, the transportation lock 29 or securing device 32 form preferably a counter-bearing for the container 3 during closing of the nebulizer 1.

When the securing device 32 or transportation lock 29 is closed, the container 3 is held spaced from the piercing element 22.

The securing device 32 is preferably located or arranged or fixed at or in the housing part 18 as shown in FIGS. 6 and 7.

Preferably, the securing device 32 comprises or consists of a metal and/or stamped part and/or consists of a single, unitary part. The securing device 32 may consist of two or more parts, preferably connected by means of gluing, crimping, riveting, welding, or the like.

Preferably, the securing device 32 is made of steel, in particular spring steel. Preferably, the securing device 32 is produced from sheet material by cutting, stamping or the like and/or by bending. Preferably, the securing device 32 or a part thereof forms a cage, in particular encompassing the container 3 or an end portion thereof, in particular the container base 21.

Preferably, the securing device 32 comprises holding elements 33 and/or locking elements 34. The elements 33 and/or 34 are preferably designed like arms, fingers, leaves or the like. In particular, the elements 33 and 34 are alternately distributed over the circumference of the container 3. Preferably, the securing device 32 comprises multiple holding elements 33 and multiple locking elements 34, in particular three or more holding elements 33 and three or more locking elements 34. Preferably, the elements 33 and 34 extend at least essentially axially and/or in the direction of the back and forth movement of the container 3 and/or in the direction of the longitudinal or main extension of the nebulizer 1 or main dispensing direction of the aerosol 14.

Figure 8:
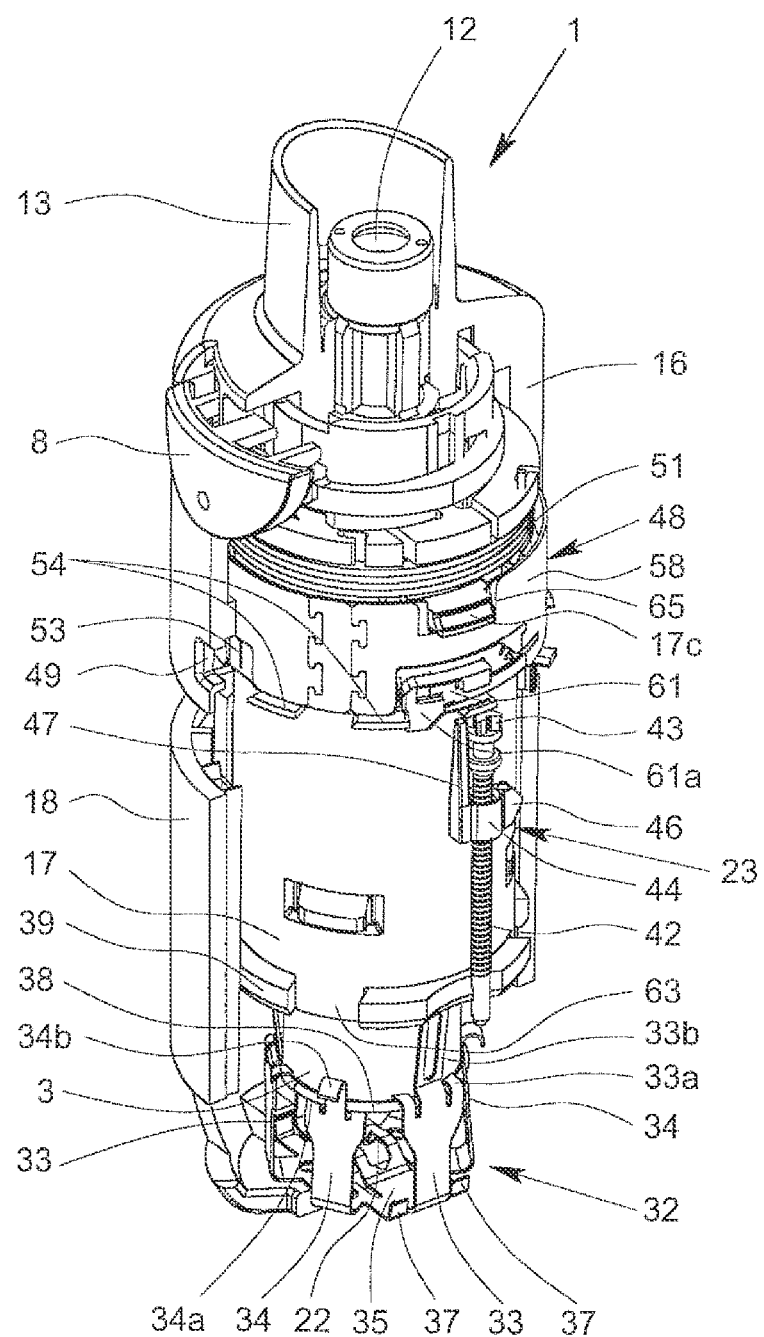
FIG. 8 a schematic side view of the nebulizer according to FIG. 6 with partly mounted housing part and with some cut-away portions, the container being held unmoveably.

Preferably, the elements 33 and 34 are held by or connected with a base 35 of the securing device 32, as shown in FIG. 8. FIG. 8 shows the nebulizer 1 in a schematic side view with already partly mounted housing part 18 and with some cut-away portions. The transportation lock 29 or securing device 32 is still closed or locked, i.e. the container 3 is still securely held so that it cannot axially move (axially means in the direction of the back and forth or stroke movements).

Preferably, the securing device 32 or base 35 comprises or holds the piercing element 22 for piercing the container 3, i.e. opening the container base 21 or its venting hole 31 or a respective sealing of the container 3 or the like in the activated and tensioned state, i.e. when the container 3 reaches its lower end position. In the shown and preferred embodiment, the piercing element 22 is formed by a respective bending of a spring portion 36 of the securing device 32 or its base 35. The spring portion 36 can support or facilitate the (complete or final) connection of the container 3 to the holder 6.

The securing device 32 or base 35 comprises preferably at least one or multiple fixing portions 37 for fixing the securing device 32 at or in the nebulizer 1 or housing or housing part 18. In particular, the fixing portions 37 may fix the securing device 32 when it is pressed into the housing part 18 by cooperating with the sidewall of the housing part 18. However, it is also possible to overmold the securing device 32, its base 35, the fixing portions 37 or the like. Moreover, the securing device 32 could be connected with the housing part 18 or the like in any other suitable manner, in particular, by a separate fixing member, by gluing or the like.

As already mentioned, the securing device 32 preferably forms the transportation lock 29 for holding the container 3 unmovable in the housing or housing part 18 in the delivery state of the nebulizer and/or before attaching the housing part 18 to the nebulizer 1. In this situation (in particular in the delivery state), the container 3 or a preferably radially protruding and/or circumferentially extending part or edge 38 thereof, preferably formed at the container base 21, is held preferably in a form-fit manner and/or between the holding elements 33 and locking elements 34, in particular between respectively formed or bent end portions 33a and 34a of the elements 33 and 34, respectively, as shown in FIGS. 6 to 8.

In the shown embodiment, the container 3 and/or edge 38 is caught between the end portions 33a and 34a, preferably alternatively. The holding elements 33 and/or end portions 33a grip or extend over the edge 38, and the locking elements 34 or its end portions 34a grip or extend under the edge 38, so that the edge 38 and container 3 are securely held in between, in particular by form-fit, preventing any axial movement of the container 3 relative to the securing device 32 and relative to the associated housing part 18 in this state or delivery state, i.e. with locked transportation lock 29/securing device 32.

Preferably, the end portions 33a and/or 34a are formed like claws or the like and/or extend preferably radially inwardly.

Preferably, the elements 33 and/or 34 can flex with its free ends radially outwardly.

Preferably, the securing device 32 is designed such that the associated container 3 can be connected with the securing device 32 by a respective axial force or movement, wherein the elements 33 and/or 34 flex preferably automatically outwardly as required to receive the container 3 in the locked position as shown in FIGS. 6 to 8. However, if necessary, a suitable tool (not shown) or the like could be used alternatively or additionally for assembly if necessary.

For example, the ends of the end portions 33a could be inclined such that the container 3 may be inserted into or connected with the securing device 32 by a respective axial movement so that the holding elements 33 flex outwardly to allow passing of edge 38.

Preferably, the holding elements 33 or its end portions 33a prevent separation of the container 3 from the securing device 32 and, thus, from the associated housing part 18 or the like.

In the present embodiment, the holding elements 33 extend preferably above the end portions 33a and/or form or comprise preferably arm-like guiding and/or locking portions 33b. These axial extensions and/or these portions 33b extend axially beyond the end portions 33a and/or may cooperate with the container 3 or its edge 38 during axial assembly of the container 3 with the securing device 32 such that the holding elements 33 are flexed sufficiently outwardly so that the edge 38 can pass the end portions 33a and the container base 21 can be seated on the end portions 34a of the locking elements 34.

The locking elements 34 preferably comprise actuation portions 34b at its free ends extending axially beyond the end portions 34a. The actuation portions 34b may radially guide the container 3 and/or facilitate insertion of the container 3 or its edge 38 between the free ends of the locking elements 34 although the locking elements 34 are preferably radially inwardly biased as well as the holding elements 33.

When, the container 3 is held with its edge 38 between the end portions 33a and 34a, the transportation lock 29/securing device 32 is closed, i.e. the container 3 cannot move axially within the housing part 18 or nebulizer 1.

For opening the transportation lock 29 or securing device 32, the locking elements 34 and/or its end portions 34a are flexed preferably radially outwardly so that the container 3 can freely move axially, in particular restricted such that the edge 38 can only move axially within the securing device 32 and/or that the axial movement is restricted (in the drawings upwardly) by the holding elements 33 or its end portions 33*b* and/or such that the container 3 cannot be separated from the securing device 32. This opening of the transportation lock 29 or securing device 32 will take place when activating the nebulizer 1, when using the nebulizer 1 for the first time and/or when completely closing the nebulizer 1. Then, the container 3 can axially move, in particular back and forth and/or with its edge 38 between the end portions 33*a* and the piercing element 22 in the present embodiment. This situation is schematically shown in the schematic section according to FIG. 9 which shows the nebulization with closed housing or housing part 18 and with opened transportation lock 29/securing device 32.

In FIG. 9, the container 3 is shown in its lower position similar to FIG. 4, in particular, wherein the container base 21 is in contact with the piercing element 32. However, the nebulizer 1 is not shown in the tensioned state, i.e. the holder 6 is not in its lower position, i.e. the holder 6 is not yet connected with the upper end or head of the container 3. Normally, the holder 6 would be connected to the container 3 in this situation with the container 3 in the lower position. With other words, usually the nebulizer 1 or drive spring 7 would be tensioned in the situation with the container 3 being in the lower position.

Preferably, the container is finally or completely or correctly connected to holder 6 when tensioning the nebulizer 1 or its drive spring 7 for the first time after completely closing the nebulizer 1. However, it is generally also possible that the nebulizer 1 is in the tensioned state, i.e. the drive spring 7 is already tensioned and the holder 6 is in the lower position, before or during (first) assembly with lower housing part 18. Consequently, the holder 6 should directly connect with the container 3 when completely closing the housing part 18, and the situation shown in FIG. 9 should normally not occur.

In FIG. 9, the end portions 34*a* are moved radially outwardly in order to open the transportation lock 29 or securing device 32. This is achieved preferably by flexing the locking elements 34 radially outwardly. This can be achieved in particular by acting on the actuation portions 34*b*.

Preferably, the transportation lock 29 is opened or the locking elements 34 are flexed outwardly when completely closing the nebulizer 1 or its housing part 18, in particular by cooperation with or abutment of the inner part 17, its lower part 17*b*, a retaining part 39 and/or a securing part 40. The retaining part 39 is preferably arranged at the upper housing part 16 or inner part 17. The securing part 40 is preferably arranged in the lower housing part 18.

The retaining part 39 is connected to the lower or free end of the inner part 17 or its lower part 17*b* in order to hold, bear or support an end (the lower end) of the drive spring 7. FIGS. 3 to 5 show a preferred construction of the retaining part 39. It is preferably formed as a ring and/or provided with hooks or the like for interconnection with the inner part 17. In the preferred embodiment, the retaining element 19 forms a unitary component or portion of the retaining part 39. However, other constructional solutions are possible.

In the embodiment shown in FIGS. 3 to 5, a preferably ring-like securing part 40 opens the transportation lock 29, in particular flexible arms of the transportation lock 29, to allow axial movement of the container 3. This securing part 40 keeps the transportation lock 29 or its flexible arms open when the nebulizer 1 or its housing part 18 has been completely closed. The securing part 40 is pushed axially downwards by abutment of the inner part 17 or retaining part 39 within the housing part 18 when completely closing the nebulizer 1.

In the preferred embodiment shown in FIGS. 6 to 15 and particular in FIG. 9, the nebulizer 1, housing part 18 or securing device 32 comprises the preferably ring-like securing part 40 for opening the transportation lock 29/securing device 32 or its locking elements 34. In particular, the securing part 40 is pushed axially downwards when closing the nebulizer 1 so that it is moved between the locking elements 34 or its actuation portions 34*b* and exerts an axial force radially outwards. Preferably, an inclined plane converts the axial or closing movement into an opening or radial movement which forces the actuation portions 34*b* radially outwardly when the securing part 40 is forced axially downwardly, here by abutment of the retaining part 39, in particular in the axial end position shown in FIG. 9.

Preferably, the securing part 40 and/or locking elements 34 or actuation portions 34b comprise a respectively inclined guiding surface 41 or the like to convert the axial closing movement or movement of the securing part 40 into the desired radial opening movement of the locking elements 34 or actuation portions 34b and, thus, of the end portions 34a to open the transportation lock 29, in particular when the housing has been completely closed or when the housing part 18 has been pushed completely on the nebulizer 1.

However, other constructional solutions are possible to realize opening of the transportation lock 29 or securing device 32 or its locking elements 34 or end portions 34a when closing the nebulizer 1 or its housing parts 18.

In the preferred embodiment the securing part 40 serves alternatively or additionally another purpose. Namely, the securing part 40 prevents the locking portions 33b from moving radially apart or flexing radially outwards before the nebulizer 1 is assembled with its housing part 18 for the first time.

As already mentioned, the securing device 32 prevents preferably that a container 3 can be connected to or used with the nebulizer 1 once more. In particular, the securing device 32 can prevent that a used housing part 18 or used container 3 can be reconnected to the nebulizer 1 once it has been detached from the nebulizer 1. Thus, the securing device 32 prevents any undesired reuse of the container 3 and/or housing part 18 with its preferably inseparable container 3.

In the present embodiment, the undesired reuse is prevented in that the locking portions 33b force apart or move apart or radially and/or outwards at least after the used container 3 and/or housing part 18 has been detached from the nebulizer 1 such that the used container 3 and/or housing part 18 cannot be connected to or used with the nebulizer 1 once more. Preferably, the locking portions 33b are biased such that the locking portions 33b force apart or move radially and/or outwards after release.

In the preferred embodiment, the locking portions 33b are held together or held against moving apart, radially and/or outwards by the securing part 40 (schematically indicated in FIG. 7) before the container 3 and the associated housing part 18 have been connected to the nebulizer 1 for the first time. In this pre-assembly state, the securing part 40 is located preferably near the free ends of the locking portions 33b and/or it encompasses that locking portions 33b such that locking portions 33b are held sufficiently close together to be inserted with its free ends within the retaining part 39 and/or drive spring 7 when pushing the housing part 18 axially onto the nebulizer 1 or its inner part 17, in particular lower part 17b.

Figure 9:
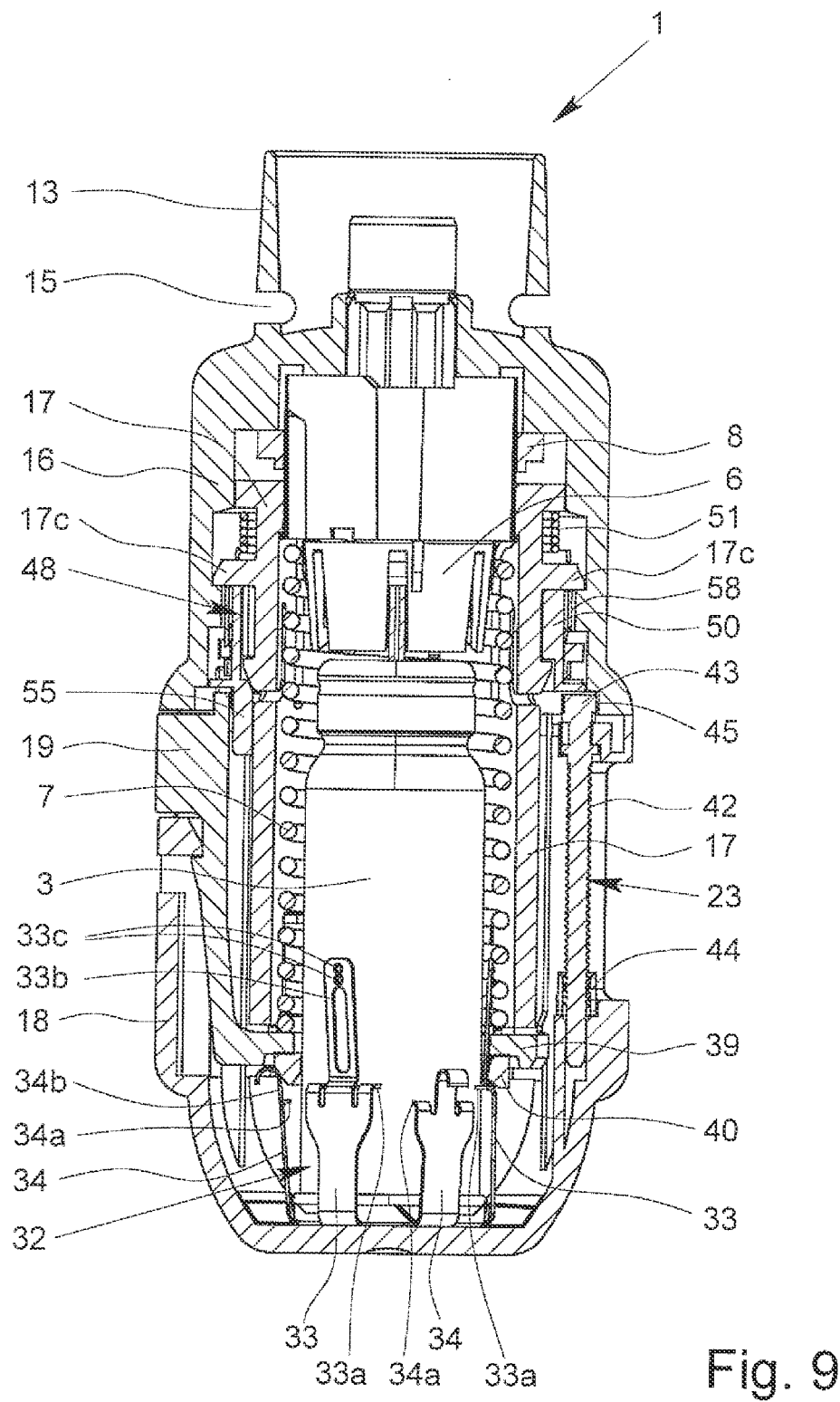
FIG. 9 a schematic section of the nebulizer according to FIG. 6 in the completely closed state with opened securing device so that the container can move axially.

The securing part 40 may cooperate with the locking portions 33b or protrusions 33c thereof (shown in FIG. 9) preferably such that the securing part 40 is held by a preferably radial engagement and/or frictional force in its (upper) position holding the locking portions 33b or holding elements 33 together in the pre-assembly state. Later during assembly, in particular during complete closing of the housing or pushing on the housing part 18, the locking portions 33b are moved into the retaining part 39 and drive spring 7, while the securing part 40 is moved axially downwards or towards the securing device 32, the container base 21 and/or bottom part of the end of the housing part 18. Then, the end position or completely assembled position is reached as shown in FIG. 9. In this state, the radially biased locking portions 33b are held together by the drive spring 7 as the securing part 40 does not hold the locking portions 33b together any more.

Preferably, the securing part 40 has opened the transportation lock 29 or locking elements 34 in the last part of the closing movement or just when completely closing the nebulizer 1 as already mentioned.

Figure 10:
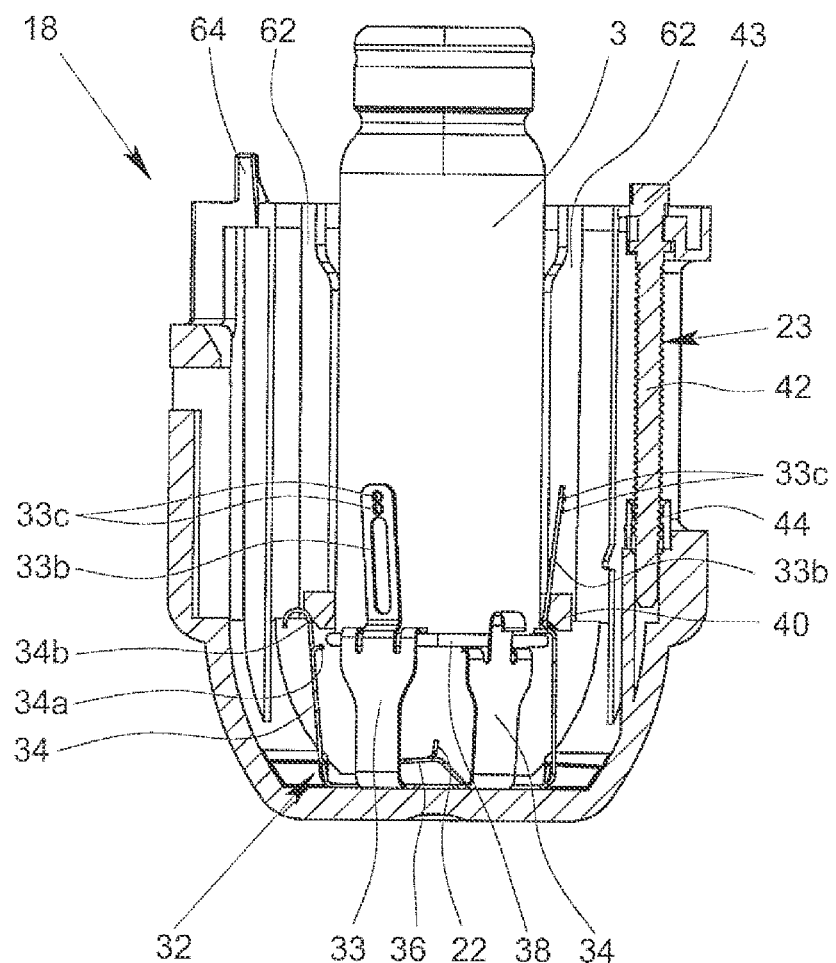
FIG. 10 a schematic section of the housing part with the associated container after use or separation from the nebulizer.

The schematic section of FIG. 10 shows the housing part 18 together with its associated container 3 after it has been used and separated from the nebulizer 1. The securing part 40 remains preferably in its lower position. The transportation lock 29 is (still) open. The container 3 is shown in its upper position where it is held by the end portions 33a of the holding elements 33 when detaching the container 3 from the nebulizer 1, in particular from the holder 6 and the conveying element or tube 9.

FIG. 10 shows that the locking portions 33b have been forced apart, in particular due to its biasing or elastic force, here moved radially outwardly with its free ends in particular due to its preferably radial biasing or elastic force. This forced apart position of the locking portions 33b blocks reconnection of the container 3 and/or housing part 18 and/or securing device 32 with the nebulizer 1. Thus, the already used container 3 cannot be reused. Thus, misuse of the container 3 or nebulizer 1 can be prevented.

The securing part 40 may additionally secure the holding elements 33 or its end portions 33a against radial opening when the securing part 40 is in its lower position as shown in FIGS. 9 and 10. In this case, the securing part 40 contacts the holding elements 33 preferably on the outer side to prevent or restrict any outward flexing. Thus, the securing device 32 or its holding elements 33 or end portions 33a are secured against opening so that the container 3 or its edge 38 is securely held within the securing device 32 or the cage formed by the securing device 32 or holding elements 33.

In the preferred embodiment, the counter device 23 is arranged preferably at the housing part 18 as schematically shown in FIGS. 7 to 10.

The counter device 23 counts the actuations or operations of the nebulizer 1 or the discharged doses, preferably for the respective container 3.

Preferably, the counter device 23 counts actuations or operations by detecting the rotation of the inner part 17 relative to the upper part 16 of the housing. With other words, the counter device 23 may count the tensioning the nebulizer 1 or its drive spring 7. However, other constructional solutions are possible.

Preferably, the counter device 23 comprises a threaded spindle or shaft 42 with an associated, preferably unitary formed drive gear 43. The counter device 23 comprises preferably further a rider 44 associated to the threaded shaft 42 and cooperating with the threaded shaft 42 such that the rider 44 is axially moved along the threaded shaft 42 as the shaft 42 is rotated.

The threaded shaft 42 is rotatable beared preferably in the lower housing part 18 and/or extents preferably parallel to the axial or longitudinal direction of the nebulizer 1 and/or to the axial or stroke movement of the container 3.

The drive gear 43 is located preferably at an upper end of the threaded shaft 42 and/or housing part 18, in particular such that it can mesh with a preferably inner toothing 45 of the housing or upper housing part 16 of the nebulizer 1 in the assembled state, i.e. when the housing of the nebulizer 1 is completely closed, as schematically shown in FIG. 9.

The counter device 23 or its rider 44, in particular the axial position of the rider 44 along the threaded shaft 42, may show or indicate the number of operations, in particular of tensioning, actuations or doses, which have already been performed or used with the current container 3 or which can still be performed with the current container 3. This operation number can in particularly been shown by a pointer 46 and/or an associated scale or the like which are visible reasonable through a corresponding window or transparent part of the housing part 18. It has to be noted that the number has not be shown precisely. In particular, it may be sufficient that the counter device 23, the rider 44 or its pointer 46 give a rough indication of the number. For this purpose, it may be sufficient if the scale shows only different colored areas or regions roughly indicating said number. Further, it has to be noted that other constructional solutions are possible as well.

The counter device 23 works preferably mechanically. This allows a very simple and robust construction and a very secure operation.

The counter device 23 may control or provide preferably locking of the nebulizer 1, indicating any required container replacement and/or container counting. For this purpose, the monitoring 23 or the rider 44 comprises preferably an actuation part 47 as schematically shown in FIG. 8. The actuation part 47 is preferably ridge-like and/or extending in axial direction and/or towards the upper housing part 16 and/or upwards.

The counter device 23 is associated to the respective housing part 18 and, thus, preferably to only one container 3 and counts operations of the nebulizer 1 with the respective container 3, i.e. counts (only) the number of doses of fluid 2 removed or still removable from this container 3.

It has to be noted that the first container 3 may be pre-installed together with the associated housing part 18 in the delivery state. This pre-installment is optional. Preferably, further separate containers 3 are delivered together with the nebulizer 1, wherein each container 3 is inseparably connected with an associated housing part 18 and, thus, with an associated counter device 23. Preferably, the counter device 23 or threaded shaft 42 of each housing part 18 is designed or provided with inhibition or brake means, such that any undesired counting or rotation is prevented before the respective housing part 18 is mounted to the nebulizer 1.

The nebulizer 1 comprises preferably a device 48 for counting the number of containers 3 that have been used or still can be used with the nebulizer 1 and/or for indicating or displaying said container numbers and/or symbols indicating container replacement and/or end of use. This device 48 is preferably for monitoring and/or user guidance.

Preferably, said numbers and/or symbols are visible or shown through a transparent part or window 49 of the nebulizer 1, in particular located in the upper housing part 16 as schematically indicated in FIG. 6. In particular, said numbers and/or symbols are shown at a side face of the nebulizer 1. Other arrangements or constructional solutions are possible.

Figure 11:
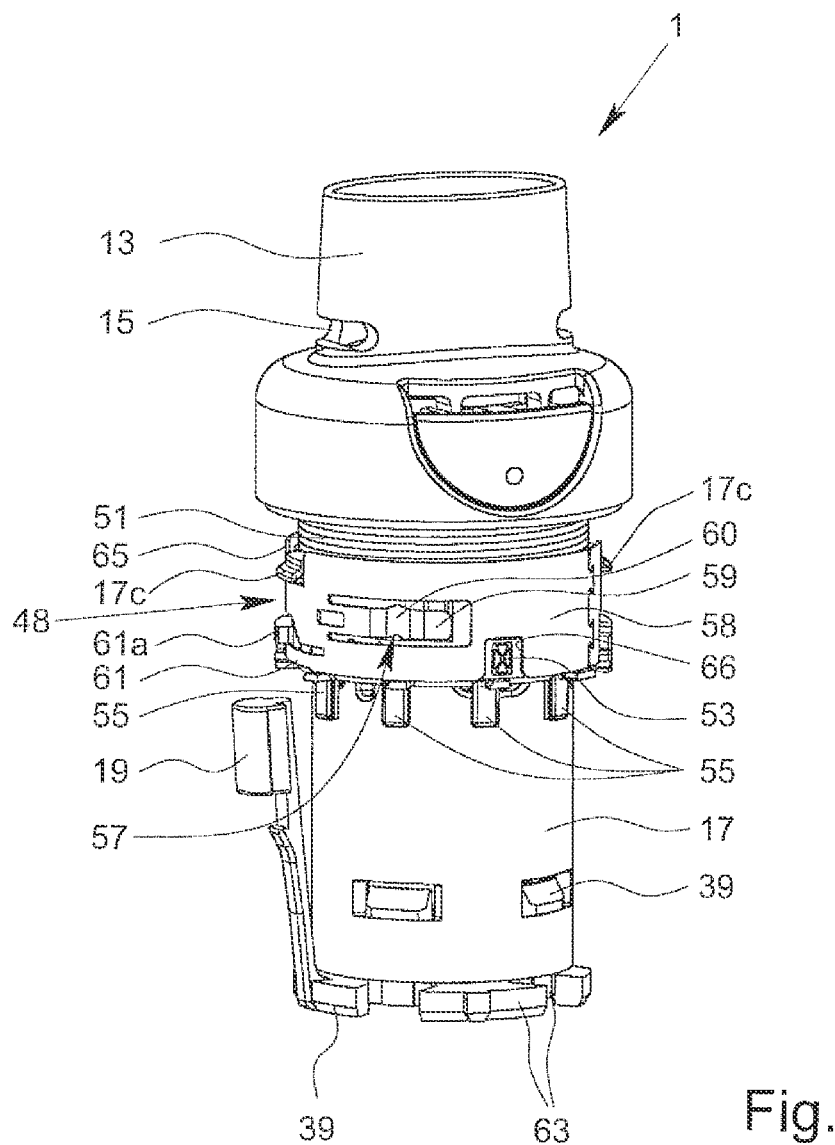
FIG. 11 a perspective view of an upper part of the nebulizer according to FIG. 6 without the housing part and with partly cut-away portions.

FIG. 11 shows the nebulizer 1 without lower housing part 18 and without container 3 in a schematic side view, wherein parts of the upper housing part 16 have been cut-away so that the monitoring or guidance device 48 of the nebulizer 1 is better visible.

The nebulizer 1 or device 48 comprises preferably a member 50 for indicating or displaying said container number, symbols, a status, and/or user instructions, e.g. relating to container replacement, and/or for controlling locking of the nebulizer 1. Thus, the member 50 is also called indicator member and/or control member. Preferably, both functions are achieved by the same or one single member 50. However, it is also possible that the indicator member and the control member are formed by separate parts or multiple parts. Preferably, the following description shall be understood in such a broad sense.

Preferably, the nebulizer 1 or device 48 comprises a spring 51 for driving or moving, in particular rotating, the member 50. This spring 51 is shown in FIGS. 7, 8, 9 and 11. Preferably, the member 50 is driven or rotated—in particular in multiple steps and/or from an initial (rotational) position to a final (rotational) position—only by spring force or by means of the spring 51.

The spring 51 is preferably a helical, sleeve-like, ring-like and/or torsional spring and/or a leg spring. It is preferably located coaxially with and/or adjacent to the driven member 50.

The spring 51 is preferably mounted in a biased state so that it applies a rotational force to the member 50. For this purpose, the spring 51 is supported with one end or leg at the nebulizer 1, in particular at the upper housing part 16, and engages with its other end or leg with member 50, e.g. by abutting a respective shoulder or bearing portion 67 (shown in FIGS. 12 and 13) of the member 50 or the like.

Figure 12:
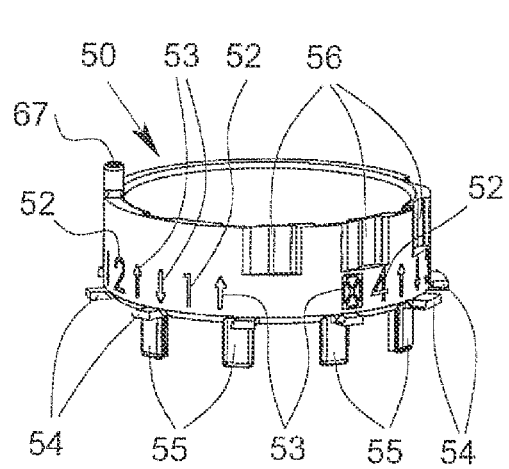
FIG. 12 a side view of a control/indicator member of the nebulizer according to FIG. 6.
Figure 13:
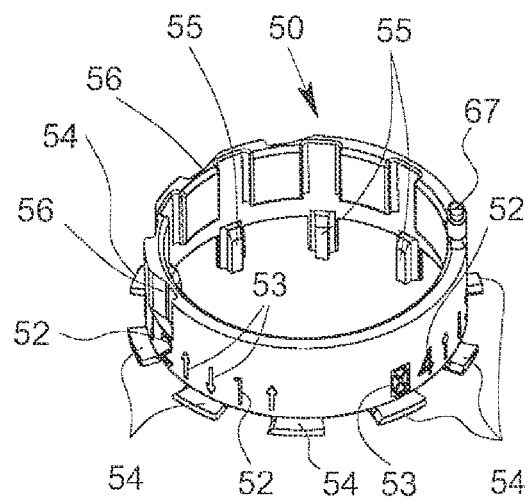
FIG. 13 a perspective view of the control/indicator member according to FIG. 12.

FIG. 12 shows a preferred embodiment of the member 50 in a schematic side view. FIG. 13 shows the member 50 in a perspective view.

The member 50 is preferably formed by a unitary and/or molded part. The member 50 is preferably at least essentially ring-like and forms or comprises a preferably closed ring.

The member 50 comprises or is provided with numbers 52 indicating said container number, and/or with said symbols 53 for user guidance, in particular for indicating container replacement and/or end of use of the nebulizer 1. Preferably, the numbers 52 and symbols 53 are shown and/or arranged on the member 50 such that one or more numbers 52 and one or more symbols 53 alternate. In particular, between preferably consecutive numbers 52 one or more symbols 53 are arranged and/or shown such that these symbols 53 indicate e.g. necessary container replacement, opening of the nebulizer 1, closing of the nebulizer 1 or the like. This may be communicated or indicated by respective arrows, colors, marks or the like as symbols 53. Further, the last symbol 53 may indicate end of use of the nebulizer 1 or complete locking of the nebulizer 1, e.g. by an "X" or the like. This symbol 53 may be shown for example when the allowable number of operations or actuations of the nebulizer 1 have been reached or exceeded of the last container 3 that may be used with or in the nebulizer 1, i.e. indicating total or final locking of the nebulizer 1. In the present embodiment, preferably a sequence of at least two different symbols 53 is shown between different or consecutive numbers 52. This sequence of symbols 53 comprises preferably a first symbol 53 (e.g. arrow downwards) indicating opening of the nebulizer 1 for container replacement and a second symbol 53 (e.g. arrow upwards) indicating closure of the nebulizer 1 for completing container replacement. However, it is also possible to show only one, potentially similar or identical symbol 53 between the different or consecutive numbers 52, such as one symbol 53 indicating container replacement. Preferably, only one special or end symbol 53, such as "X", is shown at the end when the allowable number of operations or actuations of the nebulizer 1 has been reached or exceeded for the last container 3 and/or when the nebulizer 1 is finally blocked and/or when no further container 3 can be inserted.

The member 50 comprises preferably engagement or stop portions 54 which are preferably formed by radial protrusions or the like in the present embodiment. The stop positions 54 are used preferably to allow or realize a stepwise movement or rotation (indexing) of the member 50.

The member 50 comprises further preferably blocking portions 55 which extend preferably axially and/or cooperate with the retaining element 19 to selectively lock the nebulizer 1 or housing part 18 against opening, in particular by selectively blocking the retaining element 19 against depressing or radial inward movement.

The member 50 comprises preferably control portions 56 for controlling or driving an associated lock 57 of the nebulizer 1. The control portions 56 are formed preferably by protrusions or indentions or inclined guiding surfaces or the like which preferably extend radially and/or which are preferably formed on an outer circumference of the member 50 or its ring portion. However, other arrangements are possible as well.

Figure 14:
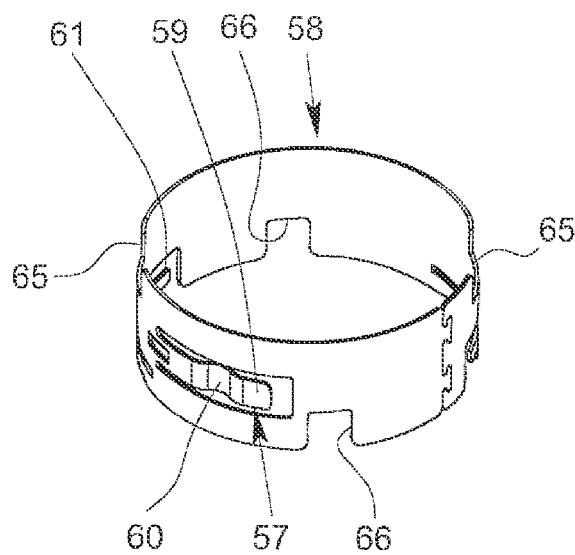
FIG. 14 a perspective side view of a lock member of the nebulizer according to FIG. 6.
Figure 15:
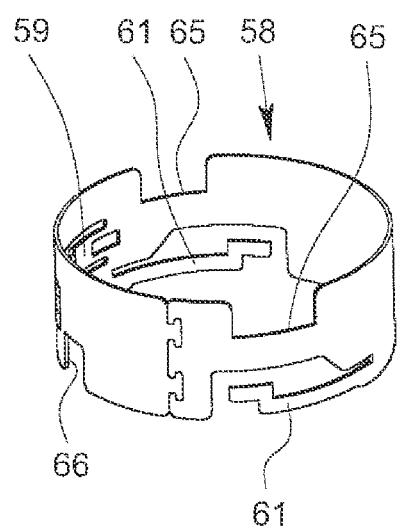
FIG. 15 another perspective view of the lock member according to FIG. 14.

The lock 57 is preferably formed by a locking member 58 or a portion 59 thereof, which is preferably tongue-like, leaf-like and/or flexible. FIG. 14 shows in a perspective view the locking member 58. FIG. 15 shows in other perspective view the locking member 58.

The locking member 58 is preferably made of metal and/or formed by plate material and/or a stamped part or the like. The locking member 58 is preferably ring-like and/or sleeve-like.

The portion 59 is preferably bent or indented or provided with such a form, in particular in radial direction and/or provided with a crimp, corrugation 60 or the like, for cooperating with the member 50 and/or at least one or more or all of the control portions 56, in particular such that depending on the rotational movement or position of the member 50 the portion 59 is radially flexed, in particular outwards, or not. For example, the control portions 56 are indented or recessed so that a portion 59 is not flexed radially outwards if the respective corrugation 60, which extends radially inwards from the respective portion 59, is received in a portion 56 located adjacent to this corrugation 60 on the inner side. If the member 50 is in another rotational portion, the corrugation 60 may abut on the non-recessed outer periphery of member 50 so that the respective portion 59 is flexed outwards and the lock 57 is closed. Thus, the lock 57 is driven or controlled, namely closed and opened, by means of the control member 50, in particular depending on its rotational position.

As already mentioned, the device 48 or member 50 is preferably driven by spring force, in the present embodiment by the force of spring 51. In particular, the member 50 is rotated or indexed stepwise by means of the force of the spring 51, wherein a ratchet or stop mechanism is provided to ensure the only stepwise moving or rotating of the member 50. In particular, stop means engage with the stop portions 54 of the member 50. In the present embodiment, the mechanism or stop means are preferably formed by one or two stop elements 61. The stop elements 61 are preferably formed like arms and/or by the locking member 58. The stop elements 61 are preferably elastically flexible to selectively allow a stop portion 54 to pass, i.e. to selectively allow the member 50 to index one step further, or to block a stop portion 54 and, thus, member 50 against further rotation. Preferably, the stop elements 61 are biased into a stopping position such that each stop element 61 extends into the way of movement of the stop portions 24 such that no stop portion 54 can pass the respective stop element 61.

Preferably, at least two stop elements 61 are provided and preferably offset such that stop elements 61 can be actuated alternatively to allow the member 50 to index or move further by one step, i.e. by one rotational movement or increment when the stop elements 61 are alternatively actuated, e.g. flexed, in particular in axial and/or radial direction, to allow one stop portion 54 to pass. The stop elements 61 are preferably flexed upwards to allow the respective stop portion 54 to pass. The actuation of the stop elements 61 will be explained in more detail below.

The stop elements 61 or its free ends may be provided with a broadened abutment or engagement body or surface, in particular by respectively bending the element or arm 61, by overmolding or the like. Each stop element 61 may be provided with a contact element 61a as schematically shown in FIG. 8. The contact element 61a may be formed by overmolding and/or may be shoe-like. The contact element 61a may form a stop or abutment for the stop portions 54 such that the member 50 is blocked against further rotation by force of spring 51 when the stop element 61 or contact element 61a is in the blocking position, here in the lower position shown in FIG. 8 where one stop portion 54 abuts the contact element 61a and cannot pass in circumferential direction. Here, the stop element 61 or contact element 61a has to be moved upwards or axially so that the blocked stop portion 51 can pass and the member 50 can index one step further in circumferential direction.

In the following, the operation and handling of the nebulizer 1 will be explained in more detail.

The nebulizer 1 may be delivered with a pre-installed container 3 and pre-attached housing part 18. In this case, the nebulizer 1 or its housing part 18 is not completely closed so that the container 3 is not yet fluidically connected or opened.

Alternatively the nebulizer 1 may be delivered with a separate container 3 and housing part 18. In this case the container 3 and the housing part 18 are preferably pre-assembled, i.e. form a unit that is separate from the nebulizer 1.

In any case, the nebulizer 1 is preferably delivered together with multiple containers 3, e.g. four or five containers 3, wherein each container 3 is inseparably connected to an associated housing part 18. These units of containers 3 and housing parts 18 can be exchanged so that the nebulizer 1 can be used with multiple containers 3 one after the other.

In both cases, the container 3 is preferably held unmoveably at or within the housing part 18 by the closed transportation lock 29 or securing device 39.

In both cases, the housing part 18 comprises preferably a coding, e.g. by one or more grooves, protrusions, ribs 62 or the like distributed around the inner circumference of the housing part 18 and/or axially extending, as schematically indicated in FIG. 10. This coding corresponds to the container 3 or the respective fluid 2 associated to the housing part 18. The coding matches to a complementary coding at the nebulizer 1, in particular at the inner part 17 or retaining part 39, and is preferably formed by respectively arranged and/or dimensioned indentions, coding portions 63, such as protrusion, indentions, recesses or the like, in particular formed by or at the retaining ring or part 39, as schematically shown in FIG. 11. Only when the codings match, the housing part 18 and, thus, the container 3 can be pre-installed and/or (completely) connected to or with the nebulizer 1.

Before (completely) closing the nebulizer 1 or its housing part 18, the device 48 or indicator member 50 may indicate by a respective symbol 53, such as an arrow pointing upwards, to completely close the nebulizer 1 or housing part 18.

When the housing part 18 is completely closed, the container 3 associated to the housing part 18 is fluidically connected to the nebulizer 1. This is detected or registered by the nebulizer 1 or device 48. This detection of the connection of the housing part 18 and, thus, of an associated container 3 is preferably realized mechanically, in particular by actuating one of the stop elements 61 to allow the member 50 to index one step further, i.e. until the other stop element 61 stops further indexing or rotation of the member 50. In the present embodiment, this registration or actuation is preferably achieved by a protrusion 64 formed at the housing part 18, in particular at its upper front face, as shown in particular in FIG. 7. When completely closing nebulizer 1, the protrusion 64 abuts one associated stop element 61 or contact element 61a and consequently flexes the stop element 61 or contact element 61a upwards such that it does not stop a corresponding stop portion 54 of the member 50 anymore, but allows the member 50 to move or rotate one step further, i.e. until the other stop element 61, which has not been flexed out of engagement in this state, stops further rotation by stopping a corresponding stop portion 54, preferably another one of stop portions 54.

As already mentioned, the container 3 is preferably inseparable from the housing part 18, the associated counter device 23 and/or associated securing device 32. Thus, after connection of a new container 3 with the nebulizer 1, the associated counter device 23 starts counting of the number of operations or uses of the respective container 3 that have already been performed or still can be performed. This operation number may be indicated or shown by the counter device 23 or its rider 44 or pointer 46 as already mentioned, while the device 48 or member 50 preferably only shows the container number 52, i.e. the number of containers 3 that have already been used or still can be used with the nebulizer 1.

Preferably, the nebulizer 1 is blocked against opening until the current container 3 has been (sufficiently) emptied, and/or until a predetermined number of operations or actuations has been reached or exceeded. This blocking of the nebulizer 1 or its housing part 18 against opening and/or container replacement is preferably achieved by a respective blocking portion 55 of the member 50 located below the retaining element 19 in this state as schematically indicated e.g. in FIG. 9, such that the retaining element 19 cannot be depressed, i.e. the nebulizer 1 cannot be opened and the housing part 18 cannot be detached.

When a predetermined number of operations or actuations of the nebulizer 1 has been reached, the nebulizer 1 is blocked against further use with the current container 3. This blocking is also called first locked state.

The first locked state is entered preferably by means of the counter device 23. In particular, the rider 44 or its actuation part 47 cooperate with the device 48 to enter the first locked state, when a predetermined number of operations have been reached or exceeded with the current container 3. Particularly, the rider 44 or its actuation part 47 reach an upper axial position in this state and actuate a respective stop element 61 or contact element 61a that is in blocking position or engagement with a stop portion 54. Thus, the stop element 61 or contact element 61a is preferably flexed or deformed such that the previously stopped stop portion 54 can pass and the member 50 is free to index one step further by the force of spring 51. FIG. 8 shows a situation, in which the rider 44 and actuation part 47 are already near the upper position and near the position to actuate the associated stop element 61 or contact element 61a. However, in the state shown in FIG. 8 one stop portion 54 and the member 50 are still blocked against rotating one step further.

The above indexing of the member 50 by one step leads to the first locked state. In this state, the nebulizer 1 or retaining element 19 is unblocked so that it can be opened. In particular, the blocking portion 55 blocking actuation of the retaining element 19 in the previous state is moved further, so that the retaining element 19 is not blocked any more, but can be actuated or pushed in order to allow detachment of the housing part 18 for container replacement.

In the first locked state the nebulizer 1, device 48 or member 50 indicates preferably by a respective symbol 53, in particular by an arrow pointing downwards, that container replacement is necessary and/or that the nebulizer 1 is locked against further use with the current container 3.

By the above indexing of the member 50 to reach the first locked state, the nebulizer 1 is locked against further use. This is achieved in particular in that the member 50 drives the lock 57 to lock the nebulizer 1 against further actuation, preferably against further tensioning of the drive spring 7 and/or against rotating of the housing part 18. This is preferably realized in that the rotation of the member 50 flexes the lock 57 or portion 59 of the locking member 58 radially outwards so that the flexed portion 59 leaves its non-locking position, into which it is biased, and locks further rotation of the inner part 17 relative to the upper housing part 16. This locking is in particularly achieved in that a free end of the portion 59 engages into a respective toothing or against respective abutment surfaces formed at the inner surface of the upper housing part 16. In this respect it has to be noted that the device 48 is preferably arranged or mounted on inner part 17, particular on its upper part 17a, wherein the preferably ring-like locking member 58 is preferably arranged around the rotatable member 50. The locking member 58 is preferably secured against rotation relative to the inner part 17 by respective form fit engagement, preferably of the inner part 17 or at least one protrusion 17c thereof into a recess 65 of the locking member 58. In the present embodiment, the recess 65 is preferably formed like a pocket or a portion cut-out of the periphery from one axial side. In particular, the locking member 58 may be provided with two or more recesses 65 as schematically shown in FIGS. 14 and 15, for engagement of respective protrusions 17c or the like, in particular of the associated inner part 17. However, other constructional solutions are possible as well.

Consequently, only member 50 is rotatable relative to inner part 17 and, thus, to locking member 58. However, locking member 58 is rotatable together with inner part 17 relative to upper housing part 16.

As already mentioned, the control member 50 is moveable, in particular rotatable, relative to locking member 58. This relative rotation is meant when any rotation or indexing of the control member 50 is mentioned. In this context, it has to be considered that the device 48 and the locking member 58 are rotated together with the inner part 17, but this rotation is different as this is the movement for tensioning the energy store, here spring 7, and/or for delivering or sucking fluid 2 out of the container 3 by in particular axial movement of the conveying element or tube 9.

The construction mentioned above, results in that the device 48 is rotated together with the inner part 17 each time the lower housing part 18 is rotated, i.e. when tensioning the drive spring 7. This rotation is preferably performed in 180° steps. Therefore, the device 48 or indicator member 50 comprises preferably two sets of respective number 52 and/or symbols 53 that are shown alternately through the window 49.

Thus, the member 50 comprises preferably two groups of numbers 52 and/or symbols 53, each group with the respective sequence of numbers 52 and/or symbols 53, wherein the groups are arranged offset by 180° on the member 50. This offset correspondence to the rotational angle for each rotational actuation of the lower housing part 18 and inner part 17 for tensioning the nebulizer 1/drive spring 7.

Preferably, the control portions 56 and/or the peripheral parts of the control member 50 in between the portion 56 form an inclined or control plane or surface cooperating with the portion 59 or its cam or corrugation 60 such that the lock 57 or the locking can be actuated alone by the force of the spring 51 acting on the member 50. In particular, the spring 51 or member 50 drives the lock 57. Further, the member 50 controls the lock 57 or the locking. As the member 50 also forms an indicator member, the indicator member drives the lock 57 or locking as well.

In the present embodiment, the locking member 58 is preferably arranged outside or around the control member 50 at least around a cylindrical main part of control member 50. In particular, the locking member 58 encompasses or covers at least substantially the cylindrical main part of the control member 50. The locking member 58 comprises preferably two openings 66 (shown in FIGS. 14 and 15) that are alternately aligned with window 49 depending on the rotational position of inner part 17 and, thus, of the locking member 58 so that the respective number 52 and/or symbol 53 is visible through the window 49 and through locking member 58.

In the first locked state, the member 50 is preferably stopped against further rotation by the protrusion 64 where any other part corresponding to the attachment of the housing part 18. When the housing part 18 is detached from the nebulizer 1 or its upper housing part 16 or inner part 17 for container replacement, this detachment is registered by unblocking the further movement or rotation of the member 50. In particular, a stop portion 54 of the member 50 which has been stopped by protrusion 64 or the like, can pass after detachment of the housing part 18 so that the member 50 can index one step further. In this further rotational position, the nebulizer 1 is still in its first locked state, i.e. is still locked against further use, in particular against further actuation or tensioning of the drive spring 7. However, the member 50 may show the next symbol 53, in particular an arrow pointing upwards, indicating that a new container 3 has to be connected and/or that a new housing part 18 has to be connected to the nebulizer 1. This situation correspondents to the initial situation before first assembly of the nebulizer 1 with the housing part 18 as already described.

It has to be noted that the stop element 8 is preferably blocked against actuation, in particular against release of the holder 6 and drive spring 7 in the first locked state. This actuation locking will also be achieved by the device 48 or member 50.

When the housing part 18 and the associated container 3 have been replaced, this is registered by the device 48, in particular by actuation of the corresponding stop element 61 by means of the protrusion 64. Then the member 50 indexes one step further and shows the next container number 52. Then, the lock 57 is reset, i.e. opened or unlocked again. Thus, the nebulizer 1 is unlocked and can be used further with the new container 3. Simultaneously, the container 3 or housing part 18 is preferably locked again against opening or container replacement, in particular in that the next blocking portion 55 is positioned below retaining element 19 to prevent actuation of the retaining element 19 which is necessary for opening the nebulizer 1.

The above sequence can be repeated, i.e. new containers 3 and new housing parts 18 can be used one after the after with the nebulizer 1, wherein the device 48 or indicator member 50 displays or shows the container number 52 and, preferably, symbols 53 for user guidance, in particular to indicate any necessary container replacement and/or indicating to open and close the nebulizer 1 or the like. The container number 52 relates in particular to the number of containers 3 that have already been used with the nebulizer 1 or still can be used with the nebulizer 1. In particular, one or more symbols 53 are displayed or shown alternately with the consecutive container numbers 52. This is realized preferably by one comment component, namely indicator member 50. However, other constructional realizations are possible.

Further, the display of the container numbers 52 and/or symbols 53 works preferably only mechanical.

In particular, the device 48 and/or the lock 57 work only mechanical.

After a predetermined number of containers 3 have been connected to or with the nebulizer 1, the nebulizer 1 will be blocked against further container replacement. After using the lastly inserted or connected container 3, the nebulizer 1 will enter the final locked state, i.e. the second locked state, preferably where the lock 57 or nebulizer 1 is blocked against resetting and/or the nebulizer 1 or housing part 18 is blocked against opening. This second locked state is entered in particular after the predetermined number of operations has been reached or exceeded with the ultimate, current container 3. Similar to the previous process the counter device 23 or its rider 44 or actuation part 47 actuates the device 48, in particular the corresponding stop element 61 to allow to index the member 50 one step further into its final rotational position. Thus, the second locked state is entered.

In the second lock state, the control member 50 cannot be rotated any further. This is realized in the present embodiment in particular in that the bearing portion 67 abuts one protrusion 17*c* of the inner part 17 engaging into one of the recesses 65. However, other constructional solutions are possible in order to realize the desired rotational stop or blocking for the control member 50 in the final rotational position, i.e. in the second locked state.

In the second locked state, the device 48 or member 50 does not allow opening of the nebulizer 1 or housing part 18 as it would be in the case in the first locked state. Instead, the member 50 comprises a respectively designed, preferably sufficiently long blocking portion 55 to block the retaining element 19 further against actuation and, thus, to block the nebulizer 1 against opening and container replacement.

In the second locked state, the nebulizer 1 can be locked against further actuation, in particular against tensioning of the drive spring 1 and/or rotation of the housing part 18 or inner part 17. This can be realized by actuating the lock 57, in particular by flexing portion 59 radially (preferably outwards) by the member 50 or its corresponding control portion 56. In the second locked state, the nebulizer 1 is preferably locked against any further discharge of fluid 2, in particular by blocking actuation of the stop element 8. This is preferably also realized by device 48.

Therefore, the nebulizer 1 cannot be used anymore after the second locked state has been entered. The second locked state is not reversible. In particular, resetting or unlocking of the lock 57 is not possible, but prevented in the second locked state.

As already outlined above, some general aspects or ideas of the nebulizer 1 according to the preferred embodiment can be summarized as indicated in the following.

The device 48 consists preferably only of two parts (control member 50 and locking member 58) or three parts (control member 50, spring 51 and locking member 58), but provides multiple functions, in particular displaying of numbers 42 and/or symbols 53 and/or user instructions, locking of the nebulizer 1 against further use, locking of the nebulizer 1 against tensioning, and/or locking of the nebulizer 1 against opening or container replacement.

The nebulizer 1 may comprise the indicator member 50 for showing numbers, in particular container numbers 52 and alternately symbols 53 indicating container replacement and/or nebulizer opening and/or closing.

The indicator member 50 may be moved or rotated stepwise by the force of the spring 51.

The indicator member 50 may drive the lock 57 of the nebulizer 1 such that the nebulizer 1 is locked against further use in the first locked state, when he container 3 has to be replaced, wherein the first locked state is reset by indexing the indicator member 50 and/or resetting the lock 57 if the container 3 and/or housing part 18 have been replaced.

The indicator member 50 is preferably ring-like.

The indicator member 50 works or shows the numbers 52 and/or symbols 53 mechanically.

The nebulizer 1 comprises preferably the lock 57 for locking the nebulizer 1 against further use in the first locked state, in particular when the container 3 has to be replaced.

Preferably, the first locked state is reset by resetting the lock 57, if the container 3 and/or housing part 18 have been replaced. With other words, the lock 57 is preferably resettable and can be used further after container replacement. In particular, an exchange or replacement of the lock 57 is not necessary to reuse the nebulizer 1.

The nebulizer 1 comprises preferably the control member 50 for controlling or driving the lock 57.

The control member 50 is preferably moved or rotated stepwise by the force of the spring 51.

The lock 57 and/or first locked state is preferably blocked against resetting in the second locked state.

Figure 16:
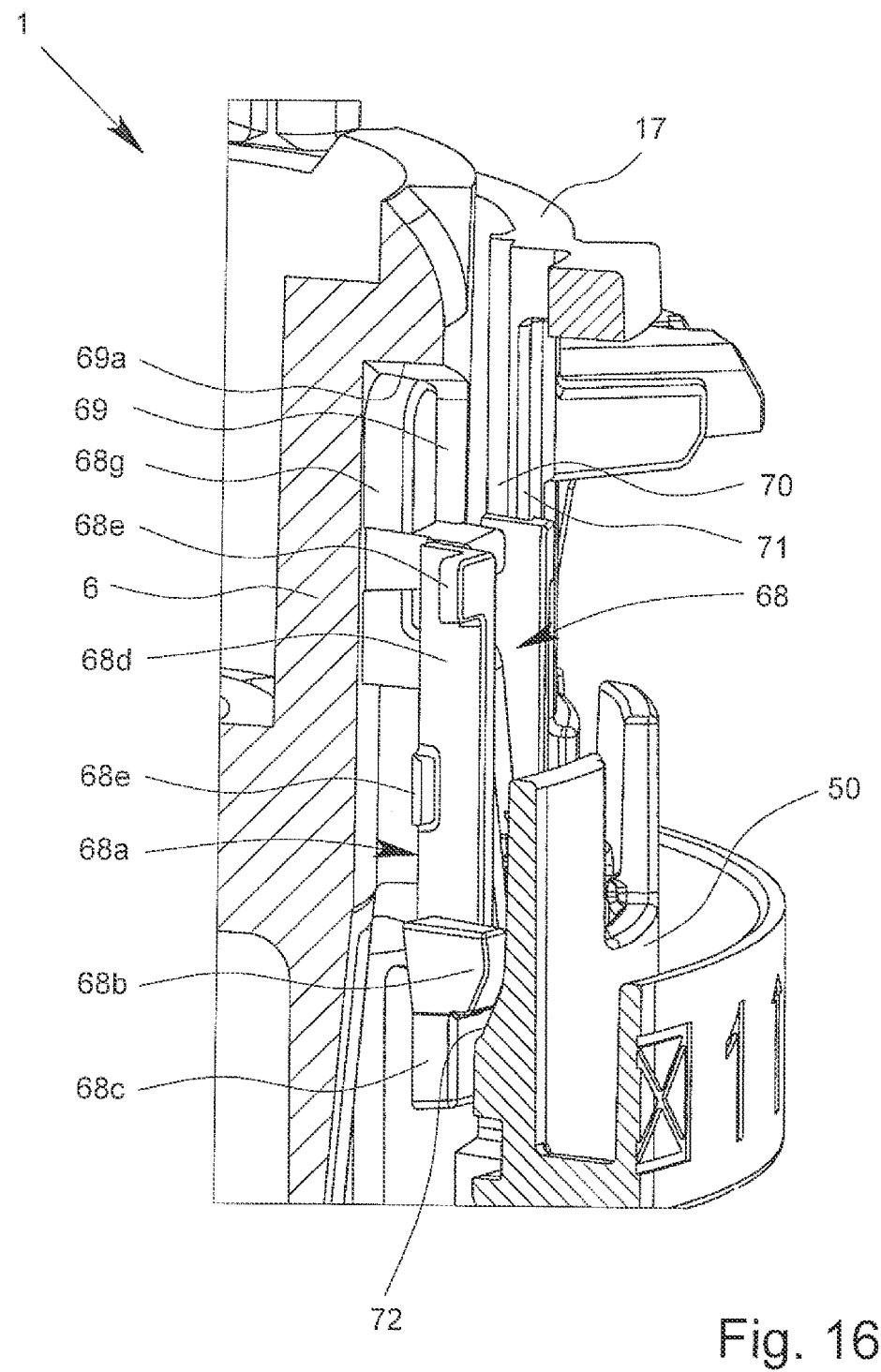
FIG. 16 a partial schematic section of the nebulizer with a blocking device according to the present invention.
Figure 17:
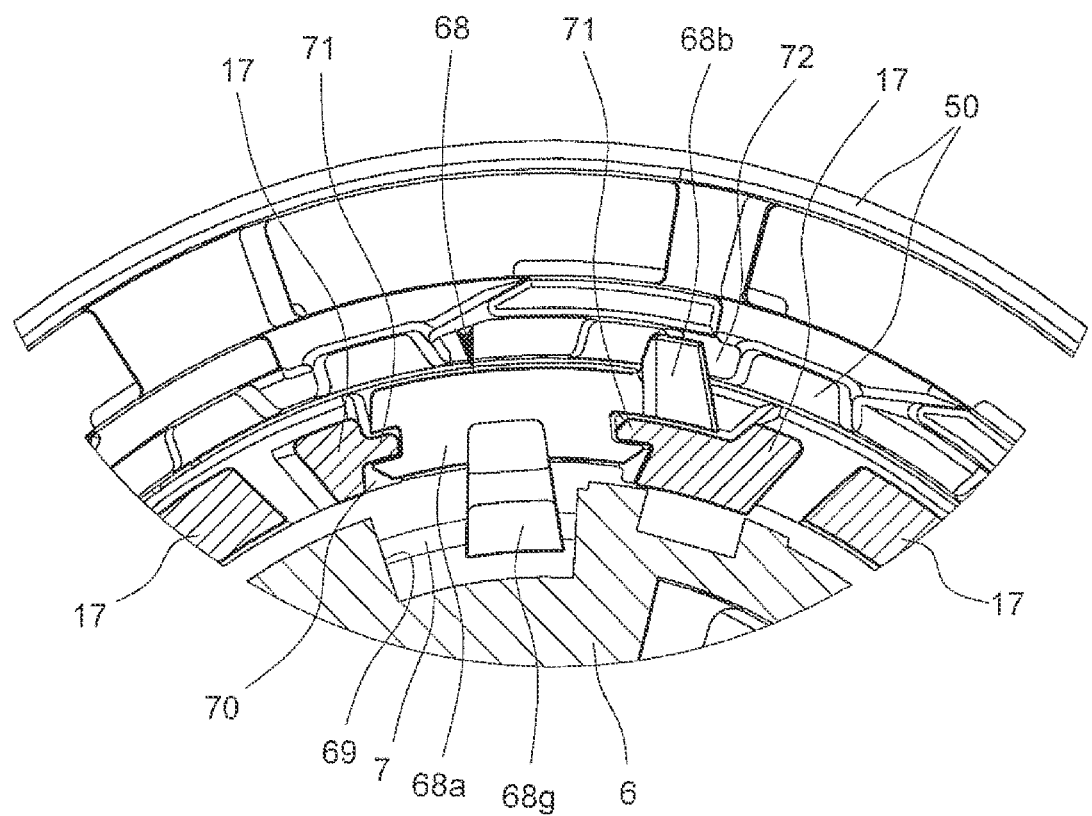
FIG. 17 a partial axial section of the area of FIG. 16 showing the blocking of an indicator member or control member by the blocking device.
Figure 18:
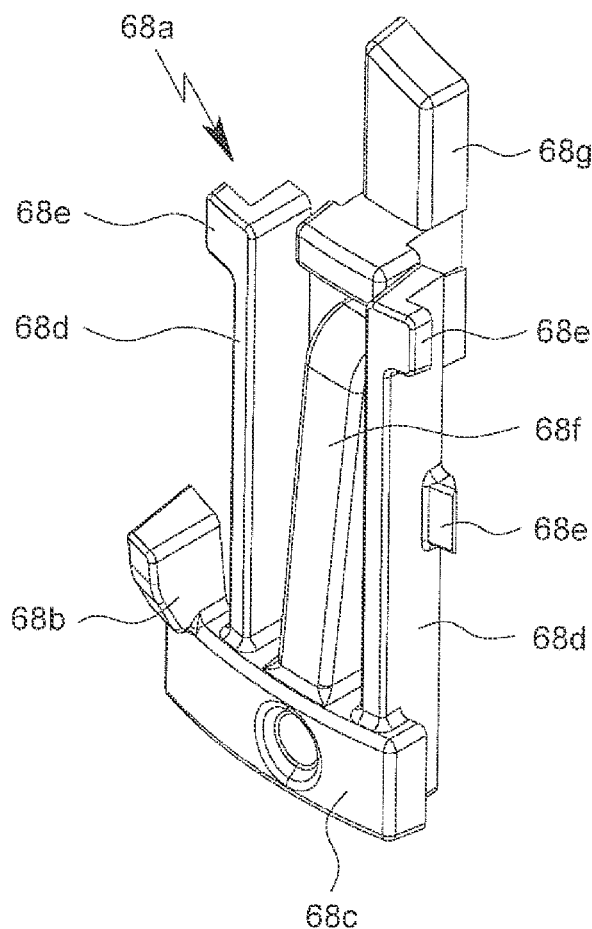
FIG. 18 a perspective view of the blocking device.
Figure 19:
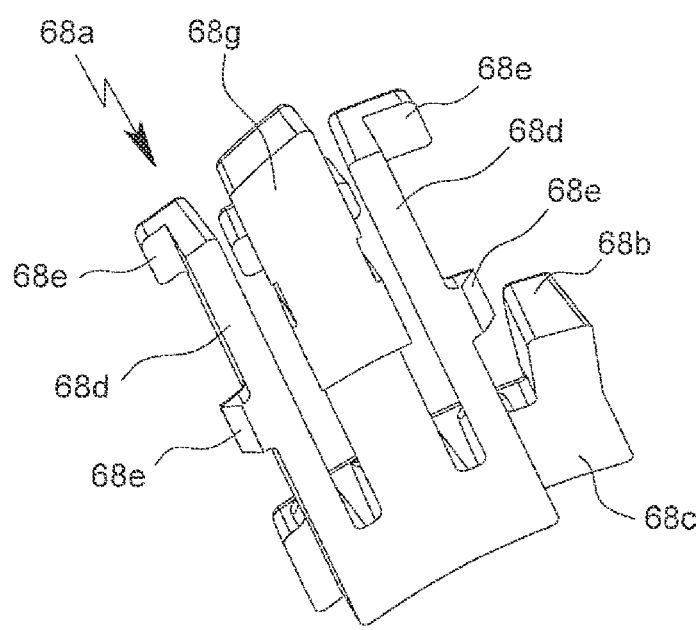
FIG. 19 another perspective view of the blocking device.

The second locked state is preferably entered when a predetermined number of containers 3 has been used or inserted into the nebulizer 1 and, preferably after a predetermined number of operations has been performed or exceeded with the nebulizer 1 after inserting the last container 3.

The control member 50 is preferably ring-like.

Preferably, the control member 50 forms the indicator member or vice versa.

The control member 50 displays preferably the numbers 52 of containers 3 that have been used or still can be used and/or the symbols 53 indicating containing replacement and/or user guidance or nebulizer handling.

The control member 50 blocks preferably opening of the nebulizer 1 and/or container replacement until a predetermined number of operations has been reached or exceeded with the current container 3.

Preferably, the nebulizer 1 is locked against opening or container replacement, in particular by means of the control member 50, in the second locked state.

Preferably, the nebulizer 1 is locked against opening or container replacement, in particular by means of the control member 50, before the first locked state has been reached.

Preferably, the lock 57 locks the nebulizer 1 in the first and/or second locked state against conveying fluid 2 into the pressure generator 5 and/or against tensioning of the drive spring 7 of the nebulizer 1 and/or against rotation or turning of the housing part 18 or inner part 17.

Preferably, the housing part 18 has to be replaced each time the container 3 is replaced. In particular, the container 3 is inseparable from the housing part 18 and/or counter device 23 or vice versa.

The securing device 32, in particular its moved apart locking portions **33*b*, preferably prevent that the used and/or detached container 3 can be re-connected to or reused with the nebulizer 1 once more and or prevent that a used or detached housing part 18 can be reconnected to the nebulizer 1** once more.

Preferably, the housing part 18 can be or has to be detached or opened for replacing the container 3.

Preferably, the securing device 32 is associated to the container 3 preventing that a used container 3 can be connected or used with the nebulizer once more.

FIGS. 16 to 25 show preferred aspects and/or preferred modifications of the nebulizer 1 according to the present invention. The previous descriptions and explanations apply preferably in addition even if a repetition is omitted.

FIG. 16 shows the upper part 16 of the nebulizer 1 in a partial, schematic sectional view. FIG. 17 shows a schematic sectional view perpendicular to the plane of FIG. 16 essentially in the plane of the indicator/control member 50.

The nebulizer 1 comprises preferably a blocking device 68 which—in the tensioned state of the nebulizer 1 or energy store or drive spring 7—blocks opening of the nebulizer 1 or housing and/or blocks detachment of the housing part 18 and/or blocks indexing of the member 50.

In particular, the member 50, preferably the rotational position of member 50, controls locking and unlocking of the housing or housing part 18 or retaining element 19. Thus, the blocking device 68 blocks opening of the housing or detaching of the housing part 18 in the tensioned state of the nebulizer 1 preferably via or by means of the indicator/control member 50, in particular by selectively blocking indexing of a member 50.

Preferably, the housing of the nebulizer 1 is blocked against opening in a form-fit manner when the nebulizer 1 is in its tensioned state.

Preferably, the blocking device 68 comprises a blocking element **68*a* as shown in different perspective views in FIGS. 18 and 19**.

The blocking device 68 or blocking element **68*a* comprises preferably a blocking part 68*b* for engaging or cooperating with the member 50 (see FIG. 17) and/or for blocking the member 50 against rotational indexing, when the nebulizer 1 or its energy store (drive string 7**) is in the tensioned state.

The blocking part **68*b*** protrudes or extends preferably radially.

The blocking element **68*a* or blocking part 68*b* is preferably moveable axially and/or selectively in engagement with member 50, in particular with a member recess 72**, and out of engagement.

Preferably, the blocking element **68*a* or blocking part 68*b* has different (axial) positions depending on the state of the nebulizer 1, namely tensioned or un-tensioned, and/or is moveable between different positions in response to the movement of the container 3 or holder 6 or drive spring 7 at its end at the holder 6**.

Thus, by the cooperation of blocking part **68*b* with the member 50, the blocking device 68 preferably always blocks the member 50 against rotational indexing, when the nebulizer 1 or its energy store (drive string 7**) is in the tensioned state.

FIGS. 16 and 17 show the nebulizer 1 in the tensioned state. The blocking device 68 blocks opening of the nebulizer 1. In particular, the blocking device 68 or its blocking element 68*a* blocks indexing of the member 50. The blocking element 68*a* or blocking part 68*b* engages preferably into member 50 or a member recess 72 such that member 50 cannot index one step further even if the predetermined number of uses of the nebulizer 1 with the current container 3 has been reached or exceeded, i.e. even if when the rider 44 or actuation part 47 has reached the upper axial position and actuated the respective stop element 61 or contact element 61*a* so that the member 50 should be free to index into the first or second locked state. However, the member 50 is blocked against indexing by the blocking device 68 or blocking part 68*b* until the nebulizer 1 is non-tensioned, i.e. the energy store or drive spring 7 is relaxed, and fluid 2 is dispensed for the last time from the current container 3.

Preferably, the blocking device 68 or its blocking part 68*b* prevent any indexing of the member 50 in the tensioned state of the nebulizer 1 independent on the position of the counter device 23 or its rider 44, i.e. each time the nebulizer 1 is tensioned.

The blocking element 68*a* is preferably received or guided in an inner recess of the inner part 17, in particular upper part 17*a* of inner part 17. The inner part 17 or upper part 17*a* comprises preferably at least one guiding element 71, in particular two guiding ribs or elements 71, in particular on opposite sides, for holding the blocking element 68*a*, in particular such that it can move axially relative to the inner part 17 and/or the member 50. Preferably, the blocking element 68*a* is snapped in a gliding rail or the like, here formed preferably by the guiding elements 71.

In the present embodiment, the blocking device 68 or blocking element 68*a* or blocking part 68*b* is moved or driven preferably by the movement of the container 3, the drive spring 7 or the holder 6. In particular, the blocking device 68 or blocking element 68*a* engages with an engagement part 68*g* into a holder recess 69 formed in the holder 6. In particular, the engagement or coupling of the blocking device 68 or blocking element 68*a* with the holder 6 or any other component driving or moving the blocking device 68 or blocking element 68*a* can be realized as a rigid connection or alternatively as a flexible or articulated engagement and/or as any other suitable drive connection e.g. with play, relative movability between the interconnected parts, an intermediate transmission element or the like.

In the tensioned state of the nebulizer the container 3, holder 6 and holder side of the drive spring 7 are in a different axial position than in the untensioned state. Thus, different positions of the blocking device 68 engaged to or triggered by at least one these components also correspond to the tensioned and untensioned state of the nebulizer 1, respectively.

In the present embodiment, the blocking device 68 or blocking element 68*a* comprises in addition to the blocking part 68*b* preferably a base 68*c* and/or guiding part 68*d*.

The base 68*c* holds preferably the blocking part 68*b* which protrudes preferably radially outwardly from the blocking element 68*a* or base 68*c*.

The guiding part 68*d* is provided preferably with noses 68*e*, in particular at opposite sides and respectively offset, such that the blocking element 68*a* or guiding part 68*d* is moveably guided and held by means of the guiding elements 71 of the inner part 17 engaging in between the noses 68*e*. However, other constructional solutions are possible as well.

The blocking device 68 or blocking element 68*a* comprises preferably an arm 68*f* for holding the engagement part 68*g*. In the present embodiment, the arm 68*f* extends essentially in axial direction and is inclined from the inner part 17 to the holder 6 within the inner part 17 so that the engagement part 68*g* can preferably completely sit in or engage into the holder recess 69 of the holder 6.

Generally it is possible to connect the engagement part 68*g* and, thus, the blocking element 68*a*, rigidly with one of the components, in particular the holder 6, for following the axial movement, in particular over the entire axial stroke. However, it is also possible to reduce the stroke of the engagement part 68*g* and, thus, of the blocking element 68*a* in comparison to the stroke of the container 3, holder 6 and the like, wherein different end stops limiting the stroke of the blocking element 68*a* can be provided, as it is preferred in the present embodiment.

In particular, the engagement part 68*g* has play (i.e. can move relative to the holder 6) in the holder recess 69 in the axial direction of movement. Alternatively or additionally, the holder recess 69 may be open towards the drive spring 7 so that the end of the drive spring 7 forms one (axial) end stop for the engagement part 63*g* and, thus, for the blocking element 68*a*. The other or upper end stop 69*a* is preferably formed by the other end of the holder recess 69, as shown in FIG. 16. However, the holder recess 69 could form both end stops if desired.

The position of the end stops define the end of the movement of the engagement part 68*g* relative to the axial stroke or movement of the container 3 and holder 6 and, thus, defines the coupling.

In the present embodiment, the holder recess 69 is preferably open towards the drive spring 7, but forms the upper end stop 69*a* as indicated in FIG. 16. The lower end stop is preferably formed by the drive spring 7, more precisely by its upper end, but could be formed by any suitable component.

The engagement part 68*g* follows—at least partly, in particular depending on the position of the end stops—the axial movement of the holder 6 and/or drive spring 7 and, thus, the back and forth movement of the container 3. This drive movement of the engagement part 68*g* preferably transmitted by arm 68*f* controls, moves or drives the blocking device 68 or blocking element 68*a*, in particular the blocking part 68*b*.

The orientation or position, such as upwards, downwards, upper, lower or the like mentioned above or used in the following, refers to the usual orientation of the nebulizer 1 or container 3 where the nebulizer 1 is at least essentially vertical and/or the outlet, nozzle 12 or mouthpiece 13 points upwards and/or the housing part 18 is at the bottom of the nebulizer 1 and/or the axial direction of the container 3 or its movement is vertical and/or the fluid outlet 24 or head of the container 3 is directed vertically upwards.

The counter device 23 is preferably driven by the movement, in particular rotation, of the housing part 18 or inner part 17 relative to the housing or upper part 16 for tensioning the nebulizer 1, energy store or drive spring 7. Thus, the counter device 23 or its rider 44 or actuation part 47 will reach its final axial end position (upper position) when the nebulizer 1 is tensioned for the last time. In this end position, the counter device 23 or its rider 44 or actuation part 47 unlocks the member 50 in particular by flexing stop element 61 or contact element 61*a* out of locking engagement with member 50 or the respective stop portion 54. However, the blocking device 68 or blocking part 68*b* still prevents the member 50 from indexing one step further into the first or second locked state until the nebulizer 1 has been actuated for the last time with the present container 3 to relax the energy store or drive spring 7.

The actuation of the nebulizer 1, i.e. release of drive spring 7, results namely in that the holder 6 and container 3 move axially towards the mouthpiece 13, i.e. upwards, and, simultaneously the blocking device 68 or its blocking part 68*b* is moved out of engagement with member recess 72 or member 50 so that member 50 is free to index one step into the first or second locked state.

In the present embodiment, the upper end of the drive spring 7 forms the lower end stop which abuts at the lower end of the engagement part 68*g* of the blocking element 68*a* and finally moves the blocking part 68*b* out of engagement with member recess 72 or member 50 when the holder 6 and container 3 move upwards.

It has to be noted that during each downward movement of the holder 6 or during each tensioning of the nebulizer 1 or drive spring 7, the holder 6 or more precisely, the upper end stop 69*a*, moves or pushes the engagement part 68*g* and, thus, the blocking element 68*a* downwards and/or into engagement with member 50, in particular such that blocking part 68*b* moves axially into member 50 or its member recess 72.

In the first locked state, the member 50 unlocks the retaining element 19 so that the nebulizer 1 or its housing can be opened, in particular the housing part 18 can be detached, for replacing the container 3, in particular together with the housing part 18 and counter device 23.

It has to be noted that the member 50 comprises preferably multiple engagement possibilities, in particular member recesses 72, so that the blocking device 68 or blocking part 68*b* can engage into the respective member recess 72 depending on the actual rotational position of the member 50 in response to the actual number of containers 3 already used.

Figure 20:
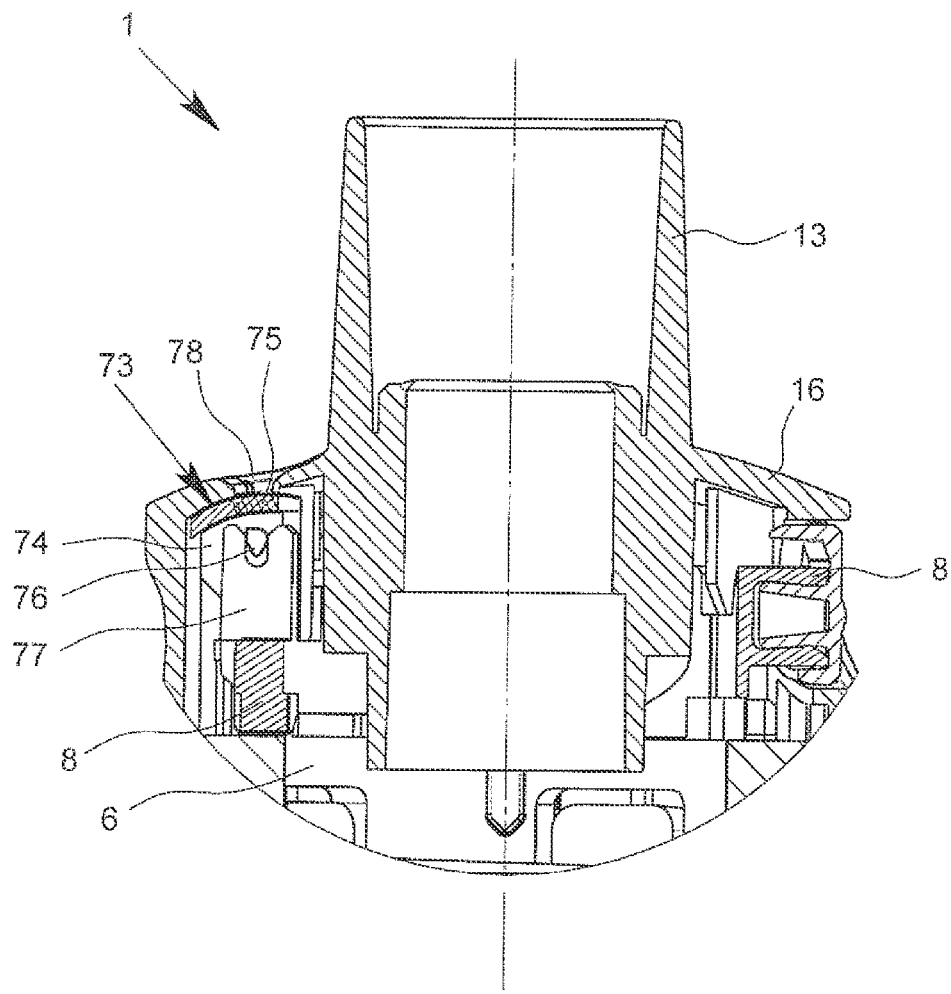
FIG. 20 a schematic section of an upper part of the nebulizer with an indicator device according to the present invention in a first position.

FIG. 20 shows in a schematic section an upper part of the nebulizer 1. The nebulizer 1 comprises preferably an indicator device 73 for indicating the state, in particular a tensioned state, of the nebulizer 1. In particular, the indicator device 73 indicates a tensioned state of the nebulizer 1 and a non-tensioned state of the nebulizer 1.

FIG. 20 shows the nebulizer 1 in the non-tensioned state. The stop element 8 is depressed or moved to the left side in the present representation.

Figure 21:
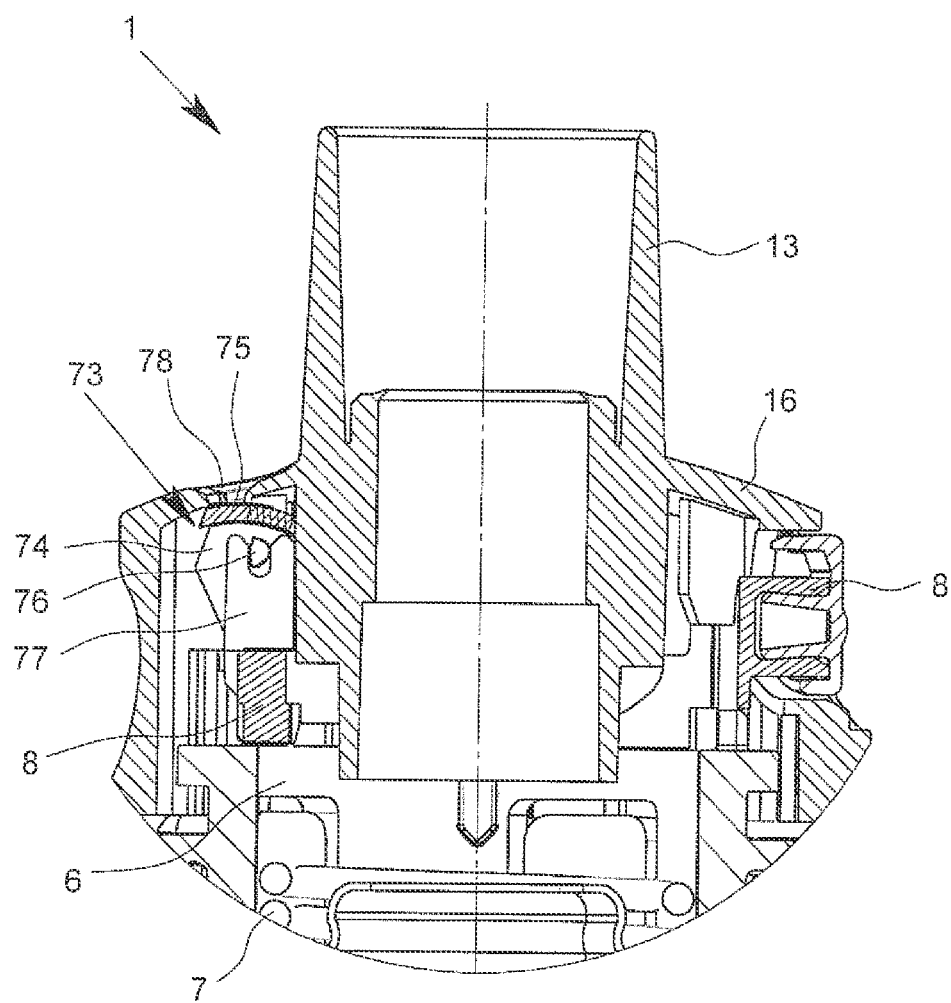
FIG. 21 a schematic section similar to FIG. 20 with the indicator device in a second position.

FIG. 21 shows a similar schematic section of nebulizer 1 as FIG. 20, wherein the nebulizer 1 is in the tensioned state. Here, the stop element 8 is in its blocking position where it is moved to the right side in the present representation and where it blocks upward movement of the holder 6 and, thus, of the container 3.

In the present embodiment, the indicator device 73 comprises preferably an indicator element 74. The indicator element 74 is preferably driven or moveable, in particular pivotable, by the stop element 8.

In the present embodiment, the indicator device 73 or indicator element 74 comprises preferably at least one indicator portion 75 with preferably different colors, symbols or the like for indicating the (pivotable) position of the indicator element 74 and/or of the stop element 8 and, thus, the state of the nebulizer 1 (tensioned or non-tensioned).

The nebulizer 1 or its upper part 16 comprises preferably a window 78 for viewing at least part of the indicator element 74 or indicator portion 75 to indicate the state.

In the present embodiment, the indicator element 74 comprises preferably an engagement portion 76, e.g. a protrusion, bolt or the like. The stop element 8 comprises preferably a drive portion 77, which is preferably fork-like and/or engages the engagement portion 76 for driving or moving, in particular pivoting, the indicator element 74 depending on the (radial) position of the stop element 8. However, other constructional solutions for coupling or linking the stop element 8 with the indicator device 73 are possible.

Figure 22:
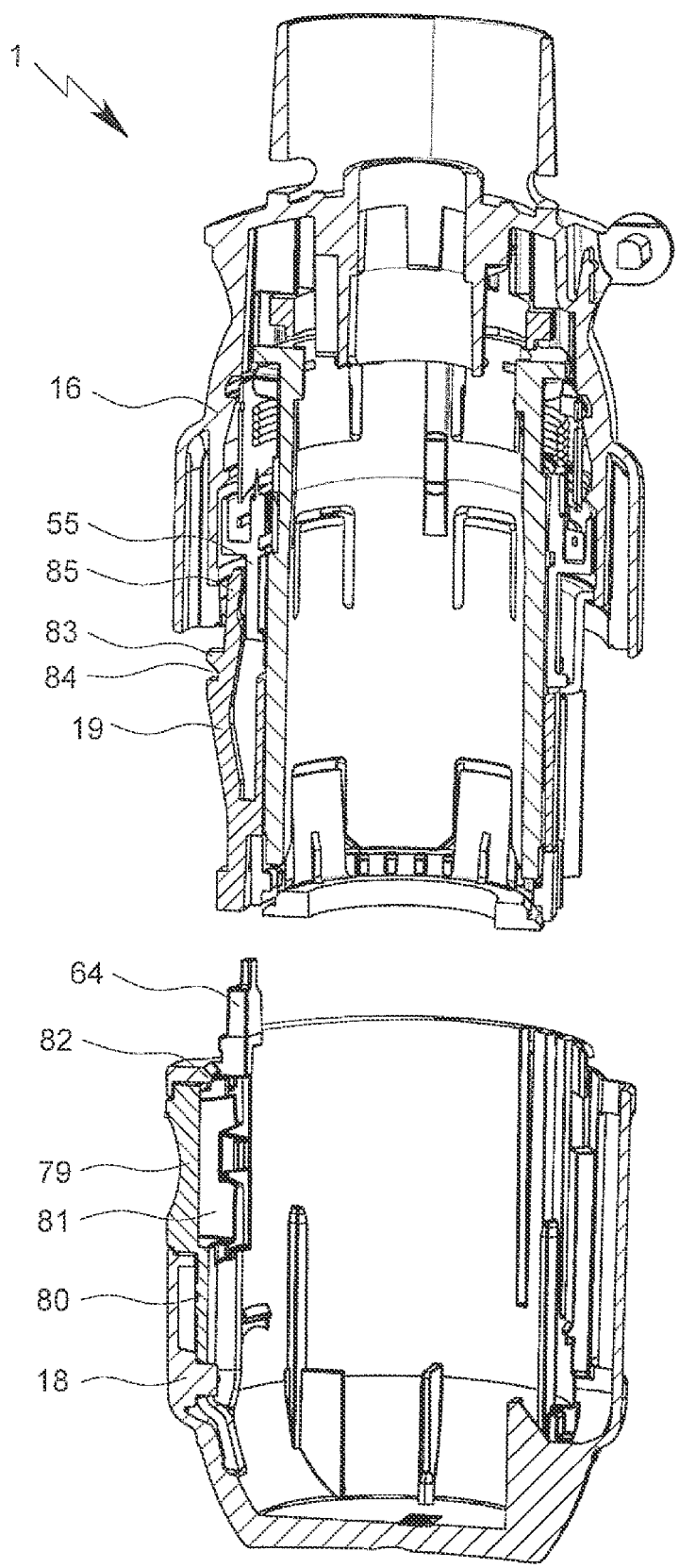
FIG. 22 a schematic section of the nebulizer according to the present invention with detached housing part comprising a depressable actuator member.
Figure 23:
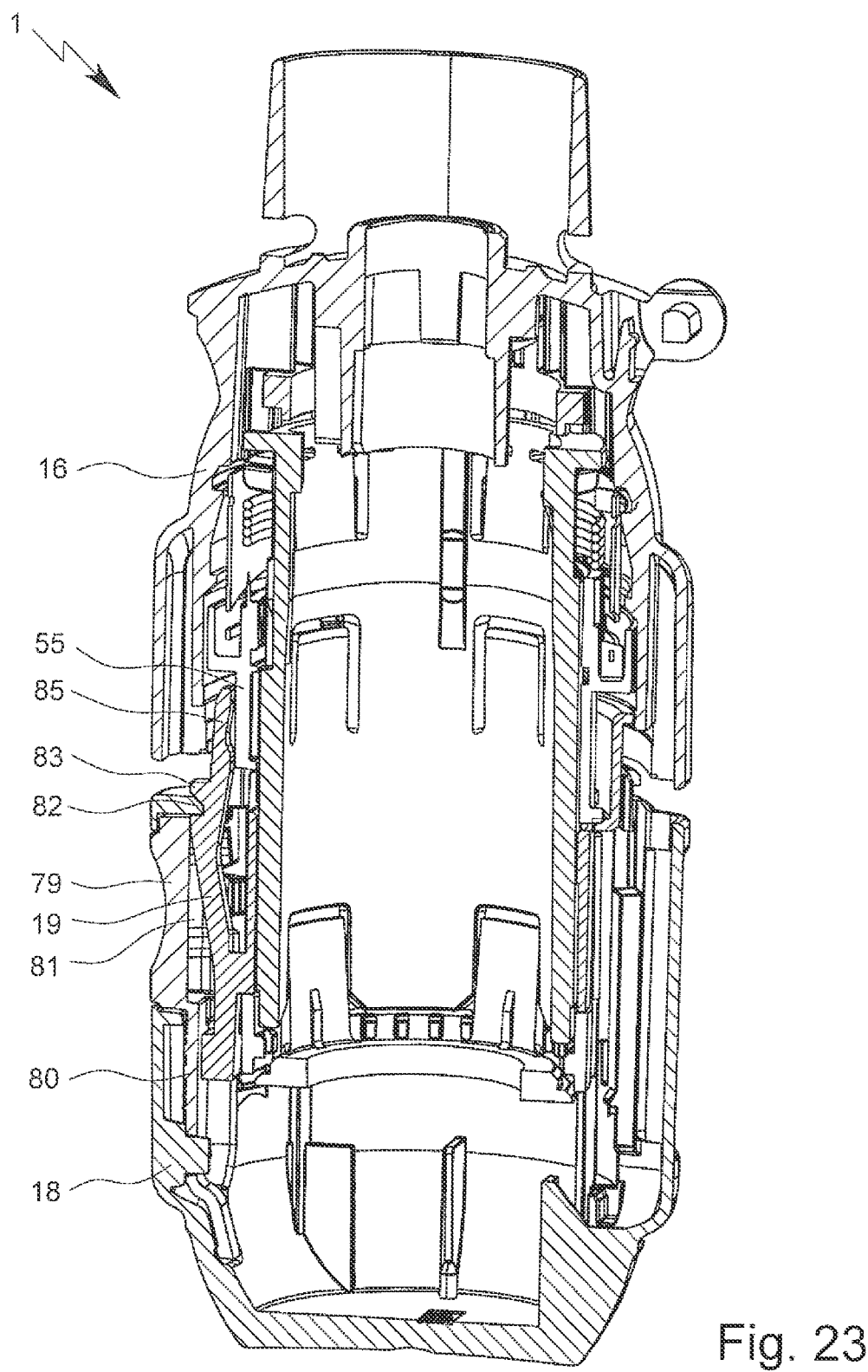
FIG. 23 a schematic section of the nebulizer according to FIG. 22 with partly attached housing part.
Figure 24:
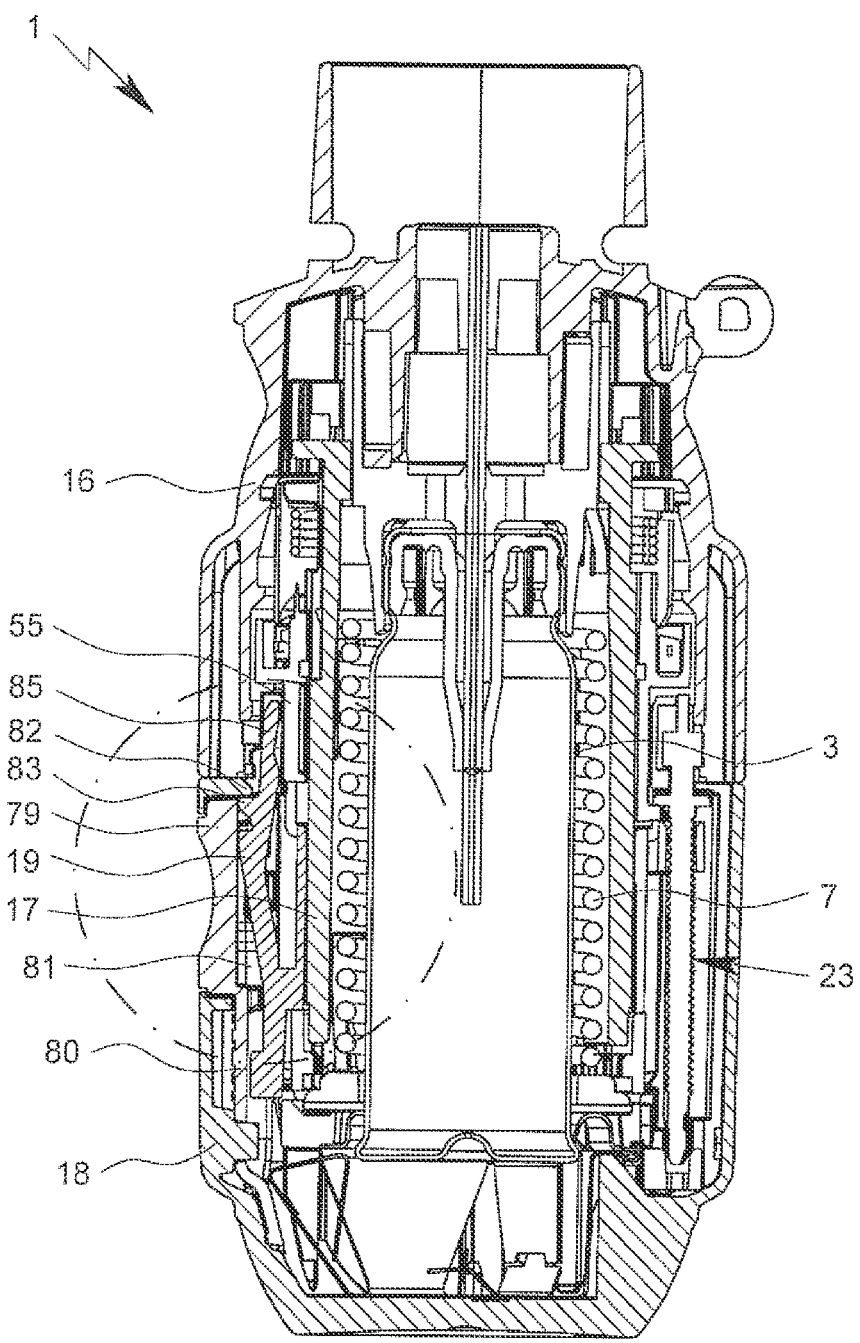
FIG. 24 a schematic section of the nebulizer according to FIG. 22 with completely attached housing part or completely housing.
Figure 25:
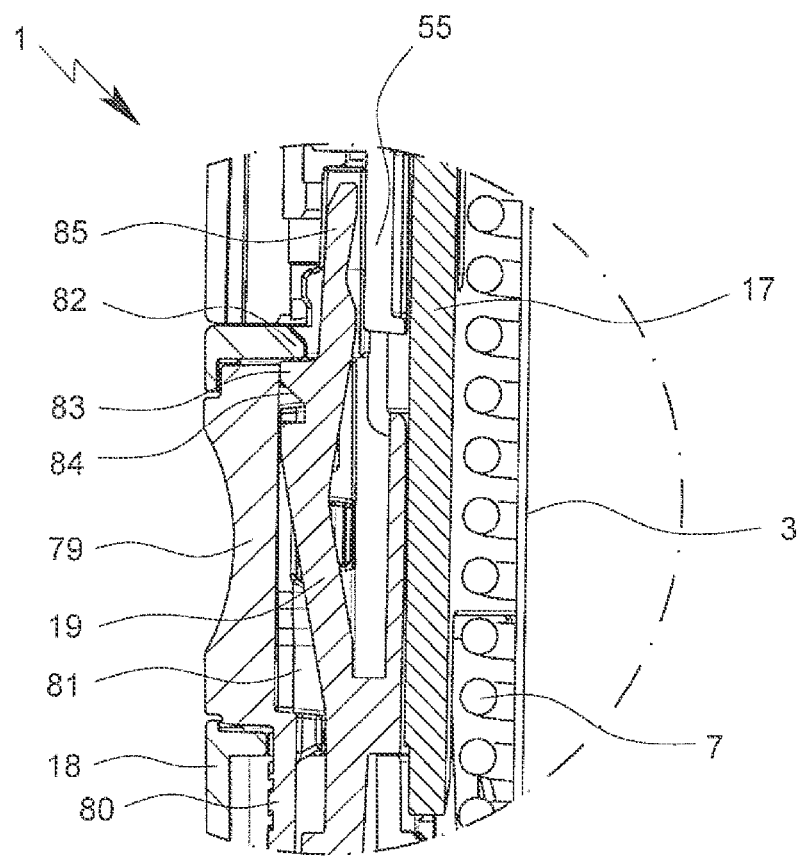
FIG. 25 a partial enlarged view of the encircled area of FIG. 24.

FIG. 22 shows the nebulizer 1 in a schematic sectional view without inner components, in particular without container 3, drive spring 7, holder 6, pressure generator 5 and nozzle 12. In FIG. 22, the housing part 18 is detached. FIG. 23 shows the nebulizer 1 in a similar schematic section as FIG. 22, wherein the housing part 18 is partly attached to the nebulizer 1 or inner part 17. FIG. 24 shows the nebulizer 1 in a similar schematic section as FIG. 22, wherein the housing part 18 is completely attached to the nebulizer 1 or inner part 17. FIG. 25 shows a partial enlargement of the encircled area of FIG. 24.

The nebulizer 1 comprises preferably a manually depressable actuator member 79, in particular in the form of a button or the like, at the housing part 18. Preferably, the actuator member 79 is received or held in a housing recess 81 formed at or by the housing part 18.

In the present embodiment, the actuator member 79 is preferably connected with or held by an actuator portion 80 or formed as a unitary piece with the actuator portion 80. Preferably, the actuator portion 80 is for securing the actuator member 79 at the housing part 18 and/or biasing the actuator member 79 into its non-depressed position shown in FIGS. 22 to 25.

Preferably, the retaining element 19 is connected with and not detachable from the nebulizer 1 or its inner part 17, i.e. is separated from the housing part 18 when detaching the housing part 18, as it is the case e.g. in the embodiment shown in FIGS. 7 and 9. However, in the preferred modification, the actuator member 79 is a separate part and is not formed by or connected with the retaining element 19, but separated therefrom when detaching the housing part 18 from the nebulizer 1 or inner part 17. This facilitates handling because the user (not shown) can leave a finger on the actuator member 79 when pulling the housing part 18 from the inner part 17 for opening the housing.

The housing part 18 comprises preferably a holding portion 82, in particular a shoulder or nose formed at the side of the housing recess 81 and/or adjacent to the actuator member 79, for interacting or cooperating with at the retaining element 19 or a retaining shoulder 83 of the retaining element 19.

FIG. 23 shows a partly attached or detached position of the housing part 18. Here, the holding portion 82 can engage into a retaining recess 84 formed at the retaining element 19 for holding the holding part 18 in this position.

Preferably, the retaining recess 84 and/or holding portion 82 comprises respectively inclined surfaces so that it is possible only to push the housing part 18 completely on the inner part 17, i.e. to completely close the housing, without actuating or depressing the actuator member 79 so that the nebulizer 1 can be completely closed as shown in FIGS. 24 and 25.

In the completely closed state, the holding portion 82 extends preferably over the retaining shoulder 83 so that the housing part 18 is secured in form-fit manner at the nebulizer 1 or inner part 17 or retaining element 19.

When depressing the actuator member 79, the retaining element 19 can flex inwardly (if not blocked by a blocking portion 55 of the member 50 as shown e.g. in FIG. 9) to move the retaining shoulder 83 inwards so that the housing part 18 can pass with its retaining shoulder 83 when detaching the housing part 18 in axial direction from the nebulizer 1.

The retaining element 19 comprises preferably a retaining portion 85 which extends towards the member 50 and can be selectively blocked against depression by the blocking portion 55 depending on the rotational position of the member 50. In FIGS. 22 to 25, the schematically shown blocking portion 55 adjacent to the retaining element 19 or retaining portion 85 is preferably circumferentially offset due to the rotational position of the member 50, so that the retaining portion 85 can move axially inwardly when the actuator member 79 is depressed and/or when attaching the housing part 18 to the nebulizer 1 and the passing of holding portion 82 results in an inward movement of the retaining element 19.

It has to noted that the blocking of opening of the nebulizer 1, i.e. the blocking of detaching the housing part 18 from the nebulizer 1 or inner part 17, functions in the previous embodiment preferably in a similar manner, namely by blocking the retaining element 19 against depression by means of one of the blocking portions 55 depending on the rotational position of the member 50 (compare FIG. 9 for example).

As already mentioned, individual features, aspects and/or principles of the embodiments described may also be combined with one another as desired and may be used particularly in the nebulizer according to FIGS. 1 and 5 but also in similar or different nebulizers.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g. powder inhalers or so-called metered dose inhalers.

Preferably, the fluid 2 is a liquid, as already mentioned, especially an aqueous pharmaceutical formulation or an ethanolic pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed in particular in WO 2009/115200 A1, preferably on pages 25 to 40, or in EP2 614 848 A1, paragraphs 0040 to 0087, which are incorporated herewith by reference. In particular, these may be aqueous or non-aqueous solutions, mixtures, formulations containing ethanol or free from any solvent, or the like.

LIST OF REFERENCE NUMERALS 1 nebulizer
2 fluid
3 container
4 bag
5 pressure generator
6 holder
7 drive spring
8 stop element
9 conveying tube
10 non-return valve
11 pressure chamber
12 nozzle
13 mouthpiece
14 aerosol
15 air supply opening
16 upper housing part
17 inner part
17a upper part of the inner part
17b lower part of the inner part
17c protrusion
18 housing part (lower part)
19 retaining element
20 spring
21 container base
22 piercing element
23 counter device
24 fluid outlet
25 first closure
26 second closure
27 closure part
28 flange
29 transportation lock
30 securing member
31 venting hole
32 securing device
33 holding element
33a end portion
33b locking portion
33c protrusion
34 locking element
34a end portion
34b actuation portion
35 base
36 spring portion
37 fixing portion
38 edge
39 retaining part
40 securing part
41 guiding surface
42 threaded shaft
43 drive gear
44 rider
45 toothing
46 pointer
47 actuation part
48 device
49 window
50 indicator/control member
51 spring
52 number
53 symbol
54 stop portion
55 blocking portion
56 control portion
57 lock
58 locking member
59 tongue-like portion
60 corrugation
61 stop element
61a contact element
62 rib 63 coding portion
64 protrusion
65 recess
66 opening
67 bearing portion
68 blocking device
68a blocking element
68b blocking part
68c base
68d guiding part
68e nose
68f arm
68g engagement part
69 holder recess
69a end stop
70 inner recess
71 guiding element
72 member recess
73 indicator device
74 indicator element
75 indicator portion
76 engagement portion
77 drive portion
78 window
79 actuator member
80 actuator portion
81 housing recess
82 holding portion
83 retaining shoulder
84 retaining recess
85 retaining portion

What is claimed is:

1. A nebulizer (1) for a fluid (2), comprising:
a container (3) containing the fluid (2);
a housing part (18) which can be detached from the nebulizer (1) for replacing the container (3);
an inner part (17);
a retaining element (19) connected with and not detachable from the inner part (17), wherein the housing part (18) is releasable fixed to the inner part (17) by the retaining element (19);
a delivery mechanism for dispensing the fluid (2); and
a manually depressible actuator member (79), which is a separate part from the retaining element (19) and acts on the retaining element (19),
wherein the actuator member (79) is depressed to elastically deform or flex the retaining element (19) to allow detachment of the housing part (18).

2. The nebulizer according to claim 1, wherein the housing part (18) forms a cap-like lower housing part and fits around or over a lower free end portion of the container (3).

3. The nebulizer according to claim 1, wherein the retaining element (19) forms a catch or snap for automatically holding or securing the housing part (18) when it is shifted onto or into the nebulizer (1).

4. The nebulizer according to claim 1, wherein the housing part (18) comprises a holding portion (82) for interacting or cooperating with the retaining element (19) or a retaining shoulder (83) of the retaining element (19).

5. The nebulizer according to claim 4, wherein, when depressing the actuator member (79), the retaining element (19) flexes inwardly to move the retaining shoulder (83) inwards, so that the housing part (18) passes the retaining shoulder (83) when detaching the housing part (18) in axial direction from the nebulizer (1).

6. The nebulizer according to claim 1, wherein the retaining element (19) is adapted to hold or secure the housing part (18) with two catch positions, i.e. a first catch position with partly closed housing part (18) of the nebulizer (1) and a second catch position with completely closed housing part (18).

7. The nebulizer according to claim 1, wherein the actuator member (79) is connected with or held by an actuator portion (80).

8. The nebulizer according to claim 7, wherein the actuator portion (80) biases the actuator member (79) into its non-depressed position.

9. The nebulizer according to claim 1, wherein the actuator member (79) is detachable together with the housing part (18) from the nebulizer (1).

10. The nebulizer according to claim 1, wherein the actuator member (79) is received or held in a housing recess (81) formed at or by the housing part (18).

11. The nebulizer according to claim 1, wherein the nebulizer (1) comprises a blocking device (68) adapted to block, when the nebulizer (1) is in a tensioned or loaded state, opening of the housing and/or indexing of an indicator member (50) which shows numbers (52) and/or symbols (53).

12. The nebulizer according to claim 11, wherein the retaining element (19) is blocked against deforming or flexing by the blocking device (68) or indicator member (50) in the tensioned state.

13. The nebulizer according to claim 11, wherein the blocking is terminated automatically after dispensing a dose of fluid (2).

14. The nebulizer according to claim 11, wherein the blocking device (68) blocks rotation of a control member (50) and/or of the indicator member (50) in the tensioned state.

15. The nebulizer according to claim 14, wherein the control member (50) and/or indicator member (50) controls the opening of the housing and/or locks the nebulizer or housing part (18) selectively against opening.

16. The nebulizer according to claim 11, wherein the blocking device (68) is driven, controlled or actuated by a position or movement of the container (3) within the housing and/or by a position or movement of a holder (6) holding the container (3) within the housing and/or by a position or movement of a drive spring (7).

17. The nebulizer according to claim 11, wherein the blocking device (68) comprises a blocking element (68a) which is axially moveably held by the inner part (17) of the nebulizer (1), where the inner part (17) is rotatable.

18. The nebulizer according to claim 11, wherein the housing is blocked against opening and/or container replacement until the container (3) has to be replaced due to multiple dispensing of fluid (2) and until the nebulizer (1) or an energy store has been released by dispensing fluid (2) or is in a non-tensioned state.

* * * * *